United States Patent
Wos et al.

(10) Patent No.: US 7,001,899 B2
(45) Date of Patent: Feb. 21, 2006

(54) INTERLEUKIN CONVERTING ENZYME INHIBITORS

(75) Inventors: John August Wos, Maineville, OH (US); Yili Wang, Mason, OH (US); Kofi Abeka Oppong, Fairfield, OH (US); Steven Victor O'Neil, Morrow, OH (US); Michael Christopher Laufersweiler, Maineville, OH (US); David Lindsey Soper, Mason, OH (US); Biswanath De, Cincinnati, OH (US); Thomas Prosser Demuth, Jr., Cincinnati, OH (US)

(73) Assignee: The Procter & Gamble Company, Cincinnati, OH (US)

(*) Notice: Subject to any disclaimer, the term of this patent is extended or adjusted under 35 U.S.C. 154(b) by 159 days.

(21) Appl. No.: 10/457,720

(22) Filed: Jun. 9, 2003

(65) Prior Publication Data
US 2004/0009966 A1    Jan. 15, 2004

Related U.S. Application Data

(60) Provisional application No. 60/387,531, filed on Jun. 10, 2002.

(51) Int. Cl.
| C07D 405/12 | (2006.01) |
| C07D 405/14 | (2006.01) |
| C07D 417/12 | (2006.01) |
| C07D 417/14 | (2006.01) |
| A61K 31/554 | (2006.01) |

(52) U.S. Cl. .................. 514/212.03; 514/212.08; 540/524; 540/527

(58) Field of Classification Search ............. 540/524, 540/527; 514/212.03, 212.08
See application file for complete search history.

(56) References Cited

U.S. PATENT DOCUMENTS

| | | | |
|---|---|---|---|
| 5,656,627 A | 8/1997 | Bemis et al. |
| 5,670,494 A | 9/1997 | Dolle et al. |
| 5,716,929 A | 2/1998 | Bemis et al. |
| 5,756,466 A | 5/1998 | Bemis et al. |
| 5,847,135 A | 12/1998 | Bemis et al. |
| 5,973,111 A | 10/1999 | Bemis et al. |
| 6,025,147 A | 2/2000 | Bemis et al. |
| 6,103,711 A | 8/2000 | Bemis et al. |
| 6,136,834 A | 10/2000 | Ohmoto et al. |
| 6,162,800 A | 12/2000 | Dolle et al. |
| 6,329,365 B1 | 12/2001 | Golec et al. |
| 6,350,741 B1 | 2/2002 | Golec et al. |
| 6,407,080 B1 | 6/2002 | Dolle et al. |

FOREIGN PATENT DOCUMENTS

| EP | 0761680 A2 | 3/1997 |
| JP | 10-251295 | 9/1997 |
| WO | WO 99/47545 A2 | 9/1999 |

OTHER PUBLICATIONS

Vo-Thanh et al. (Synlett (2001), (1), 37-40) Abstract.*
Piscopio et al. (Tetrahedron Letters 39 (1998) 2667-2670).*
Piscopio et al. (Tetrahedron 55 (1999) 8189-8198).*
Karanewsky, D.S., et al., "Conformationally Constrained Inhibitors of Caspase-10(Interleukin-1β Converting Enzyme) and of the Human CED-3 Homologue Caspase-3 (CPP32, Apopain)", *Bioorganic & Medicinal Chemistry Letters*, 1998, vol. 8, No. 19, pp. 2757-2762.

* cited by examiner

Primary Examiner—Bruck Kifle
(74) Attorney, Agent, or Firm—Richard S. Echler, Sr.

(57) ABSTRACT

The present invention relates to novel compounds, compositions comprising said compounds, and uses thereof, said compounds having the formula:

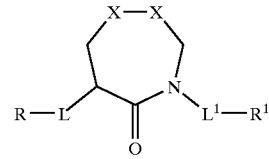

wherein each X is independently selected from:
i) —C(W)$_2$—;
ii) —C(O)—;
iii) —NR$^2$—;
iv) —S—;
v) —S(O)—;
vi) —S(O)$_2$—;
vii) two units, one from each adjacent X unit, can be taken together to form a substituted or unsubstituted double bond having the formula —CW=CW—; wherein each W is hydrogen of a unit having the formula —(L$^2$)$_j$—R$^2$, the index j is 0 or 1;
R is a carbocyclic or heterocyclic aryl ring;
R$^1$ is a cysteine trap;
each R$^2$ is independently a suitable substituent; and
L, L$^1$, and L$^2$ are linking units.

41 Claims, No Drawings

INTERLEUKIN CONVERTING ENZYME INHIBITORS

CROSS REFERENCE TO RELATED APPLICATIONS

This application claims priority under Title 35, United States Code 119(e) from Provisional Application Ser. No. 60/387,531, filed Jun. 10, 2002.

FIELD OF THE INVENTION

The present invention relates to novel 7-member ring heterocycles that are Interleukin 1β converting enzyme (ICE) inhibitors. The present invention also relates to pharmaceutical compositions comprising said inhibitors. The present invention further relates to methods for controlling one or more disease processes related to interleukin 1β activity.

BACKGROUND OF THE INVENTION

Cytokines, in general, are important signaling molecules that are essential to immune and inflammatory responses in mammals. Interleukin-1β and IL-18 are key components of the cytokine network. IL-1β stimulates the production of Tumor Necrosis Factor-α (TNF-α), and the combined action of IL-1β, IL-18 and TNF-α induces further cytokine production, chemokine production, expression of cellular adhesion molecules, and increased vascular permeability. In addition, IL-1β stimulates fibroblast differentiation and proliferation, the production of prostaglandins, collagenase and phospholipase by synovial cell and chondrocytes, basophil and eosinophil degranulation, and neutrophil activation. These mediators contribute to autoimmune and inflammatory disorders in many organ systems.

IL-1β possesses diverse biological effects contributing to the pathogenesis of acute and chronic inflammatory and autoimmune diseases (C A Dinarello, *Blood,* (1996) 87, 2095). For example, II-1β contributes to disease progression in rheumatoid arthritis and osteoarthritis, where it mediates inflammatory symptoms, contributes to the destruction of cartilage proteoglycan, and also contributes to bone loss in afflicted joints. IL-1β overexpression also contributes to disease progression in atherosclerosis by regulating the expression and activation of matrix metalloproteases. Other conditions where IL-1β plays a major role in pathogenesis include sepsis syndrome, inflammatory bowel syndrome, acute and chronic myelogenous leukemia, insulin-dependent diabetes mellitus, osteoporosis, and periodontal disease.

The caspases are a family of structurally similar, intracellular cysteine proteases that play an important role in cytokine maturation and apoptosis. Caspase-1 (interleukin-1β converting enzyme, ICE) is primarily responsible for key steps in immunity and the inflammatory response since it catalyzes the proteolytic cleavage of the pro-inflammatory cytokines pro-IL-1β and pro-IL-18 to the bioactive forms IL-1β and IL-18. Since IL-1β triggers a multitude of biological responses and is implicated in the pathogenesis of many inflammatory diseases, as outlined above, the inhibition of ICE is a recognized target for therapeutic intervention. Therefore, ICE inhibitors have utility for the treatment of inflammatory diseases and autoimmune diseases, such as RA and OA. In addition, other caspases and related homologs of ICE appear to be involved regulating biological processes such as apoptosis. Therefore, inhibition of caspases also provides a recognized therapeutic approach for treating additional pathological conditions. Diseases where caspase inhibitors can provide theraputic utility include neurodegenerative diseases (such as Alzheimer's, Huntington's, and Parkinson's diseases), ischemia, stroke, and trauma.

There is therefore a long felt need in the art for pharmaceutical compositions which comprise novel active ingredients for reversibly or irreversibly inhibiting Caspase enzymes resulting in the treatment of pathological conditions and diseases described further herein, inter alia, inflammation of joints and other forms of synovial tissue associated with osteoarthritis and rheumatoid arthritis, Huntington's Disease, Alzheimer's disease, neuronal death, brain, intestinal or mycardial ischemia, repurfusion injury, endotoxic shock, amyotrophic lateral sclerosis, multiple sclerosis, atherosclerosis, hepatitis, inflammatory bowel syndrome, shigellosis, meningitis, sepsis, acute and chronic myelogenous leukemia, insulin-dependent diabetes mellitus, osteoporosis, and periodontal disease. Each of these disease states involves cytokine activity, which can be abated, controlled or otherwise mediated by the limiting or stopping the activity of one or more Caspase enzymes

SUMMARY OF THE INVENTION

The present invention meets the aforementioned needs in that it has been surprisingly discovered that certain 7-member ring heterocycles are effective for inhibiting Interleukin Converting Enzyme and thereby preventing, abating, or otherwise controlling the extracellular release of the 17 kD IL-1β enzyme which is proposed to be the active component responsible for the herein described disease states.

The first aspect of the present invention relates to compounds which are capable off interfering with the release of the IL-1β protease, said compounds having the formula:

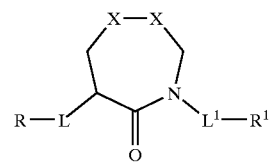

wherein each X is independently selected from:
i) —C(W)$_2$—;
ii) —C(O)—;
iii) —NR$^2$—;
iv) —S—;
v) —S(O)—;
vi) —S(O)$_2$—;
vii) two units, one from each adjacent X unit, can be taken together to form a substituted or unsubstituted double bond having the formula —CW═CW—; wherein each W is hydrogen of a unit having the formula —(L$^2$)$_j$—R$^2$, the index j is 0 or 1;
R is a carbocyclic or heterocyclic aryl ring;
R$^1$ is a cysteine trap;
each R$^2$ is independently selected from the group consisting of:
i) hydrogen;
ii) a hydrocarbyl unit having the formula: —[C(R$^3$)$_2$]$_p$(CH═CH)$_q$R$^3$;
iii) —C(═Z)R$^3$;
iv) —C(═Z)AR$^3$;
v) —C(═Z)[C(R$^3$)$_2$]$_p$(CH═CH)$_q$R$^3$;

vi) —C(=Z)N(R³)₂;
vii) —C(=Z)NR³N(R³)₂;
viii) —CN;
xix) —CF₃;
x) —N(R³)₂;
xi) —NR³CN;
xii) —NR³C(=Z)R³;
xiii) —NR³C(=Z)N(R³)₂;
xiv) —NHN(R³)₂;
xv) —NHOR³;
xvi) —NO₂;
xvii) —OR³;
xviii) —OCF₃;
xix) —F, —Cl, —Br, or —I;
xx) —SO₃M;
xxi) —OSO₃M;
xxii) —SO₂N(R³)₂;
xxiii) —SO₂R³;
xxiv) —P(O)(OR³)R³;
xxv) —P(O)(OR³)₂;
xxvi) and mixtures thereof;

each R³ is independently hydrogen, substituted or unsubstituted $C_1$–$C_{20}$ linear, branched, or cyclic alkyl, substituted or unsubstituted $C_6$–$C_{20}$ aryl, $C_1$–$C_{20}$ substituted or unsubstituted heterocyclic, $C_1$–$C_{20}$ substituted or unsubstituted heteroaryl; Z is —O—, —S—, —NR³—, and mixtures thereof; M is hydrogen, or a salt forming cation; the index p is from 0 to 12; the index q is from 0 to 12;

L, L¹, and L² are each independently a linking group having the formula:

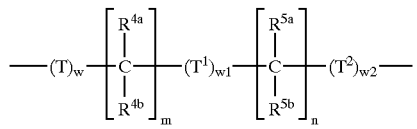

T, T¹, and T² are each independently selected from the group consisting of:
i) —NR⁶—;
ii) —O—;
iii) —S(O)₂—;
iv) —NR⁶S(O)₂—;
v) —S(O)₂NR⁶—; and
vi) mixtures thereof;

R⁶ is hydrogen, substituted or unsubstituted $C_1$–$C_{10}$ linear, branched, or cyclic alkyl, $C_6$–$C_{10}$ aryl, $C_7$–$C_{12}$ alkylene-aryl, and mixtures thereof; the indices w, w¹, and w² are each independently 0 or 1;

R⁴ᵃ, R⁴ᵇ, R⁵ᵃ, and R⁵ᵇ are each independently:
i) hydrogen;
ii) $C_1$–$C_4$ linear, branched, and cyclic alkyl;
iii) R⁴ᵃ and R⁴ᵇ or R⁵ᵃ, and R⁵ᵇ can be taken together to form a carbonyl unit;
iv) two R⁴ᵃ or two R⁴ᵇ units from adjacent carbon atoms or two R⁵ᵃ or two R⁵ᵇ units from adjacent carbon atoms can be taken together to form a double bond; and
v) mixtures thereof;
the index m is from 0 to 5; the index n is from 0 to 5.

Another aspect of the present invention relates to pharmaceutical compositions. The compounds of the present invention have improved oral bioavailability and this advantage is made use of by the second aspect of the present invention wherein the formulator can deliver the compounds of the present invention to a human or higher mammal by administering a composition comprising:
a) an effective amount of one or more interleukin-1β converting enzyme inhibitors according to the present invention; and
b) one or more pharmaceutically acceptable excipients.

As described herein below, the compositions of the present invention are effective in controlling one or more interleukin-1β converting enzyme inhibitor mediated or interleukin-1β converting enzyme inhibitor modulated mammalian diseases or conditions.

A further aspect of the present invention relates to methods for controlling diseases or disease states which are related to or caused by the increased activity of one or more Caspase enzymes, inter alia, Interleukin-1β Converting Enzyme (Caspase-1). The unmediated or uncontrolled activity of said enzymes can cause the release of higher levels of cytokines which exacerbate the disease state. The methods of the present invention control the amplification of IL-1β and other cytokines which are capable of being released by controlling the initial release of IL-1β.

Further, this invention relates to methods for treating diseases mediated by Caspase enzymes, including for example, acute and chronic inflammatory-mediated diseases, autoimmune diseases, destructive bone diseases, proliferative disorders, infectious diseases, and degenerative diseases.

In addition, this invention also relates to methods of treating diseases mediated by IL-1β. Specifically, the subject invention relates to methods for treating pathological conditions and diseases, such as neuronal death, brain, intestinal or mycardial ischemia, repurfusion injury, endotoxic shock, amyotrophic lateral sclerosis, multiple sclerosis, Parkinson's disease, Huntington's disease, Alzheimer's disease, atherosclerosis, hepatitis, inflammatory bowel syndrome, shigellosis, meningitis, sepsis, acute and chronic myelogenous leukemia, insulin-dependent diabetes mellitus, osteoporosis, periodontal disease, rheumatoid arthritis (RA) and osteoarthritis (OA).

These and other objects, features, and advantages will become apparent to those of ordinary skill in the art from a reading of the following detailed description and the appended claims. All percentages, ratios and proportions herein are by weight, unless otherwise specified. All temperatures are in degrees Celsius (° C.) unless otherwise specified.

DETAILED DESCRIPTION OF THE INVENTION

The present invention relates to compounds which are interleukin-1β converting enzyme inhibitors, said compounds comprising an 8,6-fused ring system. Interleukin-1β is a cyctokine released by a chemical reaction catalyzed by the enzyme Caspase-1 (ICE) and the present invention specifically targets the inhibition of Caspase-1. The compounds of the present invention are surprisingly specific for inhibiting Caspase-1 enzyme, as well as being modifiable for to have enhanced specificity for other Caspase enzymes.

The compounds of the present invention comprise three elements:
i) 7-member ring scaffolds;
ii) R units which are carbocyclic or heterocyclic rings attached by way of a linking unit to said scaffolds; and
iii) R¹ units which are cysteine traps attached by way of a linking unit to said scaffolds.

The novel ICE inhibitors of the present invention have been surprisingly found to satisfy the specific size, shape, and binding requirement of the Caspase-1 active site and therefore are capable of reversibly or irreversibly inactivating the enzyme Caspase-1. However, the compounds of the present invention can also be modified within the metes and bounds of the present invention to provide activity against other cysteine and serine protease enzymes as well.

The novel scaffolds of the present invention surprisingly position the selected R unit, encompassed within the description herein below, in a manner allowing for a propitious interaction between the novel compounds of the present invention and Caspase I.

The cysteine traps of the present invention can be chosen by the formulator to interact reversibly or irreversibly with the target Caspase enzyme. In general, these traps comprise a first reactive moiety and a second reactive moiety. The first reactive moiety is a carboxyl unit (or carboxyl unit precursor) which is believed to fit into a specific carboxylate docking site along the enzyme active site and in doing so bring the second reactive moiety into proximity with a cysteine amino acid residue which then reacts reversibly or irreversibly with the second reactive moiety rendering the enzyme inactive. The formulator, as described herein below, may select to reversibly or irreversibly (suicide inhibitor) inhibit the activity of the Caspase enzyme depending upon the type of cytokine related disease, treatment type, or regiment of therapy.

In addition, the formulator may use either the "bio-active" or "bio-equivalent" form of a cysteine trap depending upon the pharmaceutical composition, mode of delivery, and the like. For the purposes of the present invention, the term "bio-active" is defined herein as "the chemical form of a group, unit or moiety which interacts with the target enzyme." For the purposes of the present invention, the term "bio-equivalent" is defined herein as "a precursor form of the bio-active form of a group, unit or moiety which is readily converted to the bio-active form upon delivery into the host species being treated. The bio-equivalent form is also converted to the bio-active form prior to interaction with the targeted enzymes during in vitro testing."

For the purposes of the present invention the term "hydrocarbyl" is defined herein as any organic unit or moiety which is comprised of carbon atoms and hydrogen atoms. Included within the term hydrocarbyl are the heterocycles which are described herein below. Examples of various unsubstituted non-heterocyclic hydrocarbyl units include methyl, ethyl, propyl, pentyl, 1-butenyl, 2,2-dimethypentyl, 3-ethyl-3-methylpent-1-ynyl, 8,8-dimethylnon-3-enyl, and the like.

Included within the definition of "hydrocarbyl" are the aromatic (aryl) and non-aromatic carbocyclic rings. Non-limiting examples of substituted or unsubstituted aromatic and non-aromatic carbocyclic rings include cyclopentyl, cyclohexyl, 1-ethyl-2-methylcyclohexyl, cyclohexenyl, cycloheptanyl, cyclooctyl, octahydro-indenyl, 3,5-dimethyl-2,3,3a,4,5,6,9,9a-octahydro-1H-cyclopentacyclooctenyl, 4,6-dimethyl-1,2,3,4,4a,5,6,7,10,10a-decahydro-benzocyclooctenyl, phenyl, benzyl, 1-ethyl-2-methyl-benzyl, naphthyl, 3-methyl-1-propyl-naphthyl, indanyl, phenanthryl, 1,2,3,4-tetrahydronaphthalenyl, and the like.

The term "heterocycle" is included within the term hydrocarbyl and is described herein as a hydrocarbyl that contains one or more heteroatoms in the ring system. Heterocycle includes both aromatic (heteroaryl) and non-aromatic heterocyclic rings. Non-limiting substituted or unsubstituted examples include: pyrrolyl, 2H-pyrrolyl, pyrazolyl, 2H-imidazolyl, 1,2,3-triazolyl, 1,2,4-triazolyl, isoxazolyl, oxazoyl, 1,2,4-oxadiazolyl, 2H-pyranyl, 4H-pyranyl, 2H-pyran-2-one-yl, pyridinyl, pyridazinyl, pyrimidinyl, pyrazinyl, piperazinyl, 2H-1,3-oxazinyl, 1,4-oxazinyl, morpholinyl, azepinyl, oxepinyl, 4H-1,2-diazepinyl, benzofuranyl, indolyl, 1H-indolyl, benzoxazolyl, quinolinyl, isoquinolinyl, 2H-1,4-benzoxazinyl, pyrrolidinyl, pyrrolinyl, furanyl, thiophenyl, benzimidazolyl, 6-amino-5-oxo-3,4,4a,5,6,7,10,10a-octahydro-1H-cycloocta[c]pyran-4-carboxylic acid, 6-amino-5-oxo-1,2,3,4,4a,5,6,7,10,10a-decahydro-cycloocta[c]pyridine-4-carboxylic acid, (2-Ethoxy-5-oxo-tetrahydrofuran-3-yl)-carbamic acid allyl ester and the like.

The terms "arylene" and "heteroarylene" relate to aryl and heteroaryl units which can serve as part of a linking group, for example, units having the formula:

which represent an arylene and heteroarylene unit respectively.

The term "substituted" is used throughout the specification. The term "substituted" is defined herein as "encompassing moieties or units which can replace a hydrogen atom, two hydrogen atoms, or three hydrogen atoms of a hydrocarbyl moiety. Also substituted can include replacement of hydrogen atoms on two adjacent carbons to form a new moiety or unit." For example, a substituted unit that requires a single hydrogen atom replacement includes halogen, hydroxyl, and the like. A two hydrogen atom replacement includes carbonyl, oximino, and the like. A two hydrogen atom replacement from adjacent carbon atoms includes epoxy, and the like. Three hydrogen replacement includes cyano, and the like. The term substituted is used throughout the present specification to indicate that a. hydrocarbyl moiety, inter alia, aromatic ring, alkyl chain, can have one or more of the hydrogen atoms replaced by a substituent. When a moiety is described as "substituted" any number of the hydrogen atoms may be replaced. For example, 4-hydroxyphenyl is a "substituted aromatic carbocyclic ring", (N,N-dimethyl-5-amino)octanyl is a "substituted $C_8$ alkyl unit, 3-guanidinopropyl is a "substituted $C_3$ alkyl unit," and 2-carboxypyridinyl is a "substituted heteroaryl unit." The following are non-limiting examples of units which can serve as a replacement for hydrogen atoms when a hydrocarbyl unit is described as "substituted."

i) —[C(R$^6$)$_2$]$_p$(CH=CH)$_q$R$^6$; wherein p is from 0 to 12; q is from 0 to 12;
ii) —C(=Z)R$^6$;
iii) —C(=O)OR$^6$
iv) —C(=Z)CH=CH$_2$;
v) —C(=Z)N(R$^6$)$_2$;
vi) —C(=Z)NR$^6$N(R$^6$)$_2$;
vii) —CN;
viii) —C(=O)OM
ix) —CF$_3$, —CCl$_3$, —CBr$_3$;
x) —N(R$^6$)$_2$;
xi) -halo
xii) —NR$^6$C(=Z)R$^6$;
xiii) —NR$^6$C(=Z)N(R$^6$)$_2$;
xiv) —NR$^6$N(R$^6$)$_2$;
xv) —NHOR$^6$;
xvi) —OCF$_3$, —OCCl$_3$, —OCBr$_3$;
xvii) —NO$_2$;

xviii) —OR⁶;
xix) —NR⁶S(O)₂R⁶
xx) —NR⁶S(O)₂NR⁶
xxi) —SO₂N(R⁶)₂
xxii) —SO₂R⁶
xxiii) —SO₃M;
xxiv) —OSO₃M;
xxv) —OP(O)(OM)₂;
xxvi) —P(O)(OR⁶)₂
xxvii) —P(O)(OM)₂
xxiii) —OP(O)(OR⁶)₂
xxix) and mixtures thereof wherein R⁶ is hydrogen, substituted or unsubstituted C₁–C₂₀ linear, branched, or cyclic alkyl, C₆–C₂₀ aryl, C₇–C₂₀ alkylenearyl, and mixtures thereof; M is hydrogen, or a salt forming cation; Z is O, S, NR⁶, and mixtures thereof. Suitable salt forming cations include, sodium, lithium, potassium, calcium, magnesium, ammonium, and the like. Non-limiting examples of an alkylenearyl unit include benzyl, 2-phenylethyl, 3-phenylpropyl, 2-phenylpropyl.

The compounds of the present invention include all enatiomeric and diasteriomeric forms and pharmaceutically acceptable salts of compounds having the core scaffold represented by the formula:

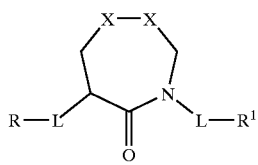

wherein each X is independently selected from:
i) —C(W)₂—;
ii) —C(O)—;
iii) —NR²—;
iv) —S—;
v) —S(O)—;
vi) —S(O)₂—;
vii) two units, one from each adjacent X unit, can be taken together to form a substituted or unsubstituted double bond having the formula —CW=CW—; wherein each W is hydrogen or a unit having the formula —[C(R³)₂]ⱼC(R²)₃, the index j is from 0 to 6.

The selection of X units, and combinations thereof, are determinative of the category into which each scaffold falls according to the present invention. For the purposes of the present invention, the following ring numbering system is used throughout the specification to identify the Interleukin 1β converting enzyme (ICE) inhibitors of the present invention when X does not comprise a ring heteroatom:

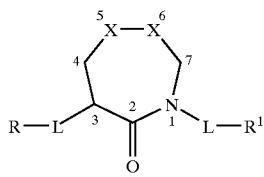

For rings comprising a heteroatom a different ring numbering system may be utilized, for example, a scaffold having the formula:

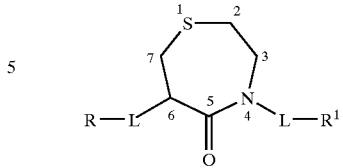

utilizes the above ring numbering system.

As it relates to the stereochemistry of the 7-member lactam ring scaffolds, the following stereochemical assignment is given for the 3-position (or other position if the X unit is a heteroatom comprising ring system) of the ring utilizing the ring numbering system described herein above. However, categories comprising X as S (sulfur) will have the "R" configuration at the 3-position, for example:

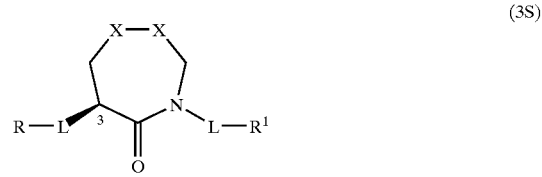
(3S)

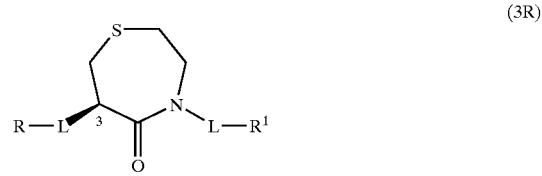
(3R)

The analogs (compounds) of the present invention are arranged in several categories predicated on the form and substitution at the X units of the parent 7-member lactam ring system to assist the formulator in applying a rational synthetic strategy for the preparation of analogs which are not expressly exampled herein. The arrangement into categories does not imply increased or decreased efficacy for any of the compositions of matter described herein.

If necessary, the analogs (compounds) of the present invention are conveniently obtained in the salt form, for example, the trifluoroacetate salt. Also, the formulator, if convenient or practicable, can prepare a pro-drug which is capable of releasing the active compound (analog) upon uptake by the host. All of these variations are encompassed within the present invention.

As stated herein above, the form of the 7-member lactam ring system indicates into which category the compounds of the present invention fall. Non-limiting examples of ring systems according to the present invention include:
i) 1,3-disubstituted 2-oxo-2,3,4,7-tetrahydro-1H-azepine scaffold having the formula:

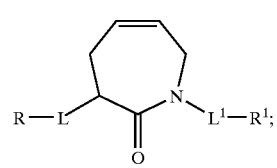

ii) 1,3,6-trisubstituted 2-oxo-2,3,4,7-tetrahydro-1H-azepine scaffold having the formula:

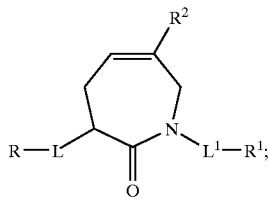

iii) 1,3,6-trisubstituted 2-oxo-2,3,4,7-tetrahydro-1H-azepine scaffold having the formula:

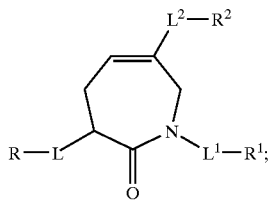

iv) 4,6-substituted-[1,4]thiazepan-5-one scaffold having the formula:

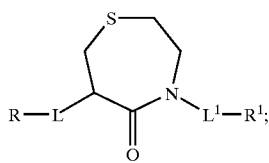

v) 4,6-disubstituted-1,1,5-trioxo-1$\lambda^6$-[1,4]-thiazepine scaffold having the formula:

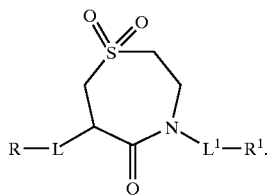

The compounds of the present invention include all enantiomeric and diasteriomeric forms and pharmaceutically acceptable salts of compounds having the core scaffold represented by the formula:

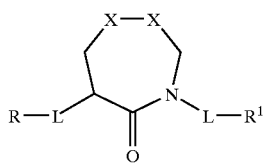

further described herein below.

R is a carbocyclic or heterocyclic ring.

The first aspect of R relates to substituted or unsubstituted carbocyclic rings.

The first embodiment of this aspect relates to substituted and unsubstituted aryl units, inter alia, phenyl and naphthyl rings. The first iteration of this embodiment relates to substituted aryl rings comprising at least one halogen atom, non-limiting examples of which includes 2-fluorophenyl, 3-fluorophenyl, 4-fluorophenyl, 3-fluoro-4-methylphenyl, 3-fluoro-4-methoxyphenyl, 3-chloro-2-methylphenyl, 3-chloro-6-methylphenyl, 3-chloro-4-methoxyphenyl, 3-chloro-4-hydroxyphenyl, 3,5-difluorophenyl, 2,6-dichlorophenyl, 2-chlorophenyl, 3-chlorophenyl, 4-chlorophenyl, 3,4-dichlorophenyl, 3,5-dichlorophenyl, 3-chloro-4-fluorophenyl, 2-bromophenyl, 3-bromophenyl, 4-bromophenyl, and the like.

A second iteration of this embodiment relates to $C_1$–$C_4$ alkyl substituted aryl units non-limiting examples of which include 2-methylphenyl, 3-methylphenyl, 4-methylphenyl, 3,5-dimethylphenyl, 2-ethylphenyl, 3-ethylphenyl, 4-ethylphenyl, 3-ethyl-4-methylphenyl 3-propylphenyl, 3-butylphenyl, and the like.

A third iteration of this embodiment relates to $C_1$–$C_4$ alkoxy substituted aryl units non-limiting examples of which include 2-methoxyphenyl, 3-methoxyphenyl, 4-methoxyphenyl, 2-ethoxyphenyl, 3-ethoxyphenyl, 4-ethoxyphenyl, 4-propoxyphenyl, 4-butoxyphenyl, 3,4,5-trimethoxy-phenyl, and the like.

A fourth iteration of this embodiment relates to amino substituted aryl units non-limiting examples of which include 3-aminonaphth-2-yl, 4-dimethylaminonaphth-1-yl, 2-aminophenyl, 3-aminophenyl, 4-aminophenyl, 3,4-dimethylaminophenyl, 4-amino-3-chlorophenyl, 4-amino-3,5-dichlorophenyl, 4-dimethylaminophenyl, 2-acetylaminophenyl, 3-acetylaminophenyl, 4-acetylaminophenyl, 4-Isobutyrylaminophenyl, 4-propionylaminophenyl, 4-butrylaminophenyl, 4-phenylacetylaminophenyl, 3,4-diacetylaminophenyl, 4-(N-acetyl-N-methylamino)-phenyl, 4-benzoylaminophenyl, and the like.

A fifth iteration of this embodiment relates to other substituted and unsubstituted aryl units non-limiting examples of which include 2-trifluoromethylphenyl, 3-trifluoromethylphenyl, 4-trifluoromethylphenyl, 4-hydroxymethyl-phenyl, naphth-1-yl, naphth-2-yl, 4-biphenyl, 4-phenoxyphenyl, 4-(3-methyl-ureido)-phenyl, 4-sulfamoylphenyl, 3-acetylphenyl, 4-acetylphenyl, 3-hydroxyphenyl, 4-hydroxyphenyl, 4-benzyloxyphenyl, 4-methanesulfonyl-phenyl, and the like.

A second embodiment of this aspect relates to R units which are non-aryl carbocyclic units, inter alia, cyclopropyl, cyclobutyl, cyclohexyl, cyclopentyl, cyclohexenyl, cyclopentenyl, and the like.

The second aspect of R relates to substituted or unsubstituted heterocyclic rings. The second embodiment of this aspect relates to other substituted and unsubstituted monocyclic heteroaryl rings, inter alia, thiophene, furanyl and pyrimidine rings. The first iteration of this embodiment relates to substituted and unsubstituted monocyclic pyridinyl systems, non-limiting examples of which include, pyridin-2-yl, pyridin-3-yl, pyridin-4-yl, 3-chloropyridin-2-yl, 4-chloropyridin-2-yl, 5-chloropyridin-2-yl, 6-chloropyridin-2-yl, 3-methylpyridin-3-yl, 4-methylpyridin-3-yl, 5-methylpyridin-3-yl, vinyl pyridin-4-yl, vinyl pyridin-3-yl, and the like.

The second iteration of this embodiment relates to other substituted and unsubstituted monocyclic heteroaryl ring systems, non-limiting examples of which include, thiophen- 3-yl, thiophen-2-yl, pyrimidin-2-yl, pyrimidin-4-yl, pyrimidin-5-yl, 2-isobutoxy-pyrimidin-4-yl, 2-isobutylaminopyrimidin-4-yl, 2-phenoxypyrimidin-4-yl, 2-ethyl-5-methyl-2H-pyrazol-3-yl, 2,4-dimethyl-thiazol-5-yl, 5-methyl-isoxazol-3-yl, 1H-imidazol-2-yl, [1,2,3]thiadiazol-5-yl, furan-2-yl, furan-3-yl, 4,5-dimethyl-2-furanyl, 5-bromo-2-furanyl, 2-phenylamino-pyrimidin-4-yl, and the like The third iteration of this embodiment relates to substituted and unsubstituted heteroaryl fused ring systems, non-limiting examples of which include quinolin-2-yl, quinolin-3-yl, quinolin-4-yl, quinolin-5-yl, quinolin-8-yl, isoquinolin-1-yl, isoquinolin-3-yl, 1,2,3,4-tetrahydro-quinolin-2-yl, 1,2,3,4-tetrahydro-quinolin-3-yl, benzofuran-2-yl, benzofuran-3-yl, benzofuran-5-yl, 1H-indol-5-yl, benzo[b]thiophen-5-yl, benzo[b]thiophen-3-yl, benzo[b]thiophen-2-yl, 3H-benzotriazol-5-yl, 1-methyl-1H-indol-2-yl, 3H-benzimidazol-5-yl, 4-methoxy-quinolin-2-yl, thieno[2,3-b]thiophen-2-yl and the like.

A second embodiment of the heterocyclic ring aspect of R relates to substituted and unsubstituted non aromatic heterocyclic rings, non-limiting examples of which include pyrrolidin-1-yl, piperidin-1-yl, piperidin-4-yl, piperazin-1-yl, and the like.

Non-limiting examples of compounds according to the present invention which comprise the above identified R units include:

Isoquinoline-1-carboxylic acid {1-[(2-hydroxy-5-oxo-tetra-hydrofuran-3-ylcarbamoyl)methyl]-2-oxo-2,3,4,7-tetrahydro-1H-azepin-3-yl} amide;

Isoquinoline-1-carboxylic acid {1-[(2-hydroxy-5-oxo-tetrahydro-furan-3-ylcarbamoyl)methyl]-6-meth-2-oxo-2,3,4,7-tetrahydro-1H-azepin-3-yl}-amide;

Isoquinoline-1-carboxylic acid {6-hydroxymethyl-1-[(2-ethoxy-5-oxo-tetrahydro-furan-3-ylcarbamoyl)-methyl]-2-oxo-2,3,4,7-tetrahydro-1H-azepin-3-yl}-amide;

Isoquinoline-1-carboxylic acid {6-hydroxymethyl-1-[(2-hydroxy-5-oxo-tetrahydro-furan-3-ylcarbamoyl)-methyl]-2-oxo-2,3,4,7-tetrahydro-1H-azepin-3-yl}-amide;

Isoquinoline-1-carboxylic acid {6-(benzylamino-methyl)-1-[(2-ethoxy-5-oxo-tetrahydro-furan-3-ylcarbamoyl)-methyl]-2-oxo-2,3,4,7-tetrahydro-1H-azepin-3-yl}-amide;

Isoquinoline-1-carboxylic acid {6-(benzylamino-methyl)-1-[(2-hydroxy-5-oxo-tetrahydro-furan-3-ylcarbamoyl)-methyl]-2-oxo-2,3,4,7-tetrahydro-1H-azepin-3-yl}-amide;

Isoquinoline-1-carboxylic acid {6-(benzenesulfonylamino-methyl)-1-[(2-hydroxy-5-oxo-tretrahydro-furan-3-ylcarbamoyl)-methyl]-2-oxo-2,3,4,7-tetrahydro-1H-azepin-3-yl}-amide;

Isoquinoline-1-carboxylic acid {6-(benzoylamino-methyl)-1-[(2-hydroxy-5-oxo-tetrahydro-furan-3-ylcarbamoyl)-methyl]-2-oxo-2,3,4,7,-tetrahydro-1H-azepin-3-yl}-amide;

N-{4-[(2-Hydroxy-5-oxo-tetrahydro-furan-3-ylcarbamoyl)-methyl]-5-oxo-1-[1,4]thiazepan-6-yl}-benzamide; and N-{4-[(2-Hydroxy-5-oxo-tetrahydro-furan-3-ylcarbamoyl)-methyl]-1,1,5-trioxo-1$\lambda^6$-[1,4]thiazepan-6-yl}-benzamide;

$R^1$ is a cysteine trap. The cysteine traps of the present invention can be in either the bio-active or the bio-equivalent form.

Without wishing to be limited by theory, the compounds of the present invention are capable of selectively inhibiting the activity of certain cysteine protease enzymes, inter alia, Caspase-1 enzyme (ICE). Although similar, the active sights of the various cysteine proteases are different enough that although the mechanism of interaction between "cysteine traps" and the various cysteine protease enzymes may be roughly equivalent, the combination of a specific cysteine trap, scaffold, and R unit according to the present invention provides enhanced specificity for certain enzymes. Caspace-1, for example, is an enzyme which is capable of acting to release Interleukin-1β which then diffuses out of the cell. Caspase-1 is believed to comprise an active site which comprises the thio (—SH) of a cysteine amino acid associated with at amino acid position 285 of the Caspase-1 enzyme. It is the thio moiety of this cysteine which reacts reversibly or irreversibly with the second reactive moiety of the cysteine traps which comprise the compounds of the present invention. It is therefore believed it is the R unit and 7-member lactam ring scaffold portion of the molecule which aligns the trap in a manner which is favorable to reacting with Caspase-1 enzyme over other cysteine proteases.

As stated herein above, the cysteine traps of the present invention may be reversible or irreversible traps. The following is a non-limiting description of cysteine traps according to the present invention.

Reversible Cysteine Traps

The first category of $R^1$ units are reversible cysteine traps, the first aspect of which relates to cyclic iterations of these traps and the bio-active and bio-equivalent embodiments thereof. These traps are referred to collectively herein as "lactol" cysteine traps whether said traps are in the bio-active form which interacts reversibly with cysteine protease enzymes or in the bio-equivalent form. These lactols have the general formula:

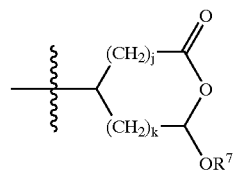

wherein $R^7$ is hydrogen (bioactive form), $C_1$–$C_4$ alkyl, substituted or unsubstituted $C_6$–$C_{10}$ aryl and alkylenearyl, inter alia, phenyl, benzyl (bio-equivalent forms) and the indices j and k are each independently 0, 1, or 2. One iteration of this aspect relates to the aspartate traps, one of which has the following bio-active forms which exist in equilibrium depending upon the medium into which they are dissolved.

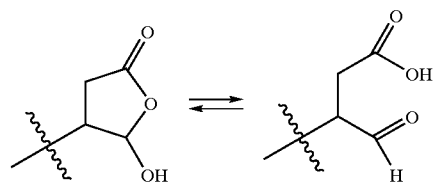

However, the bio-active form is the form which is present when enzyme inhibition occurs whether in vitro or in vivo.

An example of a bio-equivalent form of this trap has the formula:

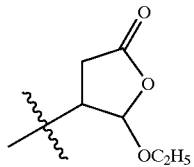

and which must be reverted to the above described bio-active form prior to interaction with the target enzyme.

Non-limiting examples of the bio-active and bio-equivalent forms of suitable cysteine traps which comprise the first aspect of $R^1$ units include:

a)
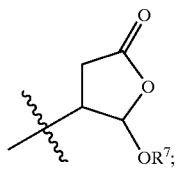

b)
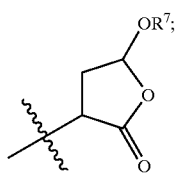

c)
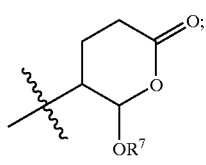

d)
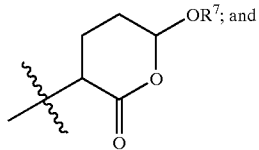

e)
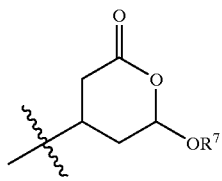

wherein $R^7$ is the same as defined herein above. As described herein below, the bio-equivalent forms of the aspartyl or glutamyl traps can be prepared according to Chapman, K. T. *Bioorganic Med. Chem. Lett.*, 2(6), 1992, pp. 613–618. included herein by reference.

A second aspect of $R^1$ units, which are reversible cysteine traps, relates to open form embodiments of said traps having the formula:

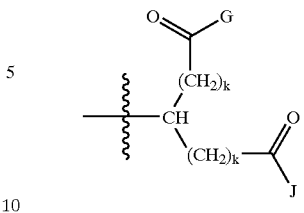

wherein G is —OH or a labile unit and J is a unit selected from the group:
  i) hydrogen;
  ii) substituted or unsubstituted aryl;
  iii) substituted or unsubstituted alkylenearyl;
  iv) substituted or unsubstituted heteroaryl;
  v) —CH$_2$N(R$^{21}$)$_2$;
  vi) —C(O)R$^{21}$;
  vii) —C(O)N(R$^{21}$)$_2$; and
  viii) —C(O)OR$^{21}$;

$R^{21}$ is hydrogen, substituted or unsubstituted aryl, substituted or unsubstituted alkylenearyl, and substituted or unsubstituted heteroaryl.

The first iteration of this second aspect encompasses reversible cysteine traps, wherein the first reactive moiety (carboxylate unit) comprises a unit having the formula:

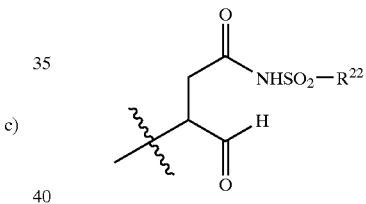

wherein $R^{22}$ is $C_1$–$C_4$ alkyl.

A second iteration of this aspect relates to cysteine traps wherein G is a —OH moiety, said traps having the general formula:

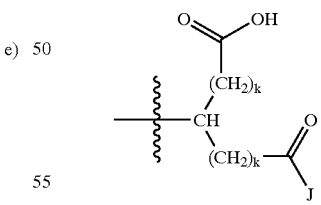

wherein J is an alkylenearyl unit having the formula —(CH$_2$)$_u$R$^{23}$; R$^{23}$ is a substituted or unsubstituted aryl unit, inter alia, phenyl, naphthyl, and the like; the index u is from 0 to 10. Non-limiting examples of suitable J units include alkylenearyl units wherein the index u is selected from the group consisting of 1, 2, 3, 4, and 5: benzyl, 2-phenylethyl, 3-phenylpropyl, 4-phenylbutyl, and 5-phenylpentyl.

A further iteration of this aspect relates to cysteine traps wherein J is a unit having the formula —N(R$^{21}$)$_2$ and one $R^{21}$ is hydrogen and the other is an alkylenearyl unit. A non-limiting example of a generic Category I scaffold coupled to a cysteine trap encompassed by this embodiment has the formula:

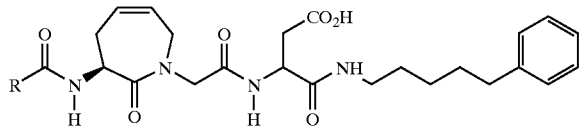

wherein R is the same as defined herein above.

A third iteration of this aspect relates to cysteine traps wherein J is an alkylenearyl unit. A non-limiting example of a generic Category I scaffold coupled to a cysteine trap encompassed by this embodiment has the formula:

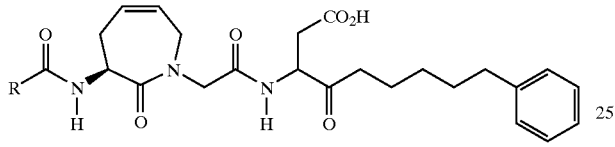

wherein R is the same as defined herein above.

A third aspect of $R^1$ units which are reversible cysteine traps relates to α,α-difluoro ketones having the formula:

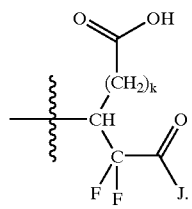

A non-limiting example of a generic Category I scaffold coupled to a α,α-difluoro ketone cysteine trap encompassed by this aspect has the formula:

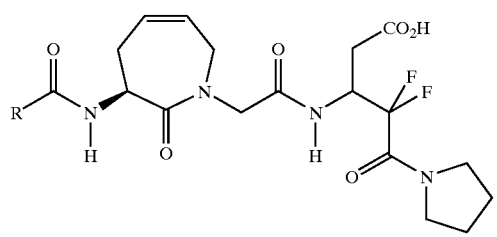

wherein R is the same as defined herein above.

The second category of $R^1$ units encompasses irreversible binding cysteine traps. These traps act in a manner described in and known throughout the prior art as "suicide" binding units because of their irreversible effect in stopping an enzyme from maintaining activity or maturing the release of cytokines. The first aspect of this category are carboxy methylene units having the formula:

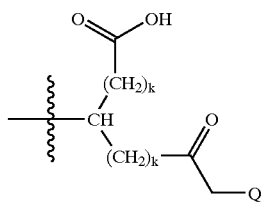

wherein Q is a leaving group selected from:
  i) substituted or unsubstituted heterocyclic or heteroaryl;
  ii) —OC(O)$R^{11}$;
  iii) —NHSO$_2$$R^{12}$;
  iv) —ONR$^{13}$C(O)$R^{13}$;
  v) halogen;
  vi) —NHC(O)OR$^{14}$;
  vii) —NHC(O)NHR$^{15}$;
  ix) —OR$^{16}$;
  x) —SR$^{17}$;
  xi) —SSR$^{18}$;
  xii) —SSO$_3$R$^{19}$; and
  xiii) —OP(O)(R$^{20}$)$_2$;

wherein $R^{11}$ is $C_6$–$C_{10}$ aryl, for example, phenyl, naphtha-1-yl; $C_7$–$C_{20}$ alkylenearyl, for example, benzyl; —NHR$^{24}$; $R^{24}$ is $C_1$–$C_4$ alkyl; $R^{12}$ is $C_1$–$C_{12}$ linear, branched, or cyclic alkyl; $R^{13}$ is hydrogen, $C_1$–$C_4$ alkyl, substituted or unsubstituted $C_6$–$C_{10}$ aryl, substituted or unsubstituted $C_7$–$C_{20}$ alkylenearyl, or two $R^{13}$ units can be taken together to form a fused or no-fused ring having from 3 to 12 atoms; $R^{14}$ is substituted or unsubstituted $C_6$–$C_{10}$ aryl or substituted or unsubstituted $C_7$–$C_{20}$ alkylenearyl; $R^{15}$ is $C_1$–$C_4$ alkyl, substituted or unsubstituted $C_6$–$C_{10}$ aryl, and substituted or unsubstituted $C_7$–$C_{20}$ alkylenearyl; $R^{16}$ is $C_1$–$C_4$ alkyl; $R^{17}$ and $R^{18}$ are substituted or unsubstituted $C_6$–$C_{10}$ aryl, and substituted or unsubstituted $C_7$–$C_{20}$ alkylenearyl; $R^{19}$ is hydrogen, $C_1$–$C_4$ alkyl, substituted or unsubstituted $C_6$–$C_{10}$ aryl, and substituted or unsubstituted $C_7$–$C_{20}$ alkylenearyl; $R^{20}$ is substituted or unsubstituted $C_6$–$C_{10}$ aryl, and substituted or unsubstituted $C_7$–$C_{20}$ alkylenearyl.

The first aspect of this category of irreversible cysteine traps relates to acyloxy ketones having the formula:

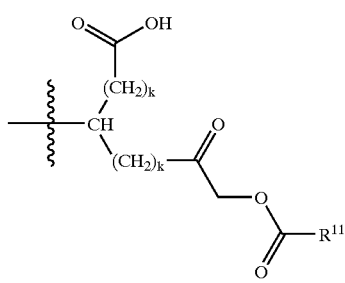

wherein $R^{11}$ is a substituted aryl unit, for example, 2,6-dimethylphenyl, 2,6-dichlorophenyl, and the like; the index k is the same as defined herein above. A non-limiting example of a generic Category I scaffold coupled to a cysteine trap encompassed by this aspect has the formula:

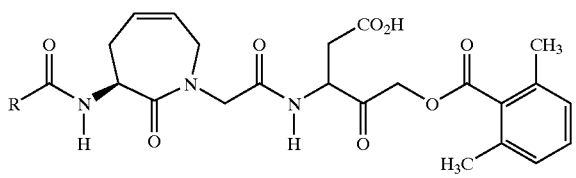

wherein R is the same as defined herein above.

A further aspect relates to cysteine traps wherein J is a unit having the formula —ONR$^{13}$C(O)R$^{13}$ wherein two R$^{13}$ units can be taken together to form a fused. A non-limiting example of a generic Category I scaffold coupled to a cysteine trap encompassed by this embodiment has the formula:

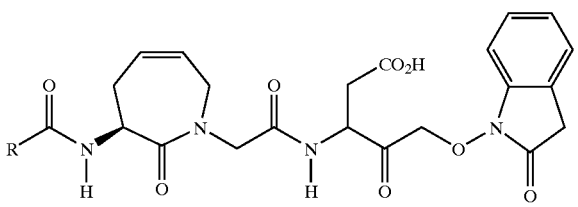

wherein R is the same as defined herein above.

A third aspect of Category II cysteine traps relates to units wherein Q is a substituted or unsubstituted heterocyclic or heteroaryl unit. A non-limiting example of a generic Category I scaffold coupled to a cysteine trap encompassed by this embodiment has the formula:

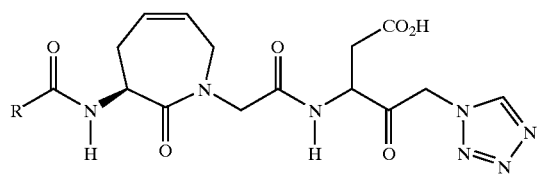

wherein R is the same as defined herein above.

Other heteroaryl units include substituted and unsubstituted isoxazolyl, thiazolyl, imidazolyl, benzoxazolyl, and isoxazolinyl. Non-limiting examples include:

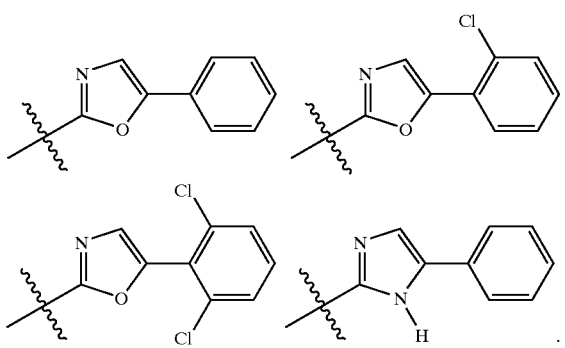

The second aspect of R$^1$ units encompassing irreversible binding cysteine traps are unsaturated compounds having the formula:

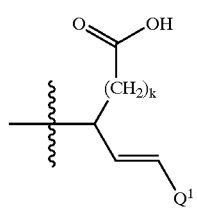

wherein Q$^1$ is a unit having the formula:
i) —C(O)R$^{24}$;
ii) —C(O)N(R$^{24}$)$_2$; or
iii) —C(O)OR$^{24}$;

the first iteration of which has the formula:

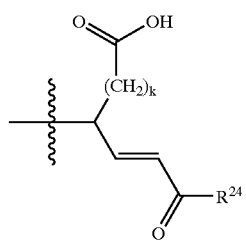

wherein R$^{24}$ is —OR$^{25}$ or —NHR$^{25}$ wherein R$^{25}$ is substituted or unsubstituted C$_6$–C$_{10}$ aryl or substituted or unsubstituted C$_7$–C$_{20}$ alkylenearyl. A non-limiting example of a generic Category II scaffold coupled to a cysteine trap encompassed by this iteration of the second aspect of R$^1$ units encompassing irreversible binding cysteine traps has the formula:

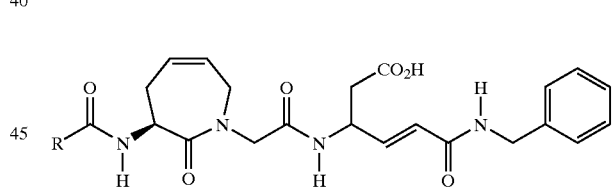

wherein R is the same as defined herein above and X is —NR$^9$ as defined herein above.

L, L$^1$, and L$^2$ are linking groups which serve to link the R, R$^1$, and R$^2$ units to the main 7-member ring scaffold, said linking groups having the formula:

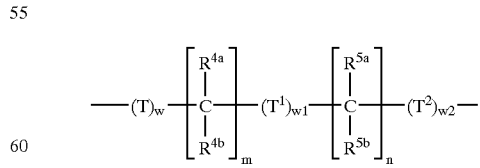

T, T$^1$, and T$^2$ are each independently selected from the group consisting of:
i) —NR$^6$—;
ii) —O—;
iii) —S(O)$_2$—;

iv) —NR$^6$S(O)$_2$—;
v) —S(O)$_2$NR$^6$—; and
vi) mixtures thereof;

w, w$^1$, and w$^2$ are each independently 0 or 1.

R$^{3a}$, R$^{3b}$, R$^{4a}$, and R$^{4b}$ are each independently
i) hydrogen;
ii) C$_1$–C$_4$ linear, branched, and cyclic alkyl;
iii) R$^{3a}$ and R$^{3b}$ or R$^{4a}$, and R$^{4b}$ can be taken together to form a carbonyl unit;
iv) two R$^{3a}$ or two R$^{3b}$ units from adjacent units or two R$^{4a}$ or two R$^{4b}$ units from adjacent units can be taken together to form a double bond; and
v) mixtures thereof;

R$^6$ is hydrogen, substituted or unsubstituted C$_1$–C$_{10}$ linear, branched, or cyclic alkyl, C$_6$–C$_{10}$ aryl, C$_7$–C$_{12}$ alkylene-aryl, and mixtures thereof; the index m is from 0 to 5; the index n is from 0 to 5; the indices w, w$^1$, and w$^2$ are each independently 0 or 1. Each value of the indices m and n represent a distinct —C(R$^{3a}$R$^{3b}$)— or —C(R$^{4a}$R$^{4b}$)— unit. As described further herein below, a first —C(R$^{3a}$R$^{3b}$)— may define a carbonyl unit in the linking unit while a second —C(R$^{3a}$R$^{3b}$)— unit may be defined as a methylene unit: —CH$_2$—.

Examples of linking units according to the present invention include L units wherein:

i) the indices n, w, and w$^2$ are each equal to 0; w$^1$ is equal to 1, T$^1$ is —NH—, m is equal to 1, R$^{3a}$ and R$^{3b}$ are taken together to form a carbonyl unit, said L unit having the formula:

—C(O)NH—;

ii) the indices m, n, and w are each equal to 0; w$^1$ and w$^2$ are equal to 1, T$^1$ is —SO$_2$— and T$^2$ is equal to —NH—, said L unit having the formula:

—SO$_2$NH—;

iii) the indices w and w$^1$ are each equal to 0; w$^2$ is equal to 1, T$^2$ is —NH—, m and n are each equal to 1, R$^{3a}$ and R$^{3b}$ are taken together to form a carbonyl unit; and R$^{4a}$ and R$^{4b}$ are taken together to form a carbonyl unit, said L unit having the formula:

—C(O)C(O)NH—;

iv) the indices m, n, w and w$^2$ are each equal to 0; w$^1$ is equal to 1, T$^1$ is —NH—, said L unit having the formula:

—NH—;

v) the indices m and w are each equal to 0; w$^1$ and w$^2$ are each equal to 1, T$^1$ and T$^2$ are each —NH—, n is equal to 1, R$^{4a}$ and R$^{4b}$ are taken together to form a carbonyl unit, said L unit having the formula:

—NHC(O)NH—;

vi) the indices m and w are each equal to 0; w$^1$ and w$^2$ are each equal to 1, T$^1$ is equal to —O—; T$^2$ is equal to —NH—, n is equal to 1, R$^{4a}$ and R$^{4b}$ are taken together to form a carbonyl unit, said L unit having the formula:

—OC(O)NH—;

vii) the indices w and w$^1$ are each equal to 0; the index w$^2$ is equal to 1; T$^2$ is equal to —NH—; m is equal to 2, each R$^{3a}$ and R$^{3b}$ unit is hydrogen; n is equal to 1, R$^{4a}$ and R$^{4b}$ are taken together to form a carbonyl unit, said L unit having the formula:

—CH$_2$CH$_2$C(O)NH—;

viii) the indices w and w$^1$ are each equal to 0; the index w$^2$ is equal to 1; T$^2$ is equal to —NH—; m is equal to 2, each R$^{3a}$ unit is hydrogen, R$^{3b}$ from the first unit and R$^{3b}$ from the second unit are taken together to form a double bond; n is equal to 1, R$^{4a}$ and R$^{4b}$ are taken together to form a carbonyl unit, said L unit having the formula:

—CH=CHC(O)NH—.

ix) the indices w and w$^2$ are each equal to 1; the index w$^1$ is equal to 0; m and n are equal to 1; T and T$^2$ are equal to —NH—; R$^{4a}$ is equal to the side chain of a d or l naturally occurring α-amino acid; R$^{4b}$ is equal to hydrogen; R$^{5a}$ and R$^{5b}$ are taken together to form a carbonyl unit, said L unit having the formula:

—NH—CH(R$^{4a}$)—C(=O)NH—.

L$^1$ units are formed in the same manner and can comprise the same or different units than L. For example, when L is —C(O)NH—, the unit L$^1$ can also be —C(O)NH—; and L$^2$ if present can be any compatible unit.

L$^2$ units are formed in the same manner and can comprise the same or different units than L and L$^1$. L$^2$ units are present when W is —(L$^2$)$_j$—R$^2$, and j is equal to 1; said units further described herein below.

The first aspect of linking units relates to the groups selected from the group consisting of:

i) —C(O)NH—;
ii) —CH$_2$C(O)NH—;
iii) —NHC(O)—:
iv) —NHC(O)NH—;
v) —C(O)C(O)—;
vi) —C(O)—;
vii) —C(O)O—;
viii) —OC(O)—;
ix) —NH—;
x) —NHS(O)$_2$—;
xi) —S(O)$_2$NH—;
xii) —S(O)$_2$—;
xii) —NHCH(R$^{4a}$)C(O)NH—;
xiv) and mixtures thereof.

The following are non-limiting iterations of the first aspect of linking units.

A first iteration of the linking units which comprise the first aspect of linking units, relates to compounds having the following scaffolds comprising L and L$^1$ units, wherein L is equal to —C(O)NH— and L$^1$ is equal to —CH$_2$C(O)NH—; for example, compounds having the formula:

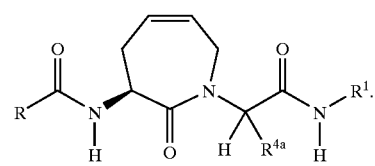

A second iteration of the linking units which comprise the first aspect of linking units, relates to compounds having the following scaffold comprising L, L$^1$, and L$^2$ units, wherein L is equal to —C(O)NH—, $L^1$ is equal to —CH$_2$C(O)NH— and $L^2$ is present (j is equal to 1); for example, a 1,3,6-trisubstituted 2-oxo-2,3,4,7-tetrahydro-1H-azepine scaffold having the formula:

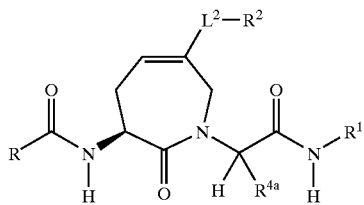

and $L^2$ can be any unit of the first aspect, inter alia, —C(O)NH—, —CH$_2$C(O)NH—; and —C(O)—

A third iteration of the linking units which comprise the first aspect of linking units, relates to compounds having the following scaffold comprising L and $L^1$ units, wherein L is equal to —NHC(O)— and $L^1$ is equal to —CH$_2$C(O)NH—; for example, compounds having the formula:

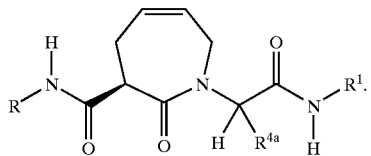

A fourth iteration of the linking units which comprise the first aspect of linking units, relates to compounds having the following scaffold comprising L and $L^1$ units, wherein L is equal to —NH— and $L^1$ is equal to —CH$_2$C(O)NH—; for example, compounds having the formula:

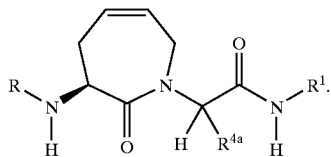

A fifth iteration of the linking units which comprise the first aspect of linking units, relates to compounds having the following scaffold comprising L and $L^1$ units, wherein L is equal to —C(O)— and $L^1$ is equal to —CH$_2$C(O)NH—; for example, compounds having the formula:

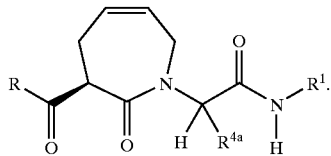

A sixth iteration of the linking units which comprise the first aspect of linking units, relates to compounds having the following scaffold comprising L and $L^1$ units, wherein L is equal to —C(O)C(O)— and $L^1$ is equal to —CH$_2$C(O)NH—; for example, compounds having the formula:

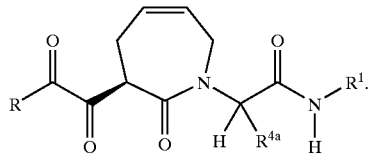

A seventh iteration of the linking units which comprise the first aspect of linking units, relates to compounds having the following scaffold comprising L and $L^1$ units, wherein L is equal to —SO$_2$NH— and $L^1$ is equal to —CH$_2$C(O)NH—; for example, compounds having the formula:

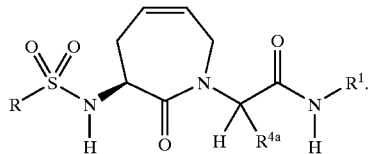

The following are examples of compounds which comprise iterations 1–7 of the second aspect of linking units as disclosed in the general figures herein above.

i) Isoquinoline-1-carboxylic acid {6-[1-(2-hydroxy-5-oxo-tetrahydro-furan-3-ylcarbamoyl)-ethyl]-7-oxo-cyclohept-3-enyl}-amide;

ii) Isoquinoline-1-carboxylic acid {4-(benzoylamino-methyl)-6-[1-(2-hydroxy-5-oxo-tetrahydro-furan-3-ylcarbamoyl)-ethyl]-7-oxo-cyclohept-3-enyl}-amide;

iii) 6-[1-(2-Hydroxy-5-oxo-tetrahydro-furan-3-ylcarbamoyl)-ethyl]-7-oxo-cyclohept-3-enecarboxylic acid isoquinolin-1-ylamide;

iv) N-(2-Hydroxy-5-oxo-tetrahydro-furan-3-yl)-2-[6-(isoquinolin-1-ylamino)-7-oxo-cyclohept-3-enyl]-propionamide;

v) N-(2-Hydroxy-5-oxo-tetrahydro-furan-3-yl)-2-[6-(isoquinoline-1-carbonyl)-7-oxo-cyclohept-3-enyl]-propionamide;

vi) N-(2-Hydroxy-5-oxo-tetrahydro-furan-3-yl)-2-[6-(2-isoquinolin-1-yl-2-oxo-acetylamino)-7-oxo-cyclohept-3-enyl]-propionamide; and vii) N-(2-Hydroxy-5-oxo-tetrahydro-furan-3-yl)-2-[6-(isoquinoline-1-sulfonylamino)-7-oxo-cyclohept-3-enyl]-propionamide; and viii) N-(2-Hydroxy-5-oxo-tetrahydro-furan-3-yl)-2-[6-(isoquinoline-1-sulfonylamino)-5-oxo-thiepan-4-yl]-propionamide.

$R^2$ units are substitutes on the 7-member ring when X is —C(W)$_2$—, or —NR$^2$—. Each $R^2$ is independently selected from the group consisting of:

i) hydrogen;
ii) a hydrocarbyl unit having the formula: —[C(R$^3$)$_2$]$_p$(CH=CH)$_q$R$^3$;
iii) —C(=Z)R$^3$;
iv) —C(=Z)AR$^3$;
v) —C(=Z)[C(R$^3$)$_2$]$_p$(CH=CH)$_q$R$^3$;
vi) —C(=Z)N(R$^3$)$_2$;
vii) —C(=Z)NR$^3$N(R$^3$)$_2$;
viii) —CN;
xix) —CF$_3$;
x) —N(R$^3$)$_2$;
xi) —NR$^3$CN;
xii) —NR$^3$C(=Z)R$^3$;

xiii) —NR³C(=Z)N(R³)₂;
xiv) —NHN(R³)₂;
xv) —NHOR³;
xvi) —NO₂;
xvii) —OR³;
xviii) —OCF₃;
xix) —F, —Cl, —Br, or —I;
xx) —SO₃M;
xxi) —OSO₃M;
xxii) —SO₂N(R³)₂;
xxiii) —SO₂R³;
xxiv) —P(O)(OR³)R³;
xxv) —P(O)(OR³)₂;
xxvi) and mixtures thereof;

each R³ is independently hydrogen, substituted or unsubstituted $C_1$–$C_{20}$ linear, branched, or cyclic alkyl, substituted or unsubstituted $C_6$–$C_{20}$ aryl, $C_1$–$C_{20}$ substituted or unsubstituted heterocyclic, $C_1$–$C_{20}$ substituted or unsubstituted heteroaryl; Z is —O—, —S—, —NR³—, and mixtures thereof; M is hydrogen, or a salt forming cation; the index p is from 0 to 12; the index q is from 0 to 12

Category II compounds of the present invention comprise a R² unit which is $C_1$–$C_4$ linear branched or cyclic alkyl.

Category III compounds of the present invention comprise an R² units which when taken together with L² form a unit —L²—R² selected from the group consisting of benzyl, —CH₂OH, —CH₂SH, —CH₂SC₆H₅ and —CH₂OC₆H₅.

Another aspect of Category III compounds of the present invention comprise an R² units which when taken together with L² form a unit —L²—R² selected from the group consisting of phenyl, 4-isopropylphenyl, 4-pentylphenyl, 2-fluorophenyl, 3-fluorophenyl, 4-fluorophenyl, 2-methylphenyl, 3-methylphenyl, 4-methylphenyl, 2-methoxyphenyl, 3-methoxyphenyl, and 4-methoxyphenyl.

A yet further aspect of Category III compounds of the present invention comprise an R² units which when taken together with L² form a unit —L²—R² selected from the group consisting of —CH₂NHCOC₆H₅, —CH₂NHCO[4-CH(CH₃)₂C₆H₄], —CH₂NHCO(4-n-pentylC₆H₄), —CH₂NHCO(2-FC₆H₄), —CH₂NHCO(3-FC₆H₄), —CH₂NHCO(4-FC₆H₄), —CH₂NHCO(2-CH₃C₆H₄), —CH₂NHCO(3-CH₃C₆H₄), —CH₂NHCO(4-CH₃C₆H₄), —CH₂NHCO(2-OCH₃C₆H₄), —CH₂NHCO(3-OCH₃C₆H₄), and —CH₂NHCO(4-OCH₃C₆H₄).

A fourth aspect of Category III compounds of the present invention comprise an R² units which when taken together with L² form a unit —L²—R² selected from the group consisting of —CH₂NHSO₂C₆H₅ —CH₂NHSO₂(4-n-pentylC₆H₄), —CH₂NHSO₂(2-FC₆H₄), —CH₂NHSO₂(3-FC₆H₄), —CH₂NHSO₂(4-FC₆H₄), —CH₂NHSO₂(2-CH₃C₆H₄), —CH₂NHSO₂(3-CH₃C₆H₄), —CH₂NHSO₂(4-CH₃C₆H₄), —CH₂NHSO₂(2-OCH₃C₆H₄), —CH₂NHSO₂(3-OCH₃C₆H₄), and —CH₂NHSO₂(4-OCH₃C₆H₄).

However, depending upon the selection of L²units or other ring variations, R² may include any iteration or embodiment described herein.

Category I interleukin-1β converting enzyme inhibitors according to the present invention relates to compounds comprising a 1,3-substituted-1,3,4,7-tetrahydroazepin-2-one ring system scaffold having the formula:

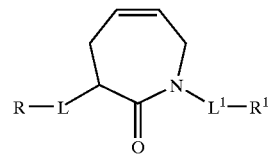

the first aspect of which comprises scaffolds having the formula:

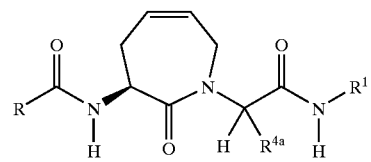

wherein R and R¹ are defined herein below in Table I.

TABLE I

| No. | R | R¹ |
|---|---|---|
| 1 | phenyl | 2-hydroxy-5-oxo-tetrahydrofuran-3-yl |
| 2 | 3-fluorophenyl | 2-hydroxy-5-oxo-tetrahydrofuran-3-yl |
| 3 | 4-fluorophenyl | 2-hydroxy-5-oxo-tetrahydrofuran-3-yl |
| 4 | 3-trifluoromethylphenyl | 2-hydroxy-5-oxo-tetrahydrofuran-3-yl |
| 5 | 4-trifluoromethylphenyl | 2-hydroxy-5-oxo-tetrahydrofuran-3-yl |
| 6 | 3-methoxyphenyl | 2-hydroxy-5-oxo-tetrahydrofuran-3-yl |
| 7 | 4-methoxyphenyl | 2-hydroxy-5-oxo-tetrahydrofuran-3-yl |
| 8 | 3-acetylphenyl | 2-hydroxy-5-oxo-tetrahydrofuran-3-yl |
| 9 | 4-acetylphenyl | 2-hydroxy-5-oxo-tetrahydrofuran-3-yl |
| 10 | 3-benzoylphenyl | 2-hydroxy-5-oxo-tetrahydrofuran-3-yl |
| 11 | 1-naphthyl | 2-hydroxy-5-oxo-tetrahydrofuran-3-yl |
| 12 | 2-naphthyl | 2-hydroxy-5-oxo-tetrahydrofuran-3-yl |
| 13 | 2-quinolinyl | 2-hydroxy-5-oxo-tetrahydrofuran-3-yl |
| 14 | 1-isoquinolinyl | 2-hydroxy-5-oxo-tetrahydrofuran-3-yl |
| 15 | 2-benzothiaphenyl | 2-hydroxy-5-oxo-tetrahydrofuran-3-yl |
| 16 | phenyl | 2-ethoxy-5-oxo-tetrahydrofuran-3-yl |
| 17 | 3-fluorophenyl | 2-ethoxy-5-oxo-tetrahydrofuran-3-yl |
| 18 | 4-fluorophenyl | 2-ethoxy-5-oxo-tetrahydrofuran-3-yl |
| 19 | 3-trifluoromethylphenyl | 2-ethoxy-5-oxo-tetrahydrofuran-3-yl |
| 20 | 4-trifluoromethylphenyl | 2-ethoxy-5-oxo-tetrahydrofuran-3-yl |
| 21 | 3-methoxyphenyl | 2-ethoxy-5-oxo-tetrahydrofuran-3-yl |
| 22 | 4-methoxyphenyl | 2-ethoxy-5-oxo-tetrahydrofuran-3-yl |
| 23 | 3-acetylphenyl | 2-ethoxy-5-oxo-tetrahydrofuran-3-yl |
| 24 | 4-acetylphenyl | 2-ethoxy-5-oxo-tetrahydrofuran-3-yl |
| 25 | 3-benzoylphenyl | 2-ethoxy-5-oxo-tetrahydrofuran-3-yl |
| 26 | 1-naphthyl | 2-ethoxy-5-oxo-tetrahydrofuran-3-yl |
| 27 | 2-naphthyl | 2-ethoxy-5-oxo-tetrahydrofuran-3-yl |
| 28 | 2-quinolinyl | 2-ethoxy-5-oxo-tetrahydrofuran-3-yl |
| 29 | 1-isoquinolinyl | 2-ethoxy-5-oxo-tetrahydrofuran-3-yl |
| 30 | 2-benzothiaphenyl | 2-ethoxy-5-oxo-tetrahydrofuran-3-yl |

The compounds of Category I can be suitably prepared by the procedure outlined herein below utilizing intermediate 3 which can be synthesized by the procedure described in Scheme I.

Scheme I

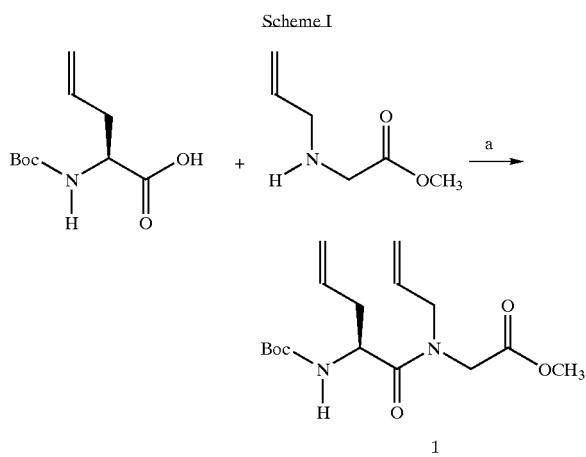

Reagents and Conditions: a) DCC, DMAP, DCM, rt 1 hr.

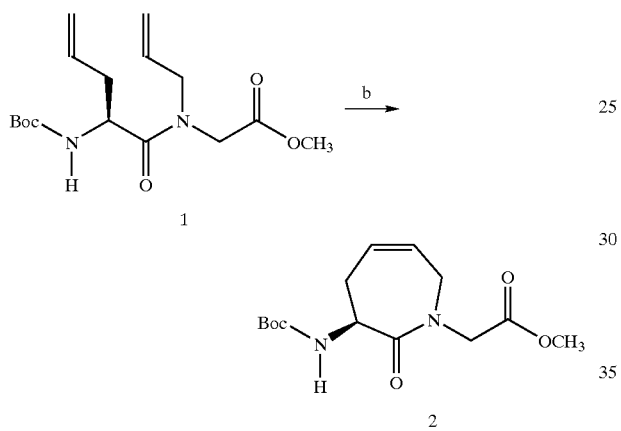

Reagents and Conditions: b) Grubbs catalyst; CH$_2$Cl$_2$, 40° C., 12–15 hrs.

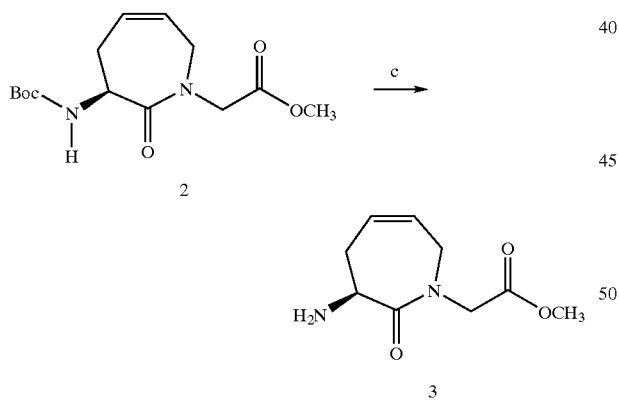

Regeants and conditions: c) TFA, CH$_2$Cl$_2$.

Preparation of [allyl-(2-tert-butoxycarbonylamino-pent-4-enoyl)amino]acetic acid methyl ester (1): A flask is charged with N-Boc-allylglycine methyl ester (0.65 g, 3 mmol), 1,3-dicyclohexylcarbodiimide (0.62 g, 3 mmol), dimethylaminopyridine (10 mg) and dichloromethane (50 mL). N-Allyl glycine methyl ester (1.29 g, 10 mmol) is dissolved in dichloromethane (20 mL) and added dropwise to the solution. The resulting reaction mixture is stirred an additional hour. The reaction was filtered to remove the precipitate and the filtrate concentrated in vacuo. The crude product is purified over silica gel to afford the desired product.

Preparation of (3-tert-butoxycarbonylamino-2-oxo-2,3,4,7-tetrahydroazepin-1-yl) acetic acid methyl ester (2): Grubbs catalyst (0.3 g) is added to a solution of [allyl-(2-tert-butoxycarbonylamino-pent-4-enoyl)amino]acetic acid methyl ester, 1, (0.815 g, 2.5 mmol) in 50 mL of CH$_2$Cl$_2$. The solution is refluxed for 12 hours after which additional catalyst (0.29 g) is added and the solution is refluxed for another 3 hours. The solution is then cooled, 1 mL of DMSO is added, and stirring continued at room temperature for an additional 12 hours. The solvent is removed in vacuo and the residue purified over silica gel to afford the desired product.

Preparation of (3-amino-2-oxo-2,3,4,7-tetrahydroazepin-1-yl) acetic acid methyl ester (3): A solution containing (3-tert-butoxycarbonylamino-2-oxo-2,3,4,7-tetrahydroazepin-1-yl) acetic acid methyl ester, 2, (0.57 g, 2.0 mmol) in 10 mL of CH$_2$Cl$_2$ is treated with 2.5 mL of wet TFA and stirred at room temperature for 30 minutes. The solution is concentrated in vacuo and treated with saturated NaHCO$_3$. Solid NaCl is added to the resulting aqueous solution and the solution is extracted with EtOAc. The organic layer was dried (MgSO$_4$) and concentrated in vacuo to afford the desired intermediate which can be used without further purification.

Intermediate 3, prepared by the procedure herein above, can be reacted with a suitable reagent which introduces the selected R unit into the compound scaffold as described in Scheme II herein below.

Scheme II

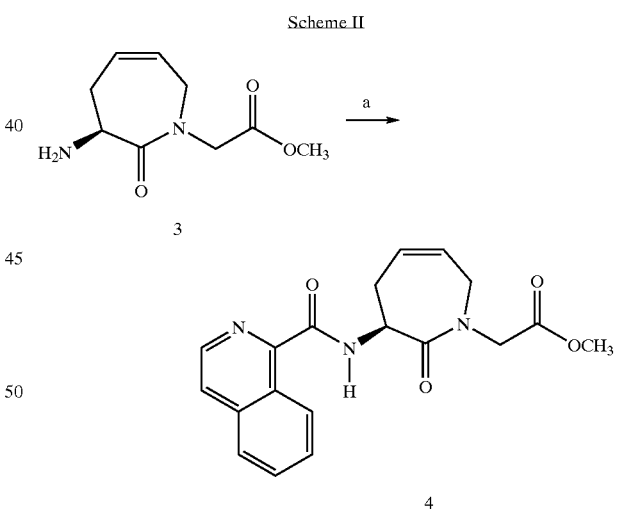

Reagents and conditions: a) RCOCl, Et$_3$N, THF.

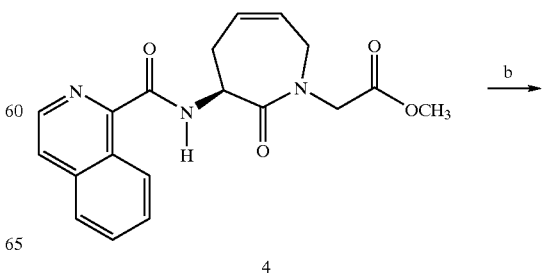

-continued

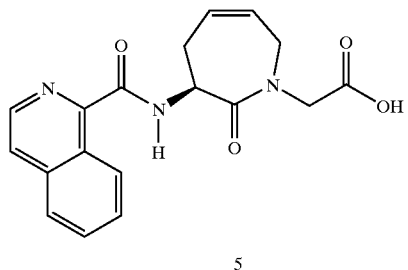

5

Reagents and conditions: b) LiOH, THF/H₂O, rt, 2.5 hrs.

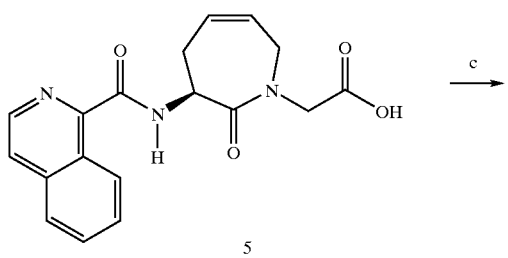

5

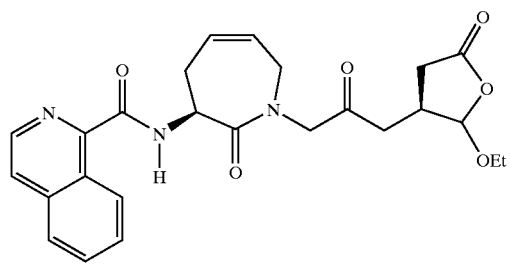

6

Reagents and conditions: c) (2-ethoxy-5-oxo-tetrahydrofurany-3-yl)-carbamic acid; N,N-dimethylbarbituric acid, (Ph₃P)₄Pd, CH₂Cl₂, EDCl, HOBt.

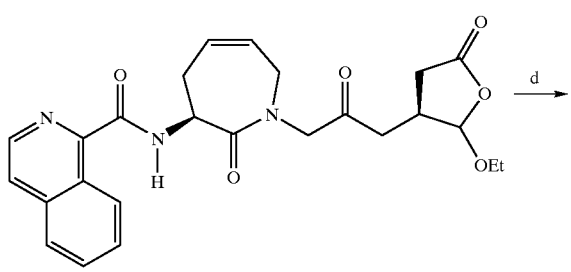

6

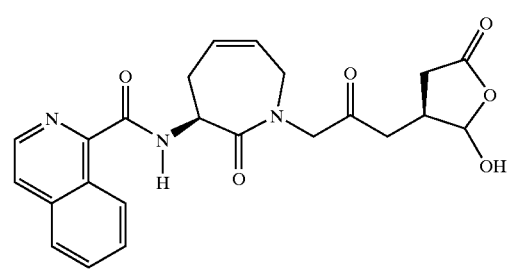

7

-continued

Reagents and conditions: d) TFA, acetonitrile/water.

EXAMPLE 1

Isoquinoline-1-carboxylic acid {1-[(2-hydroxy-5-oxo-tetra-hydrofuran-3-ylcarbamoyl)methyl]-2-oxo-2,3,4,7-tetrahydro-1H-azepin-3-yl} amide (7)

Preparation of (3-[(isoquinolin-1-carbonyl)amino]-2-oxo-2,3,4,7-tetrahydroazepin-1-yl) acetic acid ethyl ester (4): (3-amino-2-oxo-2,3,4,7-tetrahydroazepin-1-yl) acetic acid methyl ester, 3, (0.365 g, 1.68 mmol) is dissolved in 1:1 CH₂Cl₂/DMF and 1-isoquinoline-carboxylic acid (1.4 g, 8.1 mmol), 1-hydroxybenzotriazole (0.35 g, 2.6 mmol), and 1-(3-dimethyl-aminopropyl)-3-ethyl-carbodiimide hydrochloride (0.5 g, 2.6 mmol) are added. The resulting solution is stirred at room temperature for 12 hours, diluted with EtOAc, washed with saturated NaHCO₃ then brine, and dried (MgSO₄). The solvent is removed in vacuo and the resulting residue is purified over silica gel (EtOAc/hexane) to afford the desired product.

Preparation of {3-[(isoquinolin-1-carbonyl)amino]-2-oxo-2,3,4,7-tetrahydroazepin-1-yl} acetic acid (5): A solution of {3-[(isoquinolin-1-carbonyl)amino]-2-oxo- 2,3,4,7-tetrahydro-azepin-1-yl} acetic acid methyl ester, 4, (330 mg, 0.9 mmol) in 3:1 THF/H₂O is treated with excess LiOH (360 mg, 8.6 mmol) and stirred for 2.5 hours at room temperature. The solution is then acidified and the aqueous layer extracted with EtOAc. The EtOAc layer is dried (MgSO₄) and concentrated in vacuo to afford the desired product.

Preparation of isoquinoline-1-carboxylic acid {1-[(2-ethoxy-5-oxo-tetrahydrofuran-3-ylcarbamoyl)methyl]-2-oxo-2,3,4,7-tetrahydro-1H-azepin-3-yl} amide (6): A catalytic amount of Pd(Ph₃P)₄ is added to a solution of (2-ethoxy-5-oxo-tetrahydrofuran-3-yl)-carbamic acid allyl ester (338 mg, 1.48 mmol) and N,N-dimethylbarbituric acid (483 mg, 3.1 mmol) in CH₂Cl₂ (5 mL) at room temperature. The solution is stirred for 15 min then {3-[(isoquinolin-1-carbonyl)amino]-2-oxo-2,3,4,7-tetrahydro-azepin-1-yl} acetic acid, 5, (178 mg) as prepared above is added as a solution in CH₂Cl₂ (1 mL) followed by 1-hydroxybenzotriazole (416 mg, 3.1 mmol) and 1-(3-dimethyl-aminopropyl)-3-ethyl-carbodiimide hydrochloride (584 mg, 3.1 mmol). The solution is stirred for an additional 3 hours, then diluted with EtOAc, washed with saturated NaHCO₃, brine, dried (MgSO₄), and concentrated in vacuo to afford the desired product in sufficient purity to be used directly.

Preparation of isoquinoline-1-carboxylic acid {1-[(2-hydroxy-5-oxo-tetra-hydrofuran-3-ylcarbamoyl)methyl]-2-oxo-2,3,4,7-tetrahydro-1H-azepin-3-yl} amide (7): To a solution of isoquinoline-1-carboxylic acid {1-[(2-ethoxy-5-oxo-tetra-hydrofuran-3-ylcarbamoyl)methyl]-2-oxo-2,3,4,7-tetrahydro-1H-azepin-3-yl} amide, 6, from above in CH₃CN/H₂O is added trifluoroacetic acid. After stirring for 30 minutes the solution is concentrated in vacuo and the crude product purified by preparative reverse phase HPLC to afford the desired product.

The compositions which comprise Category II of the interleukin-1β converting enzyme inhibitors according to the present invention comprise a 1,3-substituted-1,3,4,7-tetrahydroazepin-2-one scaffold having the formula:

the first aspect of which comprises scaffolds having the formula:

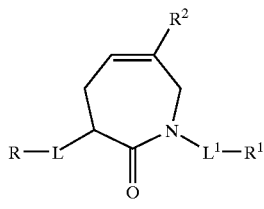

wherein R, R[1], and R[2] are defined herein below in Table II.

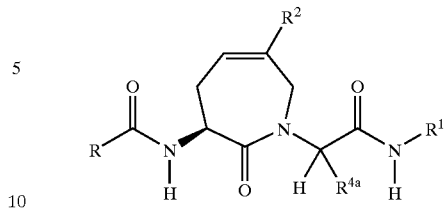

TABLE II

| No. | R | R[1] | R[2] |
|---|---|---|---|
| 31 | phenyl | 2-hydroxy-5-oxo-tetrahydrofuran-3-yl | methyl |
| 32 | 3-fluorophenyl | 2-hydroxy-5-oxo-tetrahydrofuran-3-yl | methyl |
| 33 | 4-fluorophenyl | 2-hydroxy-5-oxo-tetrahydrofuran-3-yl | methyl |
| 34 | 3-trifluoromethylphenyl | 2-hydroxy-5-oxo-tetrahydrofuran-3-yl | methyl |
| 35 | 4-trifluoromethylphenyl | 2-hydroxy-5-oxo-tetrahydrofuran-3-yl | methyl |
| 36 | 3-methoxyphenyl | 2-hydroxy-5-oxo-tetrahydrofuran-3-yl | methyl |
| 37 | 4-methoxyphenyl | 2-hydroxy-5-oxo-tetrahydrofuran-3-yl | methyl |
| 38 | 3-acetylphenyl | 2-hydroxy-5-oxo-tetrahydrofuran-3-yl | methyl |
| 39 | 4-acetylphenyl | 2-hydroxy-5-oxo-tetrahydrofuran-3-yl | methyl |
| 40 | 3-benzoylphenyl | 2-hydroxy-5-oxo-tetrahydrofuran-3-yl | methyl |
| 41 | 1-naphthyl | 2-hydroxy-5-oxo-tetrahydrofuran-3-yl | methyl |
| 42 | 2-naphthyl | 2-hydroxy-5-oxo-tetrahydrofuran-3-yl | methyl |
| 43 | 2-quinolinyl | 2-hydroxy-5-oxo-tetrahydrofuran-3-yl | methyl |
| 44 | 1-isoquinolinyl | 2-hydroxy-5-oxo-tetrahydrofuran-3-yl | methyl |
| 45 | 2-benzothiaphenyl | 2-hydroxy-5-oxo-tetrahydrofuran-3-yl | methyl |
| 46 | phenyl | 2-hydroxy-5-oxo-tetrahydrofuran-3-yl | ethyl |
| 47 | 3-fluorophenyl | 2-hydroxy-5-oxo-tetrahydrofuran-3-yl | ethyl |
| 48 | 4-fluorophenyl | 2-hydroxy-5-oxo-tetrahydrofuran-3-yl | ethyl |
| 49 | 3-trifluoromethylphenyl | 2-hydroxy-5-oxo-tetrahydrofuran-3-yl | ethyl |
| 50 | 4-trifluoromethylphenyl | 2-hydroxy-5-oxo-tetrahydrofuran-3-yl | ethyl |
| 51 | 3-methoxyphenyl | 2-hydroxy-5-oxo-tetrahydrofuran-3-yl | ethyl |
| 52 | 4-methoxyphenyl | 2-hydroxy-5-oxo-tetrahydrofuran-3-yl | ethyl |
| 53 | 3-acetylphenyl | 2-hydroxy-5-oxo-tetrahydrofuran-3-yl | ethyl |
| 54 | 4-acetylphenyl | 2-hydroxy-5-oxo-tetrahydrofuran-3-yl | ethyl |
| 55 | 3-benzoylphenyl | 2-hydroxy-5-oxo-tetrahydrofuran-3-yl | ethyl |
| 56 | 1-naphthyl | 2-hydroxy-5-oxo-tetrahydrofuran-3-yl | ethyl |
| 57 | 2-naphthyl | 2-hydroxy-5-oxo-tetrahydrofuran-3-yl | ethyl |
| 58 | 2-quinolinyl | 2-hydroxy-5-oxo-tetrahydrofuran-3-yl | ethyl |
| 59 | 1-isoquinolinyl | 2-hydroxy-5-oxo-tetrahydrofuran-3-yl | ethyl |
| 60 | 2-benzothiaphenyl | 2-hydroxy-5-oxo-tetrahydrofuran-3-yl | ethyl |
| 61 | phenyl | 2-hydroxy-5-oxo-tetrahydrofuran-3-yl | isopropyl |
| 62 | 3-fluorophenyl | 2-hydroxy-5-oxo-tetrahydrofuran-3-yl | isopropyl |
| 63 | 4-fluorophenyl | 2-hydroxy-5-oxo-tetrahydrofuran-3-yl | isopropyl |
| 64 | 3-trifluoromethylphenyl | 2-hydroxy-5-oxo-tetrahydrofuran-3-yl | isopropyl |
| 65 | 4-trifluoromethylphenyl | 2-hydroxy-5-oxo-tetrahydrofuran-3-yl | isopropyl |
| 66 | 3-methoxyphenyl | 2-hydroxy-5-oxo-tetrahydrofuran-3-yl | isopropyl |
| 67 | 4-methoxyphenyl | 2-hydroxy-5-oxo-tetrahydrofuran-3-yl | isopropyl |
| 68 | 3-acetylphenyl | 2-hydroxy-5-oxo-tetrahydrofuran-3-yl | isopropyl |
| 69 | 4-acetylphenyl | 2-hydroxy-5-oxo-tetrahydrofuran-3-yl | isopropyl |
| 70 | 3-benzoylphenyl | 2-hydroxy-5-oxo-tetrahydrofuran-3-yl | isopropyl |
| 71 | 1-naphthyl | 2-hydroxy-5-oxo-tetrahydrofuran-3-yl | isopropyl |
| 72 | 2-naphthyl | 2-hydroxy-5-oxo-tetrahydrofuran-3-yl | isopropyl |
| 73 | 2-quinolinyl | 2-hydroxy-5-oxo-tetrahydrofuran-3-yl | isopropyl |
| 74 | 1-isoquinolinyl | 2-hydroxy-5-oxo-tetrahydrofuran-3-yl | isopropyl |
| 75 | 2-benzothiaphenyl | 2-hydroxy-5-oxo-tetrahydrofuran-3-yl | isopropyl |
| 76 | phenyl | 2-ethoxy-5-oxo-tetrahydrofuran-3-yl | methyl |
| 77 | 3-fluorophenyl | 2-ethoxy-5-oxo-tetrahydrofuran-3-yl | methyl |
| 78 | 4-fluorophenyl | 2-ethoxy-5-oxo-tetrahydrofuran-3-yl | methyl |
| 79 | 3-trifluoromethylphenyl | 2-ethoxy-5-oxo-tetrahydrofuran-3-yl | methyl |
| 80 | 4-trifluoromethylphenyl | 2-ethoxy-5-oxo-tetrahydrofuran-3-yl | methyl |
| 81 | 3-methoxyphenyl | 2-ethoxy-5-oxo-tetrahydrofuran-3-yl | methyl |
| 82 | 4-methoxyphenyl | 2-ethoxy-5-oxo-tetrahydrofuran-3-yl | methyl |
| 83 | 3-acetylphenyl | 2-ethoxy-5-oxo-tetrahydrofuran-3-yl | methyl |
| 84 | 4-acetylphenyl | 2-ethoxy-5-oxo-tetrahydrofuran-3-yl | methyl |
| 85 | 3-benzoylphenyl | 2-ethoxy-5-oxo-tetrahydrofuran-3-yl | methyl |
| 86 | 1-naphthyl | 2-ethoxy-5-oxo-tetrahydrofuran-3-yl | methyl |
| 87 | 2-naphthyl | 2-ethoxy-5-oxo-tetrahydrofuran-3-yl | methyl |
| 88 | 2-quinolinyl | 2-ethoxy-5-oxo-tetrahydrofuran-3-yl | methyl |
| 89 | 1-isoquinolinyl | 2-ethoxy-5-oxo-tetrahydrofuran-3-yl | methyl |

TABLE II-continued

| No. | R | R¹ | R² |
|-----|---|----|----|
| 90 | 2-benzothiaphenyl | 2-ethoxy-5-oxo-tetrahydrofuran-3-yl | methyl |
| 91 | phenyl | 2-ethoxy-5-oxo-tetrahydrofuran-3-yl | ethyl |
| 92 | 3-fluorophenyl | 2-ethoxy-5-oxo-tetrahydrofuran-3-yl | ethyl |
| 93 | 4-fluorophenyl | 2-ethoxy-5-oxo-tetrahydrofuran-3-yl | ethyl |
| 94 | 3-trifluoromethylphenyl | 2-ethoxy-5-oxo-tetrahydrofuran-3-yl | ethyl |
| 95 | 4-trifluoromethylphenyl | 2-ethoxy-5-oxo-tetrahydrofuran-3-yl | ethyl |
| 96 | 3-methoxyphenyl | 2-ethoxy-5-oxo-tetrahydrofuran-3-yl | ethyl |
| 97 | 4-methoxyphenyl | 2-ethoxy-5-oxo-tetrahydrofuran-3-yl | ethyl |
| 98 | 3-acetylphenyl | 2-ethoxy-5-oxo-tetrahydrofuran-3-yl | ethyl |
| 99 | 4-acetylphenyl | 2-ethoxy-5-oxo-tetrahydrofuran-3-yl | ethyl |
| 100 | 3-benzoylphenyl | 2-ethoxy-5-oxo-tetrahydrofuran-3-yl | ethyl |
| 101 | 1-naphthyl | 2-ethoxy-5-oxo-tetrahydrofuran-3-yl | ethyl |
| 102 | 2-naphthyl | 2-ethoxy-5-oxo-tetrahydrofuran-3-yl | ethyl |
| 103 | 2-quinolinyl | 2-ethoxy-5-oxo-tetrahydrofuran-3-yl | ethyl |
| 104 | 1-isoquinolinyl | 2-ethoxy-5-oxo-tetrahydrofuran-3-yl | ethyl |
| 105 | 2-benzothiaphenyl | 2-ethoxy-5-oxo-tetrahydrofuran-3-yl | ethyl |
| 106 | phenyl | 2-ethoxy-5-oxo-tetrahydrofuran-3-yl | isopropyl |
| 107 | 3-fluorophenyl | 2-ethoxy-5-oxo-tetrahydrofuran-3-yl | isopropyl |
| 108 | 4-fluorophenyl | 2-ethoxy-5-oxo-tetrahydrofuran-3-yl | isopropyl |
| 109 | 3-trifluoromethylphenyl | 2-ethoxy-5-oxo-tetrahydrofuran-3-yl | isopropyl |
| 110 | 4-trifluoromethylphenyl | 2-ethoxy-5-oxo-tetrahydrofuran-3-yl | isopropyl |
| 111 | 3-methoxyphenyl | 2-ethoxy-5-oxo-tetrahydrofuran-3-yl | isopropyl |
| 112 | 4-methoxyphenyl | 2-ethoxy-5-oxo-tetrahydrofuran-3-yl | isopropyl |
| 113 | 3-acetylphenyl | 2-ethoxy-5-oxo-tetrahydrofuran-3-yl | isopropyl |
| 114 | 4-acetylphenyl | 2-ethoxy-5-oxo-tetrahydrofuran-3-yl | isopropyl |
| 115 | 3-benzoylphenyl | 2-ethoxy-5-oxo-tetrahydrofuran-3-yl | isopropyl |
| 116 | 1-naphthyl | 2-ethoxy-5-oxo-tetrahydrofuran-3-yl | isopropyl |
| 117 | 2-naphthyl | 2-ethoxy-5-oxo-tetrahydrofuran-3-yl | isopropyl |
| 118 | 2-quinolinyl | 2-ethoxy-5-oxo-tetrahydrofuran-3-yl | isopropyl |
| 119 | 1-isoquinolinyl | 2-ethoxy-5-oxo-tetrahydrofuran-3-yl | isopropyl |
| 120 | 2-benzothiaphenyl | 2-ethoxy-5-oxo-tetrahydrofuran-3-yl | isopropyl |

The ring scaffolds of this aspect of Category II of the present invention can be prepared by the procedure outlined herein below, utilizing intermediate 10, as described in Scheme III

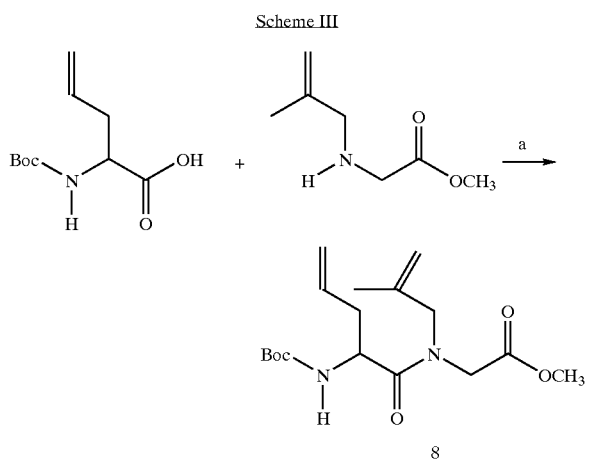

Reagents and Conditions: a) HOBt, EDCl, DCM, rt 2 hr.

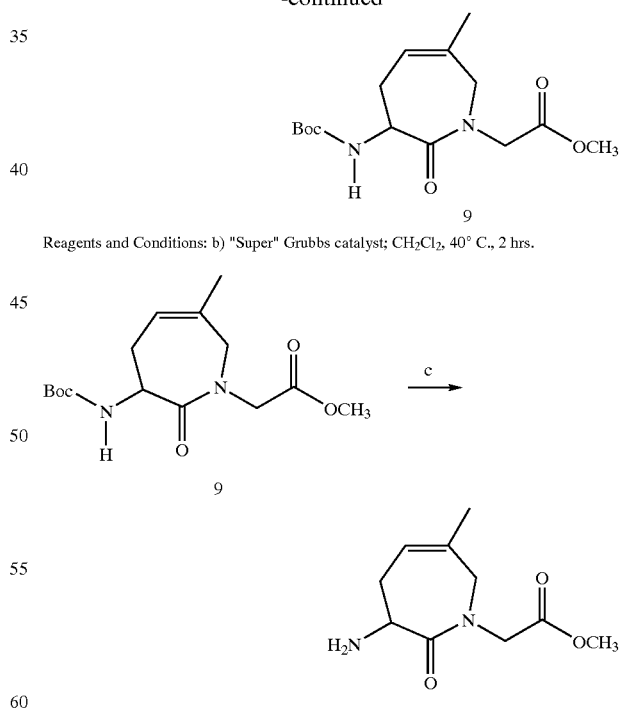

Reagents and Conditions: b) "Super" Grubbs catalyst; CH₂Cl₂, 40° C., 2 hrs.

Regeants and conditions: c) TFA, CH₂Cl₂.

The starting material, (2-methyl-allylamino)-acetic acid ethyl ester, for compound 8 can be prepared by the following method.

Ethyl bromoacetate (13.6 mL, 123 mmol) is dissolved in THF (20 mL) and cooled to 0° C. 2-Methylallyamine (18.4 g, 259 mmol) is then added. After stirring at room temperature for 5 hours, the solvent is removed in vacuo and ether added to the residue. The solid is collected by filtration and the resulting filtrate is concentrated in vacuo and purified over silica gel (ether) to afford 18 g (85% yield) of the desired product. $^1$H NMR (CDCl$_3$) δ 4.88–4.84 (d, J=10.2 2H), 4.22–4.15 (quartet, J=7.2 Hz, 2H), 3.37 (s, 2H), 3.18 (s, 2H), 1.83 (s, 1H), 1.74 (s, 3H), 1.30–1.25 (t, J=7.2 Hz, 3H); MS 158 (M+H)$^+$.

Preparation of [(2-N-Boc-aminopent-4-enoyl)-(2-methylallyl)amino] acetic acid ethyl ester (8): A solution containing (2-Methyl-allylamino)-acetic acid ethyl ester (0.507 g, 3.2 mmol), N-Boc-allylglycine (1 g, 4.8 mmol), 1-hydroxy-benzotriazole (0.87 g, 6.5 mmol), 1-(3-dimethyl-aminopropyl)-3-ethyl-carbodiimide hydrochloride (1.24 g, 6.5 mmol) and CH$_2$Cl$_2$ (20 mL) is stirred at room temperature for 2 hours. The reaction is then diluted with EtOAc, washed with saturated NaHCO$_3$, saturated NaCl, and dried (Na$_2$SO$_4$). The solvent is removed in vacuo and the crude product purified over silica gel (EtOAc/hexane) to afford 0.9 g (79% yield) of the desired product. $^1$H NMR (CDCl$_3$) δ 5.87–5.71 (m, 1H), 5.32–5.29 (d, J=8.7 Hz, 1H), 5.23–4.81 (m, 4H), 4.73–4.66 (m, 1H), 4.52–3.81 (m, 6H), 2.59–2.50 (m, 1H), 2.43–2.34 (m, 1H), 1.75 (s, 3H), 1.44 (s, 9H), 1.33–1.23 (m, 3H); MS 355 (M+H)$^+$.

Preparation of (3-N-Boc-amino-6-methyl-2-oxo-2,3,4,7-tetrahydro-azepin-1-yl)-acetic acid ethyl ester (9): Super Grubbs catalyst (tricyclohexylphosphine [1,3-bis(2,4,6-trimethylphenyl)-4,5-dihydroimidazol-2-ylidene benzylidene] ruthenium (IV) dichloride) (0.15 g) is added to a solution of [(2-N-Boc-aminopent-4-enoyl)-(2-methylallyl)amino] acetic acid ethyl ester, 8, (0.45 g, 1.3 mmol) in CH$_2$Cl$_2$ (20 mL). After the solution is refluxed for 2 hours, DMSO (0.2 mL) is added and stirring continued for 12 hours. After removing the solvent in vacuo the crude product is purified over silica gel (EtOAc/hexane) to afford 0.32 g (78% yield) of the desired product. $^1$H NMR (CDCl$_3$) δ 5.72–5.70 (d, J=6.6 Hz, 1H), 5.04–5.39 (m, 1H), 4.86–4.79 (m, 1H), 4.57–4.50 (d, J=18.6 Hz, 4.26–4.20 (d, J=17.7 Hz, 1H), 4.16–3.99 (m, 3H), 3.13–3.07 (d, J=17.7 Hz, 1H), 2.53–2.47 (d, J=18 Hz, 1H), 2.20–2.01 (m, 1H), 1.66 (s, 3H), 1.36 (s, 9H), 1.22–1.16 (m, 3H); $^{13}$C NMR (CDCl$_3$) 173.0, 169.1, 155.1, 131.6, 131.6, 123.3, 79.6, 61.5, 52.1, 50.6, 50.3, 33.2, 28.4, 24.7, 14.2; MS 327 (M+H)$^+$.

Preparation of (3-amino-6-methyl-2-oxo-2,3,4,7-tetrahydroazepin-1-yl}-acetic acid ethyl ester (10): A solution containing (3-N-Boc-amino-6-methyl-2-oxo-2,3,4,7-tetrahydro-azepin-1-yl)-acetic acid ethyl ester, 9, (0.2 g, 0.06 mmol) in CH$_2$Cl$_2$ (10 mL) is treated with wet TFA (2.5 mL) and stirred at room temperature for 30 min. The solution is then concentrated in vacuo and treated NaHCO$_3$. The resulting aqueous solution is further saturated with solid NaCl and extracted with EtOAc. The organic layer is dried (Na$_2$SO$_4$) and the solvent removed in vacuo to afford the desired product which is used without further purification.

Intermediate 10, prepared by the procedure herein above, can be reacted with a suitable reagent which introduces the selected R unit into the compound scaffold as described in Scheme II herein below.

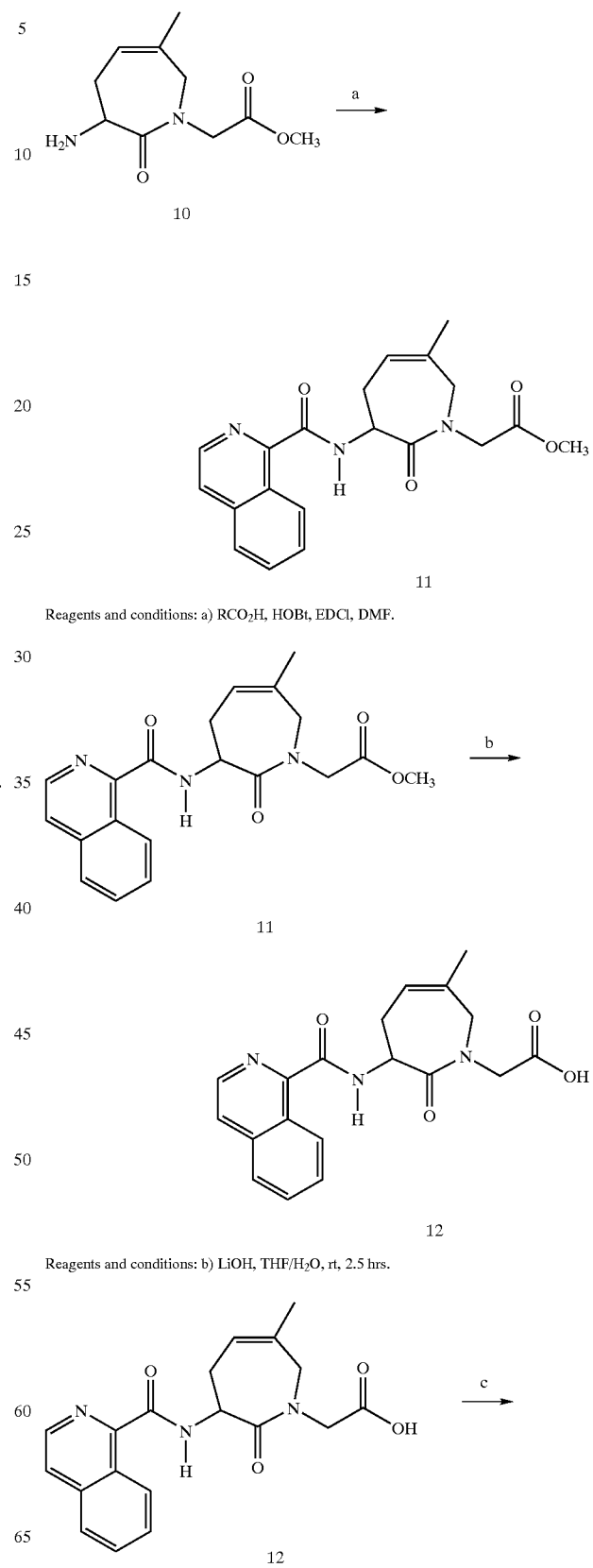

Scheme IV

10

Reagents and conditions: a) RCO$_2$H, HOBt, EDCl, DMF.

11

11

Reagents and conditions: b) LiOH, THF/H$_2$O, rt, 2.5 hrs.

12

12

-continued

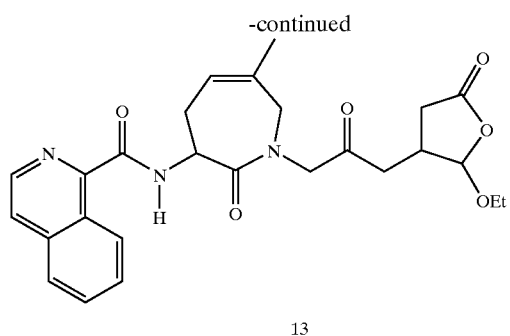

13

Reagents and conditions: c) (2-Ethoxy-5-oxo-tetrahydrofurany-3-yl)-carbamic acid; N,N-dimethylbarbituric acid, (Ph₃P)₄Pd, CH₂Cl₂, EDCl, HOBt

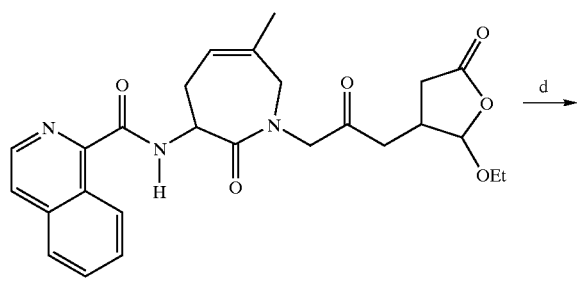

13

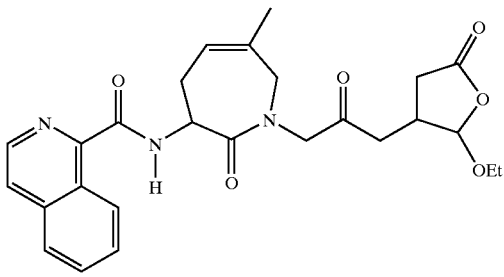

14

Reagents and conditions: d) TFA, acetonitrile/water.

EXAMPLE 2

Isoquinoline-1-carboxylic acid {1-[(2-hydroxy-5-oxo-tetrahydro-furan-3-ylcarbamoyl)methyl]-6-meth-2-oxo-2,3,4,7-tetrahydro-1H-azepin-3-yl}-amide (14)

Preparation of {3-[(isoquinoline-1-carbonyl)amino]-6-methyl-2-oxo-2,3,4,7-tetrahydroazepin-1-yl}-acetic acid ethyl ester (11): The crude (3-amino-6-methyl-2-oxo-2,3,4,7-tetrahydroazepin-1-yl}-acetic acid ethyl ester, 10, obtained in the previous step is dissolved in 6 mL of 1:1 DMF:CH₂Cl₂ and treated with 1-isoquinolinecarboxylic acid (0.24 g, 1.2 mmol), 1-hydroxybenzotriazole (0.23 g, 1.5 mmol), and 1-(3-dimethyl-aminopropyl)-3-ethyl-carbodiimide hydrochloride (0.32 g, 1.5 mmol). The solution is stirred for 1 hour at room temperature, diluted with EtOAc, washed with saturated NaHCO₃, saturated NaCl, and dried ($Na_2SO_4$). The solvent is removed in vacuo and the crude isolate is purified by HPLC to afford 70 mg (30% yield) of the desired product. ¹H NMR (CDCl₃) δ 9.51–9.48 (d, J=8.1 Hz, 1H), 9.22–9.20 (d, J=6.9 Hz, 1H), 8.51–8.49 (d, J=5.4 Hz, 1H), 7.84–7.77 (m, 2H), 7.72–7.63 (m, 2H), 5.57 (bs, 1H), 5.48–5.40 (m, 1H), 4.775–4.715 (d, J=18 Hz, 1H), 4.24–4.19 (q, d, J=15.3, 7.5 Hz, 3H), 3.27–3.21 (d, J=18 Hz, 1H), 2.86–2.81 (d, J=16.5 Hz, 1H), 2.45–2.36 (d, d, J=15, 12.6 Hz, 1H), 1.79 (s, 3H), 1.30–1.25 (t, J=7.5 Hz, 3H); ¹³C (CDCl₃) 172.8, 169.2, 165.6, 148.2, 140.8, 137.5, 131.8, 130.5, 128.7, 127.7, 127.0, 124.5, 123.4, 61.6, 52.3, 50.8, 49.6, 32.6, 25.0, 14.3; MS 382 (M+H)⁺.

Preparation of {3-[(isoquinoline-1-carbonyl)amino]-6-methyl-2-oxo-2,3,4,7-tetrahydroazepin-1-yl}-acetic acid (12): A solution containing {3-[(isoquinoline-1-carbonyl)amino]-6-methyl-2-oxo-2,3,4,7-tetrahydroazepin-1-yl}-acetic acid ethyl ester, 11, (70 mg, 0.28 mmol) in 3 mL of 3:1 THF/H₂O is treated with excess LiOH and stirred for 2.5 hours at room temperature. The solution is acidified and extracted with EtOAc. The EtOAc layer is dried (Na₂SO₄) and concentrated in vacuo to afford the desired product which is used without further purification.

Preparation of isoquinoline-1-carboxylic acid {1-[(2-ethoxy-5-oxo-tetrahydro-furan-3-ylcarbamoyl)methyl]-6-meth-2-oxo-2,3,4,7-tetrahydro-1H-azepin-3-yl}-amide (13): A catalytic amount of Pd(Ph₃P)₄ is added to a solution of (2-ethoxy-5-oxo-furan-3-yl)-carbamic acid allyl ester (118 mg, 0.51 mmol) and N,N-dimethylbarbituric acid (194 mg, 1.24 mmol) in CH₂Cl₂ (5 mL) at room temperature. The solution is stirred at room temperature for 15 min after which crude {3-[(isoquinoline-1-carbonyl)amino]-6-methyl-2-oxo-2,3,4,7-tetrahydroazepin-1-yl}-acetic acid, 12, prepared in the previous step is added as a solution in 2 mL of 1:1 CH₂Cl₂/DMF. 1-Hydroxybenzotriazole (64 mg, 0.48 mmol) and 1-(3-dimethyl-aminopropyl)-3-ethyl-carbodiimide hydrochloride (91 mg, 0.48 mmol) are then added. The solution is stirred for 5 hours, diluted with EtOAc, washed with saturated NaHCO₃ and brine, dried (Na₂SO₄), and concentrated in vacuo to afford the crude product which is purified over silica gel and used directly for the next step.

Preparation of isoquinoline-1-carboxylic acid {1-[(2-hydroxy-5-oxo-tetrahydro-furan-3-ylcarbamoyl)methyl]-6-meth-2-oxo-2,3,4,7-tetrahydro-1H-azepin-3-yl}-amide (14): The isolated isoquinoline-1-carboxylic acid {1-[(2-ethoxy-5-oxo-tetrahydro-furan-3-ylcarbamoyl)methyl]-6-meth-2-oxo-2,3,4,7-tetrahydro-1H-azepin-3-yl}-amide, 13, from the previous step is treated with TFA in CH₃CN/H₂O. Work-up for neutral followed by purification via reverse phase HPLC affords 17 mg (20% yield) of the desired Interleukin 1β converting enzyme inhibitor. ¹H NMR (CD₃OD) δ 9.24–9.21 (d, J=8.7 Hz, 1H), 8.55–8.53 (d, J=6 Hz, 1H), 8.01–7.96 (d, d, J=8.7, 6.3 Hz, 2H), 7.84–7.70 (m, 3H), 5.61 (bs, 1H), 5.53–5.47 (d, d, J=11.7, 3.6 Hz, 1H), 4.84–4.78 (d, J=18 Hz, 1H), 4.68–4.62 (m, 1H), 4.37–4.17 (m, 3H), 3.48–3.39 (m, 1H), 2.81–2.65 (m, 3H), 2.59–2.40 (m, 3H), 1.86 (s, 3H); MS 453 (M+H)⁺.

The compounds which comprise Category III of the interleukin-1β converting enzyme inhibitors according to the present invention relate to compounds comprising a 1,3,6-tri-substituted-1,3,4,7-tetrahydroazepine-2-one scaffold having the formula;

the first aspect of which comprises scaffolds having the formula:

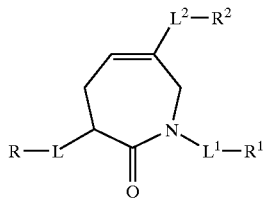

wherein R, R$^1$, L$^2$ and R$^2$ are described herein below in Table III.

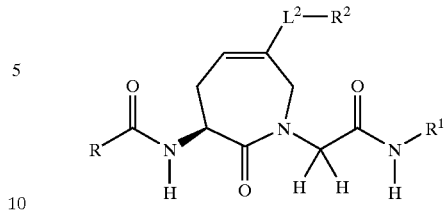

TABLE III

| No. | R | R$^1$ | —L$^2$—R$^2$ |
|---|---|---|---|
| 121 | phenyl | 2-hydroxy-5-oxo-tetrahydrofuran-3-yl | benzyl |
| 122 | 3-fluorophenyl | 2-hydroxy-5-oxo-tetrahydrofuran-3-yl | benzyl |
| 123 | 4-fluorophenyl | 2-hydroxy-5-oxo-tetrahydrofuran-3-yl | benzyl |
| 124 | 3-trifluoromethylphenyl | 2-hydroxy-5-oxo-tetrahydrofuran-3-yl | benzyl |
| 125 | 4-trifluoromethylphenyl | 2-hydroxy-5-oxo-tetrahydrofuran-3-yl | benzyl |
| 126 | 3-methoxyphenyl | 2-hydroxy-5-oxo-tetrahydrofuran-3-yl | benzyl |
| 127 | 4-methoxyphenyl | 2-hydroxy-5-oxo-tetrahydrofuran-3-yl | benzyl |
| 128 | 3-acetylphenyl | 2-hydroxy-5-oxo-tetrahydrofuran-3-yl | benzyl |
| 129 | 4-acetylphenyl | 2-hydroxy-5-oxo-tetrahydrofuran-3-yl | benzyl |
| 130 | 3-benzoylphenyl | 2-hydroxy-5-oxo-tetrahydrofuran-3-yl | benzyl |
| 131 | 1-naphthyl | 2-hydroxy-5-oxo-tetrahydrofuran-3-yl | benzyl |
| 132 | 2-naphthyl | 2-hydroxy-5-oxo-tetrahydrofuran-3-yl | benzyl |
| 133 | 2-quinolinyl | 2-hydroxy-5-oxo-tetrahydrofuran-3-yl | benzyl |
| 134 | 1-isoquinolinyl | 2-hydroxy-5-oxo-tetrahydrofuran-3-yl | benzyl |
| 135 | 2-benzothiaphenyl | 2-hydroxy-5-oxo-tetrahydrofuran-3-yl | benzyl |
| 136 | phenyl | 2-hydroxy-5-oxo-tetrahydrofuran-3-yl | —CH$_2$OH |
| 137 | 3-fluorophenyl | 2-hydroxy-5-oxo-tetrahydrofuran-3-yl | —CH$_2$OH |
| 138 | 4-fluorophenyl | 2-hydroxy-5-oxo-tetrahydrofuran-3-yl | —CH$_2$OH |
| 139 | 3-trifluoromethylphenyl | 2-hydroxy-5-oxo-tetrahydrofuran-3-yl | —CH$_2$OH |
| 140 | 4-trifluoromethylphenyl | 2-hydroxy-5-oxo-tetrahydrofuran-3-yl | —CH$_2$OH |
| 141 | 3-methoxyphenyl | 2-hydroxy-5-oxo-tetrahydrofuran-3-yl | —CH$_2$OH |
| 142 | 4-methoxyphenyl | 2-hydroxy-5-oxo-tetrahydrofuran-3-yl | —CH$_2$OH |
| 143 | 3-acetylphenyl | 2-hydroxy-5-oxo-tetrahydrofuran-3-yl | —CH$_2$OH |
| 144 | 4-acetylphenyl | 2-hydroxy-5-oxo-tetrahydrofuran-3-yl | —CH$_2$OH |
| 145 | 3-benzoylphenyl | 2-hydroxy-5-oxo-tetrahydrofuran-3-yl | —CH$_2$OH |
| 146 | 1-naphthyl | 2-hydroxy-5-oxo-tetrahydrofuran-3-yl | —CH$_2$OH |
| 147 | 2-naphthyl | 2-hydroxy-5-oxo-tetrahydrofuran-3-yl | —CH$_2$OH |
| 148 | 2-quinolinyl | 2-hydroxy-5-oxo-tetrahydrofuran-3-yl | —CH$_2$OH |
| 149 | 1-isoquinolinyl | 2-hydroxy-5-oxo-tetrahydrofuran-3-yl | —CH$_2$OH |
| 150 | 2-benzothiaphenyl | 2-hydroxy-5-oxo-tetrahydrofuran-3-yl | —CH$_2$OH |
| 151 | phenyl | 2-hydroxy-5-oxo-tetrahydrofuran-3-yl | —CH$_2$SH |
| 152 | 3-fluorophenyl | 2-hydroxy-5-oxo-tetrahydrofuran-3-yl | —CH$_2$SH |
| 153 | 4-fluorophenyl | 2-hydroxy-5-oxo-tetrahydrofuran-3-yl | —CH$_2$SH |
| 154 | 3-trifluoromethylphenyl | 2-hydroxy-5-oxo-tetrahydrofuran-3-yl | —CH$_2$SH |
| 155 | 4-trifluoromethylphenyl | 2-hydroxy-5-oxo-tetrahydrofuran-3-yl | —CH$_2$SH |
| 156 | 3-methoxyphenyl | 2-hydroxy-5-oxo-tetrahydrofuran-3-yl | —CH$_2$SH |
| 157 | 4-methoxyphenyl | 2-hydroxy-5-oxo-tetrahydrofuran-3-yl | —CH$_2$SH |
| 158 | 3-acetylphenyl | 2-hydroxy-5-oxo-tetrahydrofuran-3-yl | —CH$_2$SH |
| 159 | 4-acetylphenyl | 2-hydroxy-5-oxo-tetrahydrofuran-3-yl | —CH$_2$SH |
| 160 | 3-benzoylphenyl | 2-hydroxy-5-oxo-tetrahydrofuran-3-yl | —CH$_2$SH |
| 161 | 1-naphthyl | 2-hydroxy-5-oxo-tetrahydrofuran-3-yl | —CH$_2$SH |
| 162 | 2-naphthyl | 2-hydroxy-5-oxo-tetrahydrofuran-3-yl | —CH$_2$SH |
| 163 | 2-quinolinyl | 2-hydroxy-5-oxo-tetrahydrofuran-3-yl | —CH$_2$SH |
| 164 | 1-isoquinolinyl | 2-hydroxy-5-oxo-tetrahydrofuran-3-yl | —CH$_2$SH |
| 165 | 2-benzothiaphenyl | 2-hydroxy-5-oxo-tetrahydrofuran-3-yl | —CH$_2$SH |
| 166 | phenyl | 2-hydroxy-5-oxo-tetrahydrofuran-3-yl | —CH$_2$SC$_6$H$_5$ |
| 167 | 3-fluorophenyl | 2-hydroxy-5-oxo-tetrahydrofuran-3-yl | —CH$_2$SC$_6$H$_5$ |
| 168 | 4-fluorophenyl | 2-hydroxy-5-oxo-tetrahydrofuran-3-yl | —CH$_2$SC$_6$H$_5$ |
| 169 | 3-trifluoromethylphenyl | 2-hydroxy-5-oxo-tetrahydrofuran-3-yl | —CH$_2$SC$_6$H$_5$ |
| 170 | 4-trifluoromethylphenyl | 2-hydroxy-5-oxo-tetrahydrofuran-3-yl | —CH$_2$SC$_6$H$_5$ |
| 171 | 3-methoxyphenyl | 2-hydroxy-5-oxo-tetrahydrofuran-3-yl | —CH$_2$SC$_6$H$_5$ |
| 172 | 4-methoxyphenyl | 2-hydroxy-5-oxo-tetrahydrofuran-3-yl | —CH$_2$SC$_6$H$_5$ |
| 173 | 3-acetylphenyl | 2-hydroxy-5-oxo-tetrahydrofuran-3-yl | —CH$_2$SC$_6$H$_5$ |
| 174 | 4-acetylphenyl | 2-hydroxy-5-oxo-tetrahydrofuran-3-yl | —CH$_2$SC$_6$H$_5$ |
| 175 | 3-benzoylphenyl | 2-hydroxy-5-oxo-tetrahydrofuran-3-yl | —CH$_2$SC$_6$H$_5$ |
| 176 | 1-naphthyl | 2-hydroxy-5-oxo-tetrahydrofuran-3-yl | —CH$_2$SC$_6$H$_5$ |
| 177 | 2-naphthyl | 2-hydroxy-5-oxo-tetrahydrofuran-3-yl | —CH$_2$SC$_6$H$_5$ |
| 178 | 2-quinolinyl | 2-hydroxy-5-oxo-tetrahydrofuran-3-yl | —CH$_2$SC$_6$H$_5$ |
| 179 | 1-isoquinolinyl | 2-hydroxy-5-oxo-tetrahydrofuran-3-yl | —CH$_2$SC$_6$H$_5$ |

TABLE III-continued

| No. | R | R¹ | —L²—R² |
|---|---|---|---|
| 180 | 2-benzothiaphenyl | 2-hydroxy-5-oxo-tetrahydrofuran-3-yl | —CH₂SC₆H₅ |
| 181 | phenyl | 2-ethoxy-5-oxo-tetrahydrofuran-3-yl | benzyl |
| 182 | 3-fluorophenyl | 2-ethoxy-5-oxo-tetrahydrofuran-3-yl | benzyl |
| 183 | 4-fluorophenyl | 2-ethoxy-5-oxo-tetrahydrofuran-3-yl | benzyl |
| 184 | 3-trifluoromethylphenyl | 2-ethoxy-5-oxo-tetrahydrofuran-3-yl | benzyl |
| 185 | 4-trifluoromethylphenyl | 2-ethoxy-5-oxo-tetrahydrofuran-3-yl | benzyl |
| 186 | 3-methoxyphenyl | 2-ethoxy-5-oxo-tetrahydrofuran-3-yl | benzyl |
| 187 | 4-methoxyphenyl | 2-ethoxy-5-oxo-tetrahydrofuran-3-yl | benzyl |
| 188 | 3-acetylphenyl | 2-ethoxy-5-oxo-tetrahydrofuran-3-yl | benzyl |
| 189 | 4-acetylphenyl | 2-ethoxy-5-oxo-tetrahydrofuran-3-yl | benzyl |
| 190 | 3-benzoylphenyl | 2-ethoxy-5-oxo-tetrahydrofuran-3-yl | benzyl |
| 191 | 1-naphthyl | 2-ethoxy-5-oxo-tetrahydrofuran-3-yl | benzyl |
| 192 | 2-naphthyl | 2-ethoxy-5-oxo-tetrahydrofuran-3-yl | benzyl |
| 193 | 2-quinolinyl | 2-ethoxy-5-oxo-tetrahydrofuran-3-yl | benzyl |
| 194 | 1-isoquinolinyl | 2-ethoxy-5-oxo-tetrahydrofuran-3-yl | benzyl |
| 195 | 2-benzothiaphenyl | 2-ethoxy-5-oxo-tetrahydrofuran-3-yl | benzyl |
| 196 | phenyl | 2-ethoxy-5-oxo-tetrahydrofuran-3-yl | —CH₂OH |
| 197 | 3-fluorophenyl | 2-ethoxy-5-oxo-tetrahydrofuran-3-yl | —CH₂OH |
| 198 | 4-fluorophenyl | 2-ethoxy-5-oxo-tetrahydrofuran-3-yl | —CH₂OH |
| 199 | 3-trifluoromethylphenyl | 2-ethoxy-5-oxo-tetrahydrofuran-3-yl | —CH₂OH |
| 200 | 4-trifluoromethylphenyl | 2-ethoxy-5-oxo-tetrahydrofuran-3-yl | —CH₂OH |
| 201 | 3-methoxyphenyl | 2-ethoxy-5-oxo-tetrahydrofuran-3-yl | —CH₂OH |
| 202 | 4-methoxyphenyl | 2-ethoxy-5-oxo-tetrahydrofuran-3-yl | —CH₂OH |
| 203 | 3-acetylphenyl | 2-ethoxy-5-oxo-tetrahydrofuran-3-yl | —CH₂OH |
| 204 | 4-acetylphenyl | 2-ethoxy-5-oxo-tetrahydrofuran-3-yl | —CH₂OH |
| 205 | 3-benzoylphenyl | 2-ethoxy-5-oxo-tetrahydrofuran-3-yl | —CH₂OH |
| 206 | 1-naphthyl | 2-ethoxy-5-oxo-tetrahydrofuran-3-yl | —CH₂OH |
| 207 | 2-naphthyl | 2-ethoxy-5-oxo-tetrahydrofuran-3-yl | —CH₂OH |
| 208 | 2-quinolinyl | 2-ethoxy-5-oxo-tetrahydrofuran-3-yl | —CH₂OH |
| 209 | 1-isoquinolinyl | 2-ethoxy-5-oxo-tetrahydrofuran-3-yl | —CH₂OH |
| 210 | 2-benzothiaphenyl | 2-ethoxy-5-oxo-tetrahydrofuran-3-yl | —CH₂OH |
| 211 | phenyl | 2-ethoxy-5-oxo-tetrahydrofuran-3-yl | —CH₂SH |
| 212 | 3-fluorophenyl | 2-ethoxy-5-oxo-tetrahydrofuran-3-yl | —CH₂SH |
| 213 | 4-fluorophenyl | 2-ethoxy-5-oxo-tetrahydrofuran-3-yl | —CH₂SH |
| 214 | 3-trifluoromethylphenyl | 2-ethoxy-5-oxo-tetrahydrofuran-3-yl | —CH₂SH |
| 215 | 4-trifluoromethylphenyl | 2-ethoxy-5-oxo-tetrahydrofuran-3-yl | —CH₂SH |
| 216 | 3-methoxyphenyl | 2-ethoxy-5-oxo-tetrahydrofuran-3-yl | —CH₂SH |
| 217 | 4-methoxyphenyl | 2-ethoxy-5-oxo-tetrahydrofuran-3-yl | —CH₂SH |
| 218 | 3-acetylphenyl | 2-ethoxy-5-oxo-tetrahydrofuran-3-yl | —CH₂SH |
| 219 | 4-acetylphenyl | 2-ethoxy-5-oxo-tetrahydrofuran-3-yl | —CH₂SH |
| 220 | 3-benzoylphenyl | 2-ethoxy-5-oxo-tetrahydrofuran-3-yl | —CH₂SH |
| 221 | 1-naphthyl | 2-ethoxy-5-oxo-tetrahydrofuran-3-yl | —CH₂SH |
| 222 | 2-naphthyl | 2-ethoxy-5-oxo-tetrahydrofuran-3-yl | —CH₂SH |
| 223 | 2-quinolinyl | 2-ethoxy-5-oxo-tetrahydrofuran-3-yl | —CH₂SH |
| 224 | 1-isoquinolinyl | 2-ethoxy-5-oxo-tetrahydrofuran-3-yl | —CH₂SH |
| 225 | 2-benzothiaphenyl | 2-ethoxy-5-oxo-tetrahydrofuran-3-yl | —CH₂SH |
| 226 | phenyl | 2-ethoxy-5-oxo-tetrahydrofuran-3-yl | —CH₂SC₆H₅ |
| 227 | 3-fluorophenyl | 2-ethoxy-5-oxo-tetrahydrofuran-3-yl | —CH₂SC₆H₅ |
| 228 | 4-fluorophenyl | 2-ethoxy-5-oxo-tetrahydrofuran-3-yl | —CH₂SC₆H₅ |
| 229 | 3-trifluoromethylphenyl | 2-ethoxy-5-oxo-tetrahydrofuran-3-yl | —CH₂SC₆H₅ |
| 230 | 4-trifluoromethylphenyl | 2-ethoxy-5-oxo-tetrahydrofuran-3-yl | —CH₂SC₆H₅ |
| 231 | 3-methoxyphenyl | 2-ethoxy-5-oxo-tetrahydrofuran-3-yl | —CH₂SC₆H₅ |
| 232 | 4-methoxyphenyl | 2-ethoxy-5-oxo-tetrahydrofuran-3-yl | —CH₂SC₆H₅ |
| 233 | 3-acetylphenyl | 2-ethoxy-5-oxo-tetrahydrofuran-3-yl | —CH₂SC₆H₅ |
| 234 | 4-acetylphenyl | 2-ethoxy-5-oxo-tetrahydrofuran-3-yl | —CH₂SC₆H₅ |
| 235 | 3-benzoylphenyl | 2-ethoxy-5-oxo-tetrahydrofuran-3-yl | —CH₂SC₆H₅ |
| 236 | 1-naphthyl | 2-ethoxy-5-oxo-tetrahydrofuran-3-yl | —CH₂SC₆H₅ |
| 237 | 2-naphthyl | 2-ethoxy-5-oxo-tetrahydrofuran-3-yl | —CH₂SC₆H₅ |
| 238 | 2-quinolinyl | 2-ethoxy-5-oxo-tetrahydrofuran-3-yl | —CH₂SC₆H₅ |
| 239 | 1-isoquinolinyl | 2-ethoxy-5-oxo-tetrahydrofuran-3-yl | —CH₂SC₆H₅ |
| 240 | 2-benzothiaphenyl | 2-ethoxy-5-oxo-tetrahydrofuran-3-yl | —CH₂SC₆H₅ |

The compounds of Category III can be suitably prepared by the procedure outlined herein below, utilizing intermediate 15 which can be synthesized by the procedure described in Scheme V.

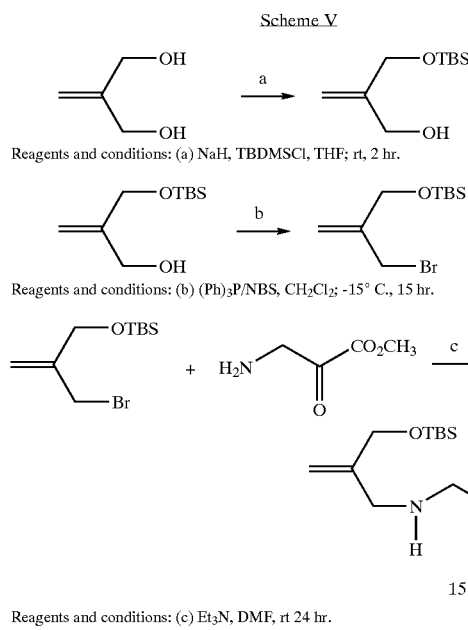

Reagents and conditions: (a) NaH, TBDMSCl, THF; rt, 2 hr.

Reagents and conditions: (b) (Ph)₃P/NBS, CH₂Cl₂; -15° C., 15 hr.

Reagents and conditions: (c) Et₃N, DMF, rt 24 hr.

Preparation of 2-(tert-Butyl-dimethyl-silanyloxymethyl)-prop-2-en-1-ol: Sodium hydride (0.46 g, 11.3 mmol) is suspended in THF (20 mL) and 2-methylene-1,3-propandiol (1 g, 11.3 mmol) is added and the mixture is stirred at room temperature for 20 min by which time an opaque white precipitate forms. tert-Butyldimethylsilyl chloride is then added, and the solution vigorously stirred for 2 hours. The resulting mixture is poured into ether (50 mL), washed with 10% aqueous K₂CO₃, brine, dried (Na₂SO₄), and concentrated in vacuo to yield a crude residue which is purified over silica to afford 1.6 g (70% yield) of the desired product as a clear oil. $^1$H NMR (CDCl₃) δ 5.11–5.09 (m, 2H), 4.24 (s, 2H), 4.16 (s, 2H), 2.51 (s, 1H), 0.93 (s, 9H), 0.11–0.08 (m, 6H); $^{13}$C (CDCl₃) 8 147.7, 111.0, 65.1, 64.5, 26.1, 18.5, -5.2; MS 203 (M+H)$^+$.

Preparation of (2-bromomethyl-allyloxy)-tert-butyl-dimethyl-silane: To a solution of 2-(tert-butyl-dimethyl-silanyloxymethyl)-prop-2-en-1-ol (0.335 g, 1.65 mmol) in dry CH₂CL₂ (5 mL), at -15° C. are added triphenylphosphine (0.5 g, 1.90 mmol) and N-bromosuccinimide (0.3 g, 1.65 mmol). After stirring at -15° C. for 5 hours, the solution is added to a mixture of diethyl ether and water. The organic phase is washed with brine, dried (Na₂SO₄), and purified over silica (EtOAc/hexane) to afford 0.17 g (39% yield) of the desired product. $^1$H NMR (CDCl₃) δ 5.27–5.25 (m, 2H), 4.29 (s, 2H), 4.03 (s, 2H), 0.98 (s, 9H), 0.38–0.28 (m 6H); $^{13}$C (CDCl₃) δ 145.0, 115.0, 109.2, 64.1, 63.7, 32.9, 31.8, 26.1, 22.9, 18.5, 14.3.

Preparation of [2-(tert-butyl-dimethyl-silaneloxymethyl)-allylamino]-acetic acid methyl ester (15): Glycine methyl ester hydrochloride (0.28 9, 2.26 mmol), triethylamine (0.63 mL, 4.54 mmol) and (2-bromomethyl-allyloxy)-tert-butyl-dimethyl-silane (0.24 g, 0.91 mmol) are dissolved in DMF (5 mL) and stirred at room temperature for 24 hours. To this solution is added diethyl ether and water and the organic phase washed with brine, dried (Na₂SO₄) and concentrated in vacuo to provide a crude residue which is purified over silica (EtOAc/hexane) to afford 0.107 g (43% yield) of the desired product. $^1$H NMR (CDCl₃) δ 5.13 (bs, 1H), 54.99 (bs, 1H), 4.15 (bs, 2H), 3.71 (s, 3H), 3.38 (s, 2H), 3.25 (s, 2H), 1.71 (s, 1H), 0.90 (s, 9H), 0.06 (s, 6H); $^{13}$C (CDCl₃) δ 173.1, 146.3, 111.1, 65.0, 51.9, 51.6, 50.0, 26.1, 18.5, -5.1; MS 274 (M+H)$^+$.

Intermediate 15, prepared by the procedure herein above, can be reacted with a suitable reagent which introduces the selected R unit into the compound scaffold as described in Scheme VI herein below.

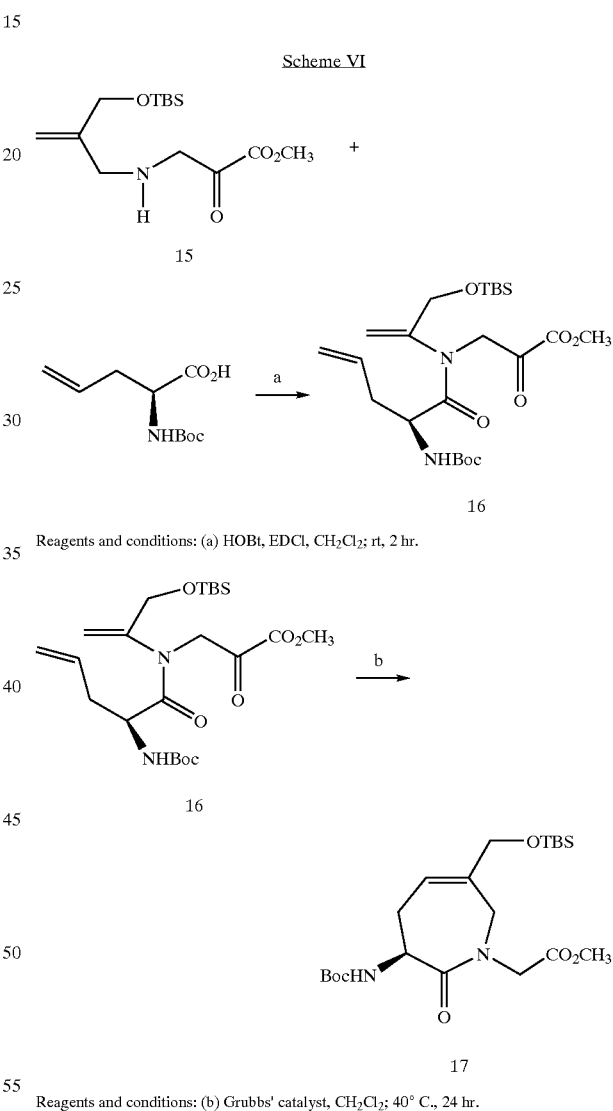

Reagents and conditions: (a) HOBt, EDCl, CH₂Cl₂; rt, 2 hr.

Reagents and conditions: (b) Grubbs' catalyst, CH₂Cl₂; 40° C., 24 hr.

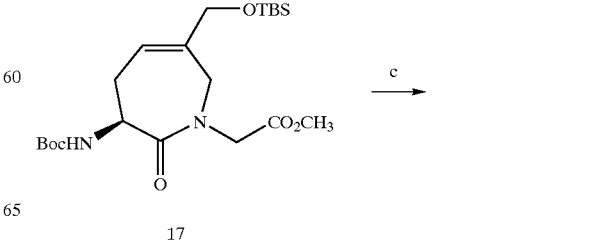

-continued

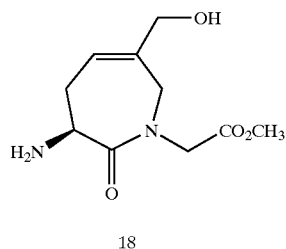

18

Reagents and conditions: (c) TFA, CH$_2$Cl$_2$; rt, 30 min.

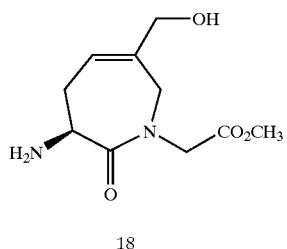

18

Reagents and conditions: (d) HOBt, EDCl, CH$_2$Cl$_2$; rt, 3 hr.

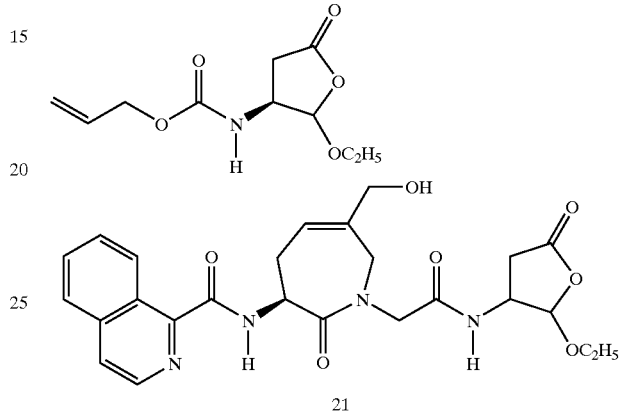

Reagents and conditions: (e) LiOH, THF, H$_2$O; rt, 2.5 hr.

-continued

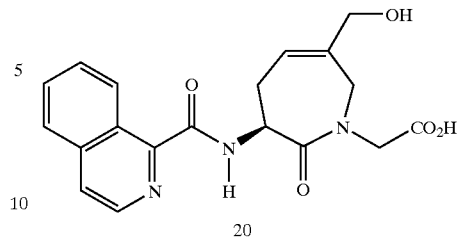

20

+

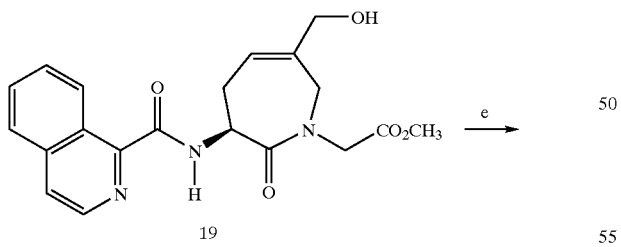

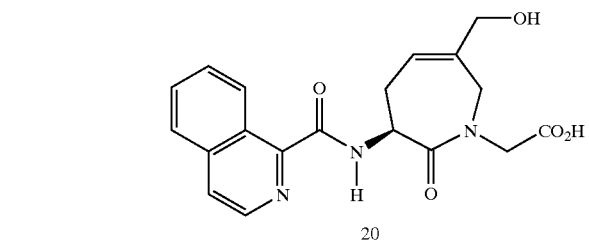

21

Reagents and conditions: (f) N,N-dimethylbarbituric acid, (Ph$_3$P)$_4$Pd, CH$_2$Cl$_2$, EDCl, HOBt; rt, 5 hr.

EXAMPLE 3

Isoquinoline-1-carboxylic acid {6-hydroxymethyl-1-[(2-ethoxy-5-oxo-tetrahydro-furan-3-ylcarbamoyl)-methyl]-2-oxo-2,3,4,7-tetrahydro-1H-azepin-3-yl}-amide (21)

Preparation of {(2-tert-butoxycarbonylamino-pent-4-enoyl)-[2-(tert-butyl-dimethyl-silanyloxymethyl)-allyl]-amino}-acetic acid methyl ester (16): A solution of [2-(tert-butyl-dimethyl-silaneloxymethyl)-allylamino]-acetic acid methyl ester, 15, (6 g, 21.9 mmol), N-Boc allylglycine (7.2 g, 32.9 mmol), HOBt (6 g, 43.9 mmol) and EDCl (8.5 g, 43.9 mmol) in CH$_2$Cl$_2$ (50 mL) is stirred at room temperature for 2 hours. The reaction is diluted with EtOAc, washed with saturated NaHCO$_3$, saturated NaCl, and dried (Na$_2$SO$_4$). The solvent is removed in vacuo and the residue purified over silica (EtOAc/hexane) to afford 5.9 g (57% yield) of the desired product. $^1$H NMR (CDCl$_3$) δ 5.77–5.61 (m, 1H), 5.15–4.85 (series of m, 4H), 4.64–3.76 (series of m, 7H), 3.63 (s, 3H), 2.47–2.42 (m, 1H), 2.34–2.23 (m, 1H), 1.34 (s, 9H), 0.82 (s, 9H), 0.04–0.02 (m, 6H); $^{13}$C (CDCl$_3$, rotamers) δ 174.1, 174.0, 171.0, 170.7, 156.8, 156.5, 144.7, 134.7, 134.3, 120.8, 120.0, 114.2, 113.7, 80.9, 80.7, 65.6, 65.3, 53.8, 53.4, 51.9, 51.4, 51.2, 50.1, 49.5, 48.5, 39.0, 38.6, 29.7, 27.3, 19.7, −3.9; MS 471 (M+H)$^+$.

Preparation of [3-tert-butoxycarbonylamino-6-(tert-butyl-dimethyl-silanyloxymethyl)-oxo-2,3,4,7-tetrahydro-azepin-1-yl]-acetic acid methyl ester (17): Super Grubbs catalyst (2 g) is added to a solution {(2-tert-butoxycarbonylamino-pent-4-enoyl)-[2-(tert-butyl-dimethyl-silanyloxymethyl)-allyl]- amino}-acetic acid methyl ester, 16, (4.1 g, 8.7 mmol) in CH$_2$Cl$_2$(100 mL). The solution is refluxed for 1 hour then DMSO (10 mL) is added and stirring is continued for another 12 hours at room temperature. The solvent is removed in vacuo and the residue purified over silica (EtOAc/hexane) to afford 3.7 g (96% yield) of the desired product. $^1$H NMR (CDCl$_3$) δ 5.80–5.78 (d, J=6.3 Hz, 1H), 5.65 (bs, 1H), 5.03–4.96 (m, 1H), 4.56–4.48 (m, 2H), 3.98 (s, 2H), 3.98–3.92 (d, J=17.4 Hz, 1H), 3.73 (s, 3H), 3.44–3.38 (d, J=17.7, 1H), 2.74–2.67 (d, d, J=18, 3.3 Hz, 1H), 2.30–2.18 (m, 1H), 1.45 (s, 9H), 0.89 (s, 9H), 0.06 (s, 6H); $^{13}$C (CDCl$_3$) δ 172.9, 169.6, 155.2, 135.6, 124.6, 79.7, 66.9, 60.5, 52.4, 50.0, 49.8, 47.6, 33.1, 28.5, 26.0, 18.4,14.4, –5.0; MS 442 (M+H)$^+$.

Preparation of (6-hydroxymethyl-3-amino-2-oxo-2,3,4,7-tetrahydro-azepin-1-yl)-acetic acid methyl ester (18): A solution of [3-tert-Butoxycarbonylamino-6-(tert-butyl-dimethyl-silanyloxymethyl)-oxo-2,3,4,7-tetrahydro-azepin-1-yl]-acetic acid methyl ester, 17, (4.32 g, 9.7 mmol) in CH$_2$Cl$_2$ (20 mL) is treated with wet TFA (5 mL) and stirred at rt for 30 min. The solution is concentrated in vacuo using toluene to azeotrope off the solvent. The crude product is used without further purification.

Preparation of {6-hydroxymethyl-3-[(isoquinoline-1-carbonyl)-amino]-2-oxo-2,3,4,7-tetrahydro-azepin-1-yl}-acetic acid methyl ester (19): The crude residue obtained from the procedure herein above is combined with 1-isoquinolinecarboxylic acid (2.6 g, 15.0 mmol), HOBt (2.68 g, 19.8 mmol), and EDCl (3.8 g, 19.8 mmol) in DMF (20 mL). The solution is stirred for 3 hours at room temperature then diluted with EtOAc, washed with saturated NaHCO$_3$, saturated NaCl, and dried (Na$_2$SO$_4$). The solvent is removed in vacuo and the residue obtained purified by HPLC to afford 1.7 g (40% yield) of the desired product. $^1$H NMR (CDCl$_3$) δ 9.49–9.46 (d, J=7.8 Hz, 1H), 9.20–9.18 (d, J=6.9 Hz, 1H), 8.52–8.50 (d, J=5.5 Hz, 1H), 7.86–7.78 (m, 2H), 7.72–7.63 (m, 2H), 5.79 (bs, 1H), 5.55–5.47 (m, 1H), 4.76–4.69 (d, d, J=17.3, 2.3 Hz, 1H), 4.45–4.40 (d, J=17.4 Hz, 1H), 4.25–4.19 (d, J=17.4 Hz, 1H), 4.15–3.98 (m, 3H), 3.73 (s, 3H), 3.65–3.59 (d, J=17.4 Hz, 1H), 2.97–2.90 (d, d, J=18.2, 3.9 Hz, 1H), 2.48–2.29 (m, 3H); $^{13}$C (CDCl$_3$) δ172.7, 170.5, 165.9, 148.2, 141.0, 137.7, 136.3, 130.7, 128.9, 127.7, 127.2, 126.4, 124.7, 67.5, 60.8, 52.8, 50.3, 49.3, 48.1, 32.5, 21.4, 14.5; MS 384 (M+H)$^+$.

Preparation of {6-(hydroxymethyl)-3-[(isoquinoline-1-carbonyl)amino]-2-oxo-2,3,4,7-tetrahydro-azepin-1-yl}-acetic acid (20): A solution of {6-hydroxymethyl-3-[(isoquinoline-1-carbonyl)-amino]-2-oxo-2,3,4,7-tetrahydro-azepin-1-yl}-acetic acid methyl ester, 19, (0.16 g, 0.41 mmol) in THF/H$_2$O (4 mL, 3:1) is treated with excess LiOH and stirred for 2.5 hours at room temperature. The solution is acidified to pH 7, concentrated in vacuo and purified by HPLC to afford 0.15 g of the desired product.

Preparation of isoquinoline-1-carboxylic acid {6-(hydroxymethyl)-1-[(2-ethoxy-5-oxo-tetrahydro-furan-3-ylcarbamoyl)-methyl]-2-oxo-2,3,4,7-tetrahydro-1H-azepin-3-yl}-amide (21): A catalytic amount of Pd(Ph$_3$P)$_4$ is added to a solution of (2-Ethoxy-5-oxo-furan-3-yl)-carbamic acid allyl ester (0.24 g, 1.0 mmol) and N,N-dimethylbarbituric acid (0.38 g, 2.4 mmol) in CH$_2$Cl$_2$ (5 mL). The solution is stirred for 15 minutes at room temperature after which {6-(tert-butyl-dimethyl-silanyloxymethyl)-3-[(isoquinoline-1-carbonyl)amino]-2-oxo-2,3,4,7-tetrahydro-azepin-1-yl}-acetic acid, 22, (0.15 g) is added as a solution in CH$_2$Cl$_2$/DMF (2 mL, 1:1), followed by HOBt (0.126 g, 0.93 mmol) and EDCl (0.18 g, 0.93 mmol). The solution is stirred for 5 hours, diluted with EtOAc, washed with saturated NaHCO$_3$ and brine, dried (Na$_2$SO$_4$), and concentrated in vacuo. The resulting residue us purified over silica (EtOAc/hexane) to afford the desired compound.

The compounds of this category wherein R$^1$ comprises the cysteine trap 2-hydroxy-5-oxo-tetrahydrofuran-3-yl can be prepared by the procedure outlined in Scheme VII as indicated in the following example starting with compound 21.

Scheme VII

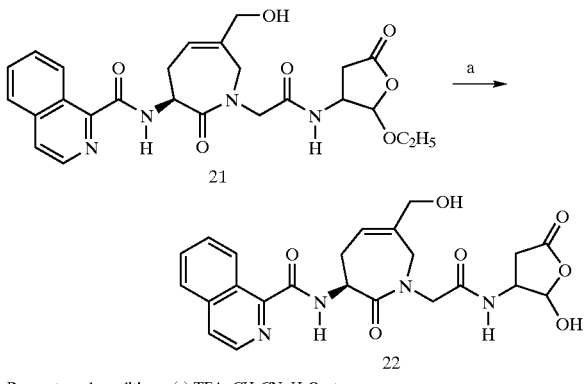

Reagents and conditions: (a) TFA. CH$_3$CN, H$_2$O; rt.

EXAMPLE 4

Isoquinoline-1-carboxylic acid {6-hydroxymethyl-1-[(2-hydroxy-5-oxo-tetrahydro-furan-3-ylcarbamoyl)-methyl]-2-oxo-2,3,4,7-tetrahydro-1H-azepin-3-yl}-amide (22)

Preparation of isoquinoline-1-carboxylic acid {6-hydroxymethyl-1-[(2-hydroxy-5-oxo-tetrahydro-furan-3-ylcarbamoyl)-methyl]-2-oxo-2,3,4,7-tetrahydro-1H-azepin-3-yl}-amide (22): Isoquinoline-1-carboxylic acid {6-hydroxymethyl-1-[(2-hydroxy-5-oxo-tetrahydro-furan-3-ylcarbamoyl)-methyl]-2-oxo-2,3,4,7-tetrahydro-1H-azepin-3-yl}-amide, 21, prepared herein above is treatment with TFA in CH$_3$CN/H$_2$O to afford the desired compound which is purified by preparative reverse phase HPLC to afford 35 mg (18% yield) of the desired product. $^1$H NMR (CD$_3$OD) δ 9.23–9.20 (d, J=8.4 Hz, 1H), 8.56–8.54 (d, J=5.7 Hz, 1H), 8.03–7.99 (m, 2H), 7.87–7.81 (d, d, J=6.9, 5.1 Hz, 1H), 7.77–7.73, (d, d, J=7.5, 7.2 Hz, 1H), 5.84 (bs, 1H), 5.61–5.52 (d, d, J=12.6, 4.2 Hz, 1H), 4.83–4.77 (d, J=16.5 Hz, 1H), 4.65–4.77 (d, d, J=3.6, 3.3 Hz, 1H), 4.43–4.32 (m, 2H), 4.18–4.04 (m, 3H), 3.69–3.51 (m, 1H), 3.40–3.30 (m, 1H), 2.92–2.44 (m, 6H); MS 469 (M+H)$^+$.

Other non-limiting examples of compounds which comprise this aspect of Category III include:

Naphthalene-2-carboxylic acid {6-benzylsulfanylmethyl-1-[(2-hydroxy-5-oxo-tetrahydro-furan-3-ylcarbamoyl)-methyl]-2-oxo-2,3,4,7-tetrahydro-1H-azepin-3-yl}-amide : $^1$H NMR (CD$_3$OD) δ 8.46 (s, 1H), 8.01–7.91 (m, 4H), 7.63–7.55 (m, 2H), 7.35 –7.22 (m, 5H), 5.56–5.48 (m, 2H), 4.75–4.69 (d, J=17.1 Hz, 1H), 4.66–4.63 (d, d, J=3.6, 3.6 Hz, 1H), 4.41–4.34 (m, 2H), 4.16–4.10 (d, d, J=16.5, 2.4 Hz, 1H), 3.68–3.67 (d, J=2.7 Hz, 1H), 3.58–3.51 (d, d, J=17.4, 4.8 Hz, 1H), 3.38 (s, 2H), 3.18 (d, J=14.1 Hz, 1H), 3.04–2.99 (d, J=13.5 Hz, 1H), 2.76–2.66 (m, 2H), 2.58–2.49 (m, 2H); MS 574 (M+H).

Naphthalene-2-carboxylic acid {1-[(2-hydroxy-5-oxo-tetrahydro-furan-3-ylcarbamoyl)-methyl]-2-oxo-6-phenylsulfanylmethyl-2,3,4,7-tetrahydro-1H-azepin-3-yl}-amide: ¹H NMR (CD₃OD) δ 8.45 (s, 1H), 8.01–7.90 (m, 4H), 7.63–7.55 (m, 2H), 7.44–7.23 (m, 5H), 5.52–5.47 (m, 2H), 4.68–4.79 (m, 1H), 4.66–4.63 (d, d, J=4.2, 4.2 Hz, 1H), 4.47–4.33 (m, 2H), 4.16–4.10 (d, d, J=16.2, 2.4 Hz, 1H), 3.72–3.65 (m, 2H), 3.52–3.48 (d, J=13.5 Hz, 1H), 3.39–3.38 (m, 1H), 2.77–2.64 (m, 2H), 2.58–2.49 (m, 2H), 2.43–2.33 (d, d, J=16.8, 13.8 Hz, 1H); MS 560 (M+H).

Naphthalene-2-carboxylic acid {6-hydroxymethyl-1-[(2-hydroxy-5-oxo-tetrahydro-furan-3-ylcarbamoyl)-methyl]-2-oxo-2,3,4,7-tetrahydro-1H-azepin-3-yl}-amide: ¹H NMR (CD₃OD) δ 8.47 (s, 1H), 8.02–7.85 (m, 4H), 7.64–7.50 (m, 2H), 5.81 (bs, 1H), 5.56 (dd, J=12.9, 3.9 Hz, 1H), 4.78 (d, J=18.3 Hz, 1H), 4.64 (dd, J=4.2, 3.6 Hz, 1H), 4.38–4.31 (M, 3H), 4.15 (dd, J=15.9, 3.3 Hz, 1H), 3.66–3.55 (m, 2H), 2.79–2.65 (m, 2H), 2.59–2.48 (m, 2H); MS 468 (M+H).

The second aspect of Category III comprises scaffolds having the formula:

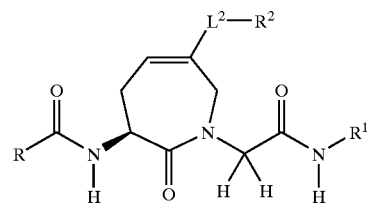

wherein R, R¹, L and R² are described herein below in Table IV.

TABLE IV

| No. | R | R¹ | L² | R² |
|---|---|---|---|---|
| 241 | phenyl | 2-hydroxy-5-oxo-tetrahydrofuran-3-yl | —CH₂NH— | phenyl |
| 242 | 2-naphthyl | 2-hydroxy-5-oxo-tetrahydrofuran-3-yl | —CH₂NH— | phenyl |
| 243 | 1-isoquinolinyl | 2-hydroxy-5-oxo-tetrahydrofuran-3-yl | —CH₂NH— | phenyl |
| 244 | phenyl | 2-hydroxy-5-oxo-tetrahydrofuran-3-yl | —CH₂NH— | 4-isopropylphenyl |
| 245 | 2-naphthyl | 2-hydroxy-5-oxo-tetrahydrofuran-3-yl | —CH₂NH— | 4-isopropylphenyl |
| 246 | 1-isoquinolinyl | 2-hydroxy-5-oxo-tetrahydrofuran-3-yl | —CH₂NH— | 4-isopropylphenyl |
| 247 | phenyl | 2-hydroxy-5-oxo-tetrahydrofuran-3-yl | —CH₂NH— | 4-pentylphenyl |
| 248 | 2-naphthyl | 2-hydroxy-5-oxo-tetrahydrofuran-3-yl | —CH₂NH— | 4-pentylphenyl |
| 249 | 1-isoquinolinyl | 2-hydroxy-5-oxo-tetrahydrofuran-3-yl | —CH₂NH— | 4-pentylphenyl |
| 250 | phenyl | 2-hydroxy-5-oxo-tetrahydrofuran-3-yl | —CH₂NH— | 2-fluorophenyl |
| 251 | 2-naphthyl | 2-hydroxy-5-oxo-tetrahydrofuran-3-yl | —CH₂NH— | 2-fluorophenyl |
| 252 | 1-isoquinolinyl | 2-hydroxy-5-oxo-tetrahydrofuran-3-yl | —CH₂NH— | 2-fluorophenyl |
| 253 | phenyl | 2-hydroxy-5-oxo-tetrahydrofuran-3-yl | —CH₂NH— | 3-fluorophenyl |
| 254 | 2-naphthyl | 2-hydroxy-5-oxo-tetrahydrofuran-3-yl | —CH₂NH— | 3-fluorophenyl |
| 255 | 1-isoquinolinyl | 2-hydroxy-5-oxo-tetrahydrofuran-3-yl | —CH₂NH— | 3-fluorophenyl |
| 256 | phenyl | 2-hydroxy-5-oxo-tetrahydrofuran-3-yl | —CH₂NH— | 4-fluorophenyl |
| 257 | 2-naphthyl | 2-hydroxy-5-oxo-tetrahydrofuran-3-yl | —CH₂NH— | 4-fluorophenyl |
| 258 | 1-isoquinolinyl | 2-hydroxy-5-oxo-tetrahydrofuran-3-yl | —CH₂NH— | 4-fluorophenyl |
| 259 | phenyl | 2-hydroxy-5-oxo-tetrahydrofuran-3-yl | —CH₂NH— | 2-methylphenyl |
| 260 | 2-naphthyl | 2-hydroxy-5-oxo-tetrahydrofuran-3-yl | —CH₂NH— | 2-methylphenyl |
| 261 | 1-isoquinolinyl | 2-hydroxy-5-oxo-tetrahydrofuran-3-yl | —CH₂NH— | 2-methylphenyl |
| 262 | phenyl | 2-hydroxy-5-oxo-tetrahydrofuran-3-yl | —CH₂NH— | 3-methylphenyl |
| 263 | 2-naphthyl | 2-hydroxy-5-oxo-tetrahydrofuran-3-yl | —CH₂NH— | 3-methylphenyl |
| 264 | 1-isoquinolinyl | 2-hydroxy-5-oxo-tetrahydrofuran-3-yl | —CH₂NH— | 3-methylphenyl |
| 265 | phenyl | 2-hydroxy-5-oxo-tetrahydrofuran-3-yl | —CH₂NH— | 4-methylphenyl |
| 266 | 2-naphthyl | 2-hydroxy-5-oxo-tetrahydrofuran-3-yl | —CH₂NH— | 4-methylphenyl |
| 267 | 1-isoquinolinyl | 2-hydroxy-5-oxo-tetrahydrofuran-3-yl | —CH₂NH— | 4-methylphenyl |
| 268 | phenyl | 2-hydroxy-5-oxo-tetrahydrofuran-3-yl | —CH₂NH— | 2-methoxyphenyl |
| 269 | 2-naphthyl | 2-hydroxy-5-oxo-tetrahydrofuran-3-yl | —CH₂NH— | 2-methoxyphenyl |
| 270 | 1-isoquinolinyl | 2-hydroxy-5-oxo-tetrahydrofuran-3-yl | —CH₂NH— | 2-methoxyphenyl |
| 271 | phenyl | 2-hydroxy-5-oxo-tetrahydrofuran-3-yl | —CH₂NH— | 3-methoxyphenyl |
| 272 | 2-naphthyl | 2-hydroxy-5-oxo-tetrahydrofuran-3-yl | —CH₂NH— | 3-methoxyphenyl |
| 273 | 1-isoquinolinyl | 2-hydroxy-5-oxo-tetrahydrofuran-3-yl | —CH₂NH— | 3-methoxyphenyl |
| 274 | phenyl | 2-hydroxy-5-oxo-tetrahydrofuran-3-yl | —CH₂NH— | 4-methoxyphenyl |
| 275 | 2-naphthyl | 2-hydroxy-5-oxo-tetrahydrofuran-3-yl | —CH₂NH— | 4-methoxyphenyl |
| 276 | 1-isoquinolinyl | 2-hydroxy-5-oxo-tetrahydrofuran-3-yl | —CH₂NH— | 4-methoxyphenyl |
| 277 | phenyl | 2-hydroxy-5-oxo-tetrahydrofuran-3-yl | —CH₂NHCH₂— | phenyl |
| 278 | 2-naphthyl | 2-hydroxy-5-oxo-tetrahydrofuran-3-yl | —CH₂NHCH₂— | phenyl |
| 279 | 1-isoquinolinyl | 2-hydroxy-5-oxo-tetrahydrofuran-3-yl | —CH₂NHCH₂— | phenyl |
| 280 | phenyl | 2-hydroxy-5-oxo-tetrahydrofuran-3-yl | —CH₂NHCH₂— | 4-isopropylphenyl |
| 281 | 2-naphthyl | 2-hydroxy-5-oxo-tetrahydrofuran-3-yl | —CH₂NHCH₂— | 4-isopropylphenyl |
| 282 | 1-isoquinolinyl | 2-hydroxy-5-oxo-tetrahydrofuran-3-yl | —CH₂NHCH₂— | 4-isopropylphenyl |
| 283 | phenyl | 2-hydroxy-5-oxo-tetrahydrofuran-3-yl | —CH₂NHCH₂— | 4-pentylphenyl |
| 284 | 2-naphthyl | 2-hydroxy-5-oxo-tetrahydrofuran-3-yl | —CH₂NHCH₂— | 4-pentylphenyl |
| 285 | 1-isoquinolinyl | 2-hydroxy-5-oxo-tetrahydrofuran-3-yl | —CH₂NHCH₂— | 4-pentylphenyl |
| 286 | phenyl | 2-hydroxy-5-oxo-tetrahydrofuran-3-yl | —CH₂NHCH₂— | 2-fluorophenyl |
| 287 | 2-naphthyl | 2-hydroxy-5-oxo-tetrahydrofuran-3-yl | —CH₂NHCH₂— | 2-fluorophenyl |
| 288 | 1-isoquinolinyl | 2-hydroxy-5-oxo-tetrahydrofuran-3-yl | —CH₂NHCH₂— | 2-fluorophenyl |
| 289 | phenyl | 2-hydroxy-5-oxo-tetrahydrofuran-3-yl | —CH₂NHCH₂— | 3-fluorophenyl |
| 290 | 2-naphthyl | 2-hydroxy-5-oxo-tetrahydrofuran-3-yl | —CH₂NHCH₂— | 3-fluorophenyl |
| 291 | 1-isoquinolinyl | 2-hydroxy-5-oxo-tetrahydrofuran-3-yl | —CH₂NHCH₂— | 3-fluorophenyl |
| 292 | phenyl | 2-hydroxy-5-oxo-tetrahydrofuran-3-yl | —CH₂NHCH₂— | 4-fluorophenyl |
| 293 | 2-naphthyl | 2-hydroxy-5-oxo-tetrahydrofuran-3-yl | —CH₂NHCH₂— | 4-fluorophenyl |
| 294 | 1-isoquinolinyl | 2-hydroxy-5-oxo-tetrahydrofuran-3-yl | —CH₂NHCH₂— | 4-fluorophenyl |
| 295 | phenyl | 2-hydroxy-5-oxo-tetrahydrofuran-3-yl | —CH₂NHCH₂— | 2-methylphenyl |
| 296 | 2-naphthyl | 2-hydroxy-5-oxo-tetrahydrofuran-3-yl | —CH₂NHCH₂— | 2-methylphenyl |

TABLE IV-continued

| No. | R | R¹ | L² | R² |
|---|---|---|---|---|
| 297 | 1-isoquinolinyl | 2-hydroxy-5-oxo-tetrahydrofuran-3-yl | —CH$_2$NHCH$_2$— | 2-methylphenyl |
| 298 | phenyl | 2-hydroxy-5-oxo-tetrahydrofuran-3-yl | —CH$_2$NHCH$_2$— | 3-methylphenyl |
| 299 | 2-naphthyl | 2-hydroxy-5-oxo-tetrahydrofuran-3-yl | —CH$_2$NHCH$_2$— | 3-methylphenyl |
| 300 | 1-isoquinolinyl | 2-hydroxy-5-oxo-tetrahydrofuran-3-yl | —CH$_2$NHCH$_2$— | 3-methylphenyl |
| 301 | phenyl | 2-hydroxy-5-oxo-tetrahydrofuran-3-yl | —CH$_2$NHCH$_2$— | 4-methylphenyl |
| 302 | 2-naphthyl | 2-hydroxy-5-oxo-tetrahydrofuran-3-yl | —CH$_2$NHCH$_2$— | 4-methylphenyl |
| 303 | 1-isoquinolinyl | 2-hydroxy-5-oxo-tetrahydrofuran-3-yl | —CH$_2$NHCH$_2$— | 4-methylphenyl |
| 304 | phenyl | 2-hydroxy-5-oxo-tetrahydrofuran-3-yl | —CH$_2$NHCH$_2$— | 2-methoxyphenyl |
| 305 | 2-naphthyl | 2-hydroxy-5-oxo-tetrahydrofuran-3-yl | —CH$_2$NHCH$_2$— | 2-methoxyphenyl |
| 306 | 1-isoquinolinyl | 2-hydroxy-5-oxo-tetrahydrofuran-3-yl | —CH$_2$NHCH$_2$— | 2-methoxyphenyl |
| 307 | phenyl | 2-hydroxy-5-oxo-tetrahydrofuran-3-yl | —CH$_2$NHCH$_2$— | 3-methoxyphenyl |
| 308 | 2-naphthyl | 2-hydroxy-5-oxo-tetrahydrofuran-3-yl | —CH$_2$NHCH$_2$— | 3-methoxyphenyl |
| 309 | 1-isoquinolinyl | 2-hydroxy-5-oxo-tetrahydrofuran-3-yl | —CH$_2$NHCH$_2$— | 3-methoxyphenyl |
| 310 | phenyl | 2-hydroxy-5-oxo-tetrahydrofuran-3-yl | —CH$_2$NHCH$_2$— | 4-methoxyphenyl |
| 311 | 2-naphthyl | 2-hydroxy-5-oxo-tetrahydrofuran-3-yl | —CH$_2$NHCH$_2$— | 4-methoxyphenyl |
| 312 | 1-isoquinolinyl | 2-hydroxy-5-oxo-tetrahydrofuran-3-yl | —CH$_2$NHCH$_2$— | 4-methoxyphenyl |

The compounds of the second aspect of Category III can be suitably prepared by the procedure outlined herein below, utilizing intermediates such as 19 as a starting point which can be synthesized by the procedure described in Scheme VIII.

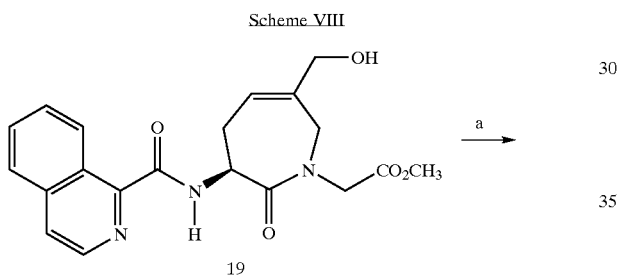

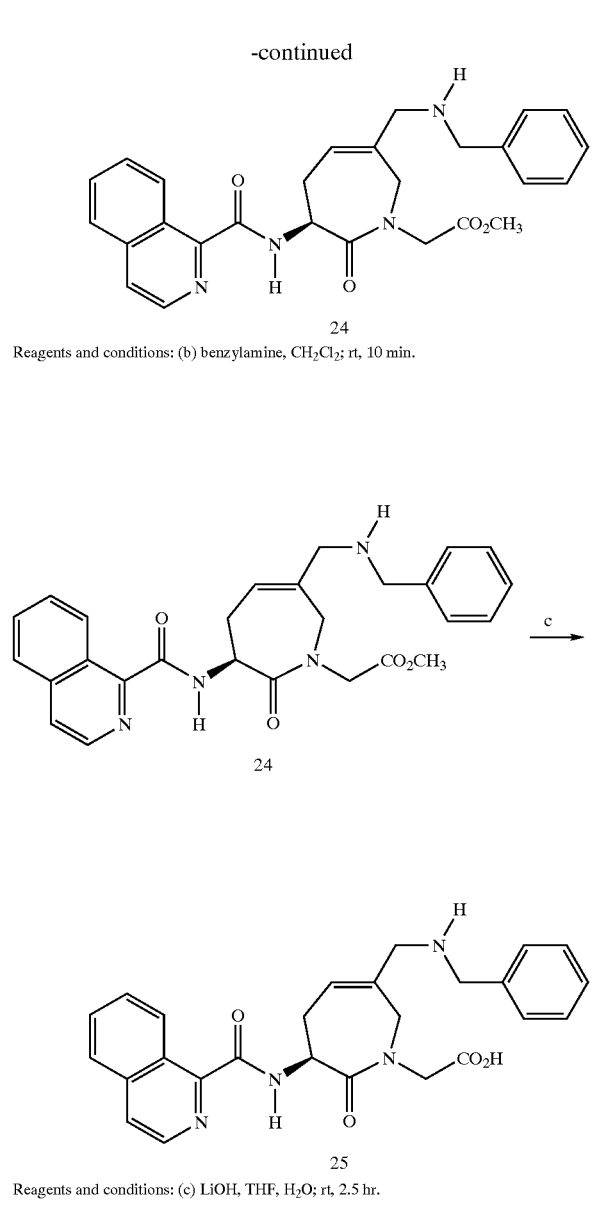

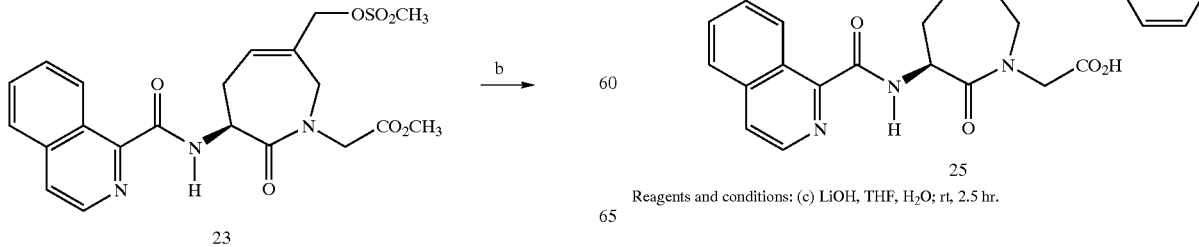

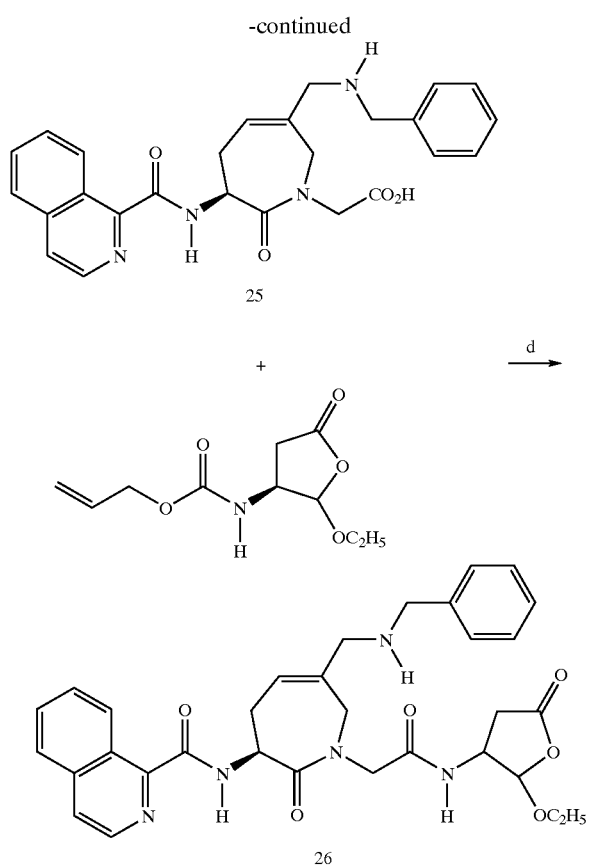

Reagents and conditions: (d) N,N-dimethylbarbituric acid, (Ph₃P)₄Pd, CH₂Cl₂, EDCl, HOBt; rt, 5 hr.

EXAMPLE 5

Isoquinoline-1-carboxylic acid {6-(benzylamino-methyl)-1-[(2-ethoxy-5-oxo-tetrahydro-furan-3-yl-carbamoyl)-methyl]-2-oxo-2,3,4,7-tetrahydro-1H-azepin-3-yl}-amide (26)

Preparation of {6-[(methanesulfonyl)methyl]-3-[(isoquinoline-1-carbonyl)-amino]-2-oxo-2,3,4,7-tetrahydro-azepin-1-yl}-acetic acid methyl ester (23): A solution of {6-hydroxymethyl-3-[(isoquinoline-1-carbonyl)-amino]-2-oxo-2,3,4,7-tetrahydro-azepin-1-yl}-acetic acid methyl ester, 19, (1.35 g, 3.52 mmol) in 10 mL CH₂Cl₂ is treated with triethyl amine (1.3 mL, 8.81 mmol) and methanesulfonyl chloride (0.61 mL, 7.93 mmol) at −78° C. After stirring at −78° C. for 2 hours, the reaction mixture is poured into a CH₂Cl₂/saturated NaCl solution. The organic layer is collected and washed with saturated NaHCO₃, saturated NaCl, dried (Na₂SO₄) and concentrated in vacuo to afford the desired product which is used without further purification.

Preparation of {6-(benzylamino-methyl)-3-[(isoquinoline-1-carbonyl)-amino]-2-oxo-2,3,4,7-tetrahydro-azepin-1-yl}-acetic acid methyl ester (24): To the crude product from the previous reaction, {6-[(methanesulfonyl)methyl]-3-[(isoquinoline-1-carbonyl)-amino]-2-oxo-2,3,4,7-tetrahydro-azepin-1-yl}-acetic acid methyl ester, 23, (0.147 g, 0.32 mmol) in CH₂Cl₂ (1 mL), is added benzylamine (1 mL). The reaction is stirred at room temperature for 10 minutes, then the reaction is diluted with CH₂Cl₂. The organic layer is washed with saturated NaHCO₃, saturated NaCl, and dried (Na₂SO₄). The solvent is removed in vacuo and the resulting crude material is purified by HPLC to afford 82 mg (44% yield) of the desired product as the trifluoroacetate salt. ¹H (CDCl₃) δ 8.82–8.79 (d, J=6.1 Hz, 1H), 8.61–8.59 (d, J=8.6 Hz, 1H), 8.33–8.31, (d, J=5.8 Hz, 1H), 8.01–7.99 (d, J=5.94 Hz, 1H), 7.95–7.82 (m, 2H), 7.77–7.72 (d, d, J=7.98, 7.98 Hz, 1H), 7.36–7.18 (m, 5H), 5.91 (bs, 1H), 5.40–5.39 (m, 1H), 4.67–4.61 (d, J=17.4 Hz, 1H), 4.55–4.49 (d, J=17.8 Hz, 1H), 4.19–4.05 (m, 1H), 3.88–3.83 (d, J=14.7 Hz, 1H), 3.77–3.57 (m, 3H), 3.50 (s, 3H), 2.84–2.78 (d, J=17.8 Hz, 1H), 2.50–2.40 (d, d, J=15.8, 14.5 Hz, 1H); ¹³C (CDCl₃) 171.9, 171.5, 161.9, 161.4, 160.9, 160.6, 149.1, 139.1, 135.2, 134.7, 134.2, 131.3, 130.3, 130.2, 130.1, 129.6, 128.2, 127.9, 127.8, 127.4, 125.8, 121.5, 117.7, 113.8, 110.0, 53.5, 52.9, 51.6, 49.8, 48.3, 37.9, 31.6; MS 473 (M+H)⁺.

Preparation of isoquinoline-1-carboxylic acid {6-(benzylaminomethyl)-3-[(isoquinoline-1-carbonyl)-amino-2-oxo-2,3,4,7-tetrahydro-azepin-1-yl}-acetic acid (25): A solution containing {6-(benzylamino-methyl)-3-[(isoquinoline-1-carbonyl)-amino]-2-oxo-2,3,4,7-tetrahydro-azepin-1-yl}-acetic acid methyl ester, 24, (82 mg, 0.14 mmol) in THF/H₂O (4 mL of 3:1) is treated with excess LiOH and stirred for 2.5 hours at room temperature. The solution is acidified to pH 7 and concentrated in vacuo. The residue is purified by HPLC to afford the desired product which is used directly for the next step.

Preparation of isoquinoline-1-carboxylic acid {6-(benzylamino-methyl)-1-[(2-ethoxy-5-oxo-tetrahydro-furan-3-yl-carbamoyl)-methyl]-2-oxo-2,3,4,7-tetrahydro-1H-azepin-3-yl}-amide (26): A catalytic amount of Pd(Ph₃P)₄ is added to a solution of (2-ethoxy-5-oxo-furan-3-yl)-carbamic acid allyl ester (100 mg, 0.43 mmol) and N,N-dimethylbarbituric acid (163 mg, 1.04 mmol) in CH₂Cl₂ (5 mL). The solution is stirred at room temperature for 15 minutes and then isoquinoline-1-carboxylic acid {6-(benzylaminomethyl)-3-[(isoquinoline-1-carbonyl)-amino-2-oxo-2,3,4,7-tetrahydro-azepin-1-yl}-acetic acid, 25, is added as a solution CH₂Cl₂/DMF (2 mL of 1:1), followed by HOBt (54 mg, 0.40 mmol) and EDCl (77 mg, 0.40 mmol). The solution is stirred for 5 hours, diluted with EtOAc, washed with saturated NaHCO₃ and brine, dried (Na₂SO₄), and concentrated in vacuo to provide a residue which is purified over silica (EtOAc/hexane) to afford the desired product.

The compounds of this category wherein R¹ comprises the cysteine trap 2-hydroxy-5-oxo-tetrahydrofuran-3-yl can be prepared by the procedure outlined in Scheme IX as indicated in the following example starting with compound 26.

Scheme IX

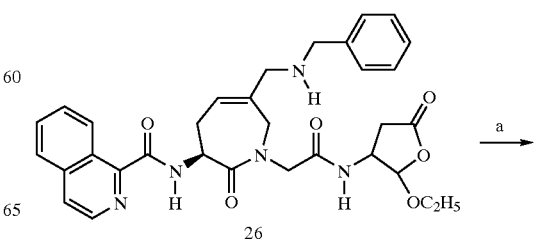

-continued

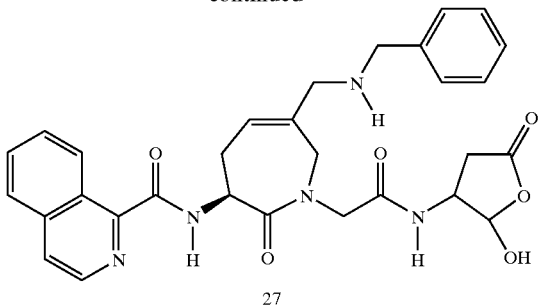

27

Reagents and conditions: (a) TFA. CH₃CN, H₂O; rt.

EXAMPLE 6

Isoquinoline-1-carboxylic acid {6-(benzylamino-methyl)-1-[(2-hydroxy-5-oxo-tetrahydro-furan-3-ylcarbamoyl)-methyl]-2-oxo-2,3,4,7-tetrahydro-1H-azepin-3-yl}-amide (27)

Preparation of isoquinoline-1-carboxylic acid {6-(benzylamino-methyl)-1-[(2-hydroxy-5-oxo-tetrahydro-furan-3-ylcarbamoyl)-methyl]-2-oxo-2,3,4,7-tetrahydro-1H-azepin-3-yl}-amide (27): Isoquinoline-1-carboxylic acid {6-(benzylamino-methyl)-1-[(2-ethoxy-5-oxo-tetrahydro-furan-3-ylcarbamoyl)-methyl]-2-oxo-2,3,4,7-tetrahydro-1H-azepin-3-yl}-amide, 26, prepared herein above, is treated with TFA in CH₃CN/H₂O. The solution is then concentrated in vacuo and the resulting residue it purified by preparative reverse phase HPLC to afford 30 mg (38% yield) of the desired product. $^1$H NMR (CD$_3$OD) δ 9.20–9.17 (d, J=8.7 Hz, 1H), 8.57–8.56 (d, J=5.7 Hz, 1H), 8.06–8.02 (m, 2H), 7.88–7.83 (d, d, d, J=8.1, 6.6, 0.9 Hz, 1H), 7.79–7.73 (d, d, d, J=6.9, 6.9, 0.9 Hz, 1H), 7.64–7.60 (m, 2H), 7.55–7.47 (m, 3H), 6.14 (bs, 1H), 5.56–5.50 (d, d, J=12.3, 3.9 Hz, 1H), 4.85–4.79 (d, d, J=16.2, 1.8 Hz, 1H), 4.66–4.62 (d, d, J=9.0, 3.6 Hz, 1H), 4.39–4.25 (m, 4H), 3.89–3.68 (m, 4H), 2.99–2.93 (m, 1H), 2.74–2.45 (m, 4H), MS 557 (M+H)$^+$.

Other non-limiting examples of compounds which comprise this aspect of Category III include:

Isoquinoline-1-carboxylic acid {1-[(2-hydroxy-5-oxo-tetrahydro-furan-3-ylcarbamoyl)-methyl]-2-oxo-6-piperidin-1-ylmethyl-2,3,4,7-tetrahydro-1H-azepin-3-yl}-amide: $^1$H NMR (CD$_3$OD) δ 9.19–9.16 (d, J=8.1 Hz, 1H), 8.57–8.55 (d, J=5.4 Hz, 1H), 8.04–8.01 (m, 2H), 7.82 (d, d, J=7.2, 6.9 Hz, 2H), 7.78–7.73 (d, d, J=7.5, 7.2 Hz, 2H), 6.16 (bs, 1H), 5.54–5.50 (d, d, J=12.9, 3.9 Hz, 1H), 4.88–4.82 (d, J=16.2 Hz, 1H), 3.91–3.57 (m, 8H), 3.02–2.81 (m, 6H), 2.73–2.55 (m, 2H), 2.04–1.54 (m, 7H).

Isoquinoline-1-carboxylic acid {1-[(2-hydroxy-5-oxo-tetrahydro-furan-3-ylcarbamoyl)-methyl]-2-oxo-6-phenylaminomethyl-2,3,4,6-tetrahydro-1H-azepin-3-yl}-amide: $^1$H NMR (CD$_3$OD) δ 9.19–9.17 (d, J=8.4 Hz, 1H), 8.57–8.55 (d, J=5.7 Hz, 1H), 8.05–8.02 (m, 2H), 7.88–7.82 (d, d, d, J=8.1, 6.9, 1.2 Hz, 2H), 7.79–7.74 (d, d, J=8.4, 6.9, 1.5 Hz, 2H), 7.54–7.48 (m, 2H), 7.42–7.33 (m, 3H), 6.00 (bs, 1H), 5.57–5.51 (d, d, J=12.9, 4.5 Hz, 1H), 4.88–4.85 (m, 1H), 4.66–4.58 (m, 2H), 4.55–4.47 (d, d, J=16.2, 6.6 Hz, 1H), 4.42–4.34 (m, 1H), 4.03–3.97 (m, 3H), 3.71–3.66 (m, 1H), 2.94–2.89 (bd, J=17.7 Hz, 1H), 2.77–2.65 (m, 1H), 2.60–2.45 (m, 2H); MS 543.9 (M+H Isoquinoline-1-carboxylic acid {6-allylaminomethyl-1-[(2-hydroxy-5-oxo-tetrahydro-furan-3-ylcarbamoyl)-methyl]-2-oxo-2,3,4,7-tetrahydro-1H-azepin-3-yl}-amide: $^1$H NMR (CD$_3$OD) δ 9.19–9.16 (d, J=8.7 Hz, 1H), 8.57–8.55 (d, J=6.0 Hz, 1H), 8.05–8.03 (m, 2H), 7.88–7.83 (d, d, J=7.8, 7.2 Hz, 1H), 7.79–7.74 (d, d, J=7.8, 7.5 Hz, 1H), 6.11–5.97 (m, 2H), 5.65–5.51 (m, 3H), 4.91–4.85 (m, 1H), 4.79–4.73 (d, d, J=15.9, 2.1 Hz, 1H), 4.67–4.62 (d, d, J=10.5, 3.6 Hz, 1H), 4.42–4.33 (m, 1H), 3.93–3.68 (m, 6H), 3.02–2.89 (m, 2H), 2.76–2.66 (m, 2H), 2.62–2.46 (m, 2H); MS 507.9 (M+H)$^+$.

Isoquinoline-1-carboxylic acid {1-[{2-hydroxy-5-oxo-tetrahydro-furan-3-ylcarbamoyl)-methyl]-6-morpholin-4-ylmethyl-2-oxo-2,3,4,7-tetrahydro-1H-azepin-3-yl}-amide: $^1$H NMR (CD$_3$OD) δ 69.18–9.15 (d, J=8.4 Hz, 1H), 8.57–8.55 (d, J=6.0 Hz, 1H), 8.05–8.02 (m, 2H), 7.87–7.82 (d, d, d, J=9.6, 6.9, 1.2 Hz, 1H), 7.78–7.73 (d, d, d, J=8.4, 6.9, 1.5 Hz, 2H), 6.18 (bs, 1H), 5.54–5.49 (d, d, J=12.6, 3.9 Hz, 1H), 4.65–4.60 (d, d, J=11.4, 3.6 Hz, 1H), 4.43–4.37 (m, 1H), 4.09–3.70 (m, 10H), 3.56–3.52 (m, 1H), 3.00–2.44 (m, 7H).

Naphthalene-2-carboxylic acid {6-(benzylamino-methyl)-1-[(2-hydroxy-5-oxo-tetrahydro-furan-3-ylcarbamoyl)-methyl]-2-oxo-2,3,4,7-tetrahydro-1H-azepin-3yl}-amide: $^1$H NMR (CD$_3$OD) δ 8.48 (s, 1H), 8.03–7.93 (m, 4H), 7.66–7.57 (m, 4H), 7.51–7.47 (m, 3H), 6.12 (bs, 1H), 5.51 (dd, J=12.6, 4.2 Hz, 1H), 4.82 (dd, J=16.5, 2.7 Hz, 1H), 4.64 (dd, J=9.6, 3.6 Hz, 1H), 4.37–4.23 (m, 3H), 3.86–3.69 (m, 4H), 2.87–2.79 (m, 1H), 2.74–2.64 (m, 2H), 2.50 (ddd, J=16.2, 7.8, 3.3 Hz, 1H); MS 557 (M+H)

Naphthalene-2-carboxylic acid {1-[(2-hydroxy-5-oxo-tetrahydro-furan-3-ylcarbamoyl)-methyl]-6-[(3-methoxy-benzylamino)-methyl]-2-oxo-2,3,4,7-tetrahydro-1H-azepin-3-yl}-amide (1q): $^1$H NMR (CD$_3$OD) δ 8.47 (s, 1H), 8.02–7.92 (m, 4H), 7.65–7.56 (m, 2H), 7.44–7.38 (d, d, J=8.4, 8.1 Hz, 1H), 7.17–7.15 (m, 2H), 7.04–7.01 (d, d, J=8.4, 1.8 Hz, 1H), 6.10 (bs, 1H), 5.52–5.46 (d, d, J=12.9, 4.5 Hz, 1H), 4.92–4.85 (m, 2H), 4.81–4.75 (d, d, J=16.2, 1.8 Hz, 1H), 4.65–4.61 (d, d, J=8.4, 3.6 Hz, 1H), 4.40–4.20 (m, 3H), 3.86 (s, 3H), 3.83–3.81 (m, 1H), 3.72 (s, 2H), 3.38 (s, 2H), 2.85–2.78 (m, 1H), 2.75–2.56 (m, 2H), 2.54–2.44 (d, d, d, J=16.2, 8.1, 3.9 Hz, 1H); MS 588 (M+H).

Naphthalene-2-carboxylic acid {1-[(2-hydroxy-5-oxo-tetrahydro-furan-3-ylcarbamoyl)-methyl]-6-[(2-methoxy-benzylamino)-methyl]-2-oxo-2,3,4,7-tetrahydro-1H-azepin-3-yl}-amide: $^1$H NMR (CD$_3$OD) δ 8.48 (s, 1H), 8.03–7.93 (m, 4H), 7.66–7.57 (m, 2H), 7.52–7.46 (m, 2H), 7.16–7.13 (d, J=9.3 Hz, 1H), 7.10–7.05 (d, d, d, J=8.4, 7.2, 0.6 Hz, 1H), 6.11 (bs, 1H), 5.54–5.48 (d, d, J=12.6, 3.9 Hz, 1H), 4.88–4.85 (m, 1H), 4.77–4.70 (d, d, J=16.2, 3.6 Hz, 1H), 4.63–4.59 (d, d, J=7.5, 3.6 Hz, 1H), 4.34–4.29 (m, 3H), 3.99 (s, 3H), 3.89–3.84 (d, J=15.9 Hz, 1H), 3.75–3.67 (d, d, J=17.4, 6.3 Hz, 1H), 3.72 (s, 2H), 2.87–2.79 (d, d, J=17.7, 3.6 Hz, 1H), 2.73–2.59 (m, 2H), 2.53–2.44 (d, d, d, J=16.5, 8.1, 3.3 Hz, 1H); MS 588 (M+H).

Naphthalene-2-carboxylic acid {1-[(2-hydroxy-5-oxo-tetrahydro-furan-3-ylcarbamoyl)-methyl]-6-[(4-methoxy-benzylamino)-methyl]-2-oxo-2,3,4,7-tetrahydro-1H-azepin-3-yl}-amide: $^1$H NMR (CD$_3$OD) δ 8.46 (s, 1H), 8.00–7.91 (m, 4H), 7.63–7.49 (m, 4H), 7.03 (m, 2H), 6.09 (bs, 1H), 5.50–5.44 (d, d, J=12.9, 4.5 Hz, 1H), 4.88 (m, 1H), 4.822–4.76 (d, d, J=16.2, 2.1 Hz, 1H), 4.66–4.62 (d, d, J=8.1, 3.6 Hz, 1H), 4.41–4.36 (m, 1H), 4.33– 4.24 (d, J=12.6 Hz, 1H), 4.18–4.14 (m, J=12.6 Hz, 1H), 3.83 (s, 3H), 3.80–3.74 (m, 2H), 3.69 (s, 2H), 2.83–2.57 (m, 3H), 2.54–2.45 (d, d, d, J=16.2, 8.1, 3.0 Hz, 1H); MS 588 (M+H).

Naphthalene-2-carboxylic acid {6-[(4-tert-butyl-benzylamino)-methyl]-1-[(2-hydroxy-5-oxo-tetrahydro-furan-3-ylcarbamoyl)-methyl]-2-oxo-2,3,4,7-tetrahydro-1H-azepin-3-yl}-amide: $^1$H NMR (CD$_3$OD) δ 8.45 (s, 1H), 8.03–7.93 (m, 4H), 7.63–7.51 (6H), 6.12 (bs, 1H), 5.53–5.47 (d, d, J=12.9, 4.5 Hz, 1H), 4.85–4.80 (d, J=16.5 Hz, 1H), 4.86–4.62 (d, d, J=12.3, 3.9 Hz, 1H), 4.39–4.20 (m, 3H), 3.86–3.77 (m, 2H), 3.73 (s, 2H), 2.87–2.79 (d, d, J=18.6, 3.3 Hz, 1H), 2.74–2.65 (m, 2H), 2.54–2.45 (d, d, d, J=15.9, 8.1, 4.2 Hz, 1H), 1.36 (s, 9H); MS 613 (M+H).

Naphthalene-2-carboxylic acid {1-[(2-hydroxy-5-oxo-tetrahydro-furan-3-ylcarbamoyl)-methyl]-6-[(2-methyl-benzylamino)-methyl]-2-oxo-2,3,4,7,-tetrahydro-1H-azepin-3-yl}-amide: $^1$H NMR (CD$_3$OD) δ 8.46 (s, 1H), 8.00–7.91 (m, 4H), 7.63–7.55 (m, 3H), 7.35–7.28 (m, 3H), 6.13 (bs, 1H), 5.51–5.46 (d, d, J=12.9, 3.9 Hz, 1H), 4.91–4.85 (m, 1H), 4.83–4.76 (d, d, J=16.2, 3.3, Hz, 1H), 4.64–4.60 (d, d, J=6.9, 3.6 Hz, 1H), 4.38–4.26 (m, 3H), 3.87–3.73 (m, 4H), 2.85–2.77 (d, d, J=18.9, 3.9 Hz, 1H), 2.73–2.63 (m, 2H), 2.53–2.50 (d, d, J=8.1, 3.0 Hz, 1H), 2.46 (s, 3H); MS 571 (M+H).

Naphthalene-2-carboxylic acid {1-[(2-hydroxy-5-oxo-tetrahydro-furan-3-ylcarbamoyl)-methyl]-6-[(3-methyl-benzylamino)-methyl]-2-oxo-2,3,4,7-tetrahydro-1H-azepin-3-yl}-amide: $^1$H NMR (CD$_3$OD) δ 8.46 (s, 1H), 8.00–7.91 (m, 4H), 7.63–7.54 (m, 2H), 7.40–7.34 (m, 3H), 7.28–7.25 (m, 1H), 6.09 (bs, 1H), 5.50–5.44 (d, d, J=12.9, 4.5 Hz, 1H), 4.91–4.82 (m, 1H), 4.80–4.74 (d, d, J=16.5, 1.5 Hz, 1H), 4.65–4.61 (d, d, J=7.8, 3.6 Hz, 1H), 4.42–4.33 (m, 1H), 4.30–4.26 (d, J=12.9 Hz, 1H), 4.21–4.17 (d, J=12.9 Hz, 1H), 3.88–3.82 (d, d, J=16.2, 2.7 Hz, 1H), 3.78–3.75 (d, J=9.9 Hz, 1H), 3.71 (s, 2H), 2.83–2.76 (d, d, J=18.9, 3.9 Hz, 1H), 2.77–2.63 (m, 2H), 2.565–2.45 (d, d, d, J=16.2, 8.1, 3.3 Hz, 1H), 2.40 (s, 3H); MS 571 (M+H).

Naphthalene-2-carboxylic acid {1-[(2-hydroxy-5-oxo-tetrahydro-furan-3-ylcarbamoyl)-methyl]-6-[(4-methyl-benzylamino)-methyl]-2-oxo-2,3,4,7-tetrahydro-1H-azepin-3-yl}-amide): $^1$H NMR (CD$_3$OD) δ 8.47 (s, 1H), 8.02–7.93 (m, 4H), 7.65–7.56 (m, 2H), 7.49–7.46 (d, J=8.1 Hz, 2H), 7.33–7.30 (d, J=8.1 Hz, 2H), 6.10 (bs, 1H), 5.52–5.46 (d, d, J=12.9, 4.5 Hz, 1H), 4.88–4.87 (m, 1H), 4.85–4.77 (d, d, J=16.5, 4.2 Hz, 1H), 4.66–4.62 (d, d, J=9.3, 3.6 Hz, 1H), 4.39–4.33 (m, 1H), 4.31–4.27 (d, J=12.9 Hz, 1H), 4.22–4.18 (d, J=12.9 Hz, 1H), 3.87–3.70 (d, d, J=16.2, 2.4 Hz, 1H), 3.78–3.75 (d, J=9.0 Hz, 1H), 3.71 (s, 2H), 2.85–2.78 (d, d, J=17.7, 3.6 Hz, 1H), 2.74–2.65 (m, 2H), 2.54–2.48 (d, d, d, J=16.5, 8.1, 3.6 Hz, 1H); 2.39 (s, 3H); MS 571 (M+H).

Naphthalene-2-carboxylic acid {1-[(2-hydroxy-5-oxo-tetrahydro-furan-3-ylcarbamoyl)-methyl]-6-[(4-methanesulfonyl-benzylamino)-methyl]-2-oxo-2,3,4,7-tetrahydro-1H-azepin-3-yl}-amide: $^1$H NMR (CD$_3$OD) δ 8.48 (s, 1H), 8.11–8.08 (d, J=8.1 Hz, 2H), 8.03–7.87 (m, 6H), 7.65–7.57 (m, 2H), 6.17 (bs, 1H), 5.54–5.48 (d, d, J=12.9, 4.5 Hz, 1H), 4.96–4.93 (m, 1H), 4.63–4.58 (d, d, J=12.3, 3.9 Hz, 1H), 4.51–4.47 (d, J=13.2 Hz, 1H), 4.39–4.35 (d, J=13.2 Hz, 1H), 4.33–4.28 (m, 1H), 3.87–3.76 (m, 5H), 3.18 (s, 3H), 2.88–2.81 (d, d, J=16.8, 2.4 Hz, 1H), 2.72–2.60 (m, 2H), 2.51–2.41 (d, d, d, J=16.2, 7.8, 4.5 Hz, 1H); MS 634.34 (M+H).

Naphthalene-2-carboxylic acid {1-[(2-hydroxy-5-oxo-tetrahydro-furan-3-ylcarbamoyl)-methyl]-2-oxo-6-[(4-[1,2,3]thiadiazol-4-yl-benzylamino)-methyl]-2,3,4,7-tetrahydro-1H-azepin-3-yl}-amide: $^1$H NMR (CD$_3$OD) 67 9.36 (s, 1H), 8.49 (s, 1H), 8.28–8.26 (d, J=8.1 Hz, 2H), 8.04–7.98 (m, 4H), 7.81–7.79 (d, J=7.5 Hz, 2H), 7.66–7.62 (m, 2H), 6.18 (bs, 1H), 5.56–5.50 (d, d, J=4.8, 15.3 Hz, 1H), 4.97–4.92 (m, 1H), 4.66–4.61 (d, d, J=3.3, 1.7 Hz, 1H), 4.47–4.32 (m, 3H), 3.83–3.79 (m, 5H), 2.88–2.83 (d, J=15.6 Hz, 1H), 2.72–2.67 (m, 2H), 2.52–2.43 (d, d, d, J=20.1, 7.5, 3.9 Hz, 1H); MS 640.77 (M+H).

Naphthalene-2-carboxylic acid {1-[(2-hydroxy-5-oxo-tetrahydro-furan-3-ylcarbamoyl)-methyl]-6-[(4-isopropyl-benzylamino)-methyl]-2-oxo-2,3,4,7-tetrahydro-1H-azepin-3-yl}-amide: $^1$H NMR (CD$_3$OD) δ 8.49 (s, 1H), 8.04–8.93 (m, 4H), 7.64–7.60 (m, 2H), 7.54–7.52 (d, J=7.2 Hz, 2H), 7.41–7.38 (d, J=8.1 Hz, 2H), 6.12 (bs, 1H), 5.54–5.48 (d, d, J=12.6, 4.2 Hz, 1H), 4.96–4.94 (m, 1H), 4.82–4.81 (d, J=1.8 Hz, 1H), 4.68–4.62 (d, d, J=12.3, 3.9 Hz, 1H), 4.40–4.33 (m, 1H), 4.29–4.20 (m, 2H), 3.84–3.78 (m, 2H), 3.73 (s, 2H), 3.03–2.93 (septet, J=6.9 Hz, 1H), 2.86–2.80 (d, d, J=17.7, 3.6 Hz, 1H), 2.74–2.64 (m, 2H), 2.54–2.45 (d, d, d, J=4.5, 7.8, 16.2 Hz, 1H), 1.30–1.28 (d, J=6.9 Hz, 6H); MS 597.80 (M+H).

Naphthalene-2-carboxylic acid {1-[(2-hydroxy-5-oxo-tetrahydro-furan-3-ylcarbamoyl)-methyl]-2-oxo-6-[(4-pentyl-benzylamino)-methyl]-2,3,4,7-tetrahydro-1H-azepin-3-yl}-amide: $^1$H NMR (CD$_3$OD) δ 8.48 (s, 1H), 8.03–7.93 (m, 4H), 7.66–7.59 (m, 2H), 7.52–7.49 (d, J=7.2 Hz, 2H), 7.34–7.32 (d, J=8.1 Hz, 1H), 6.11 (bs, 1H), 5.53–5.47 (d, d, J=12.6, 4.2 Hz, 1H), 4.85–4.79 (d, d, J=16.2, 2.1 Hz, 1h), 4.67–4.62 (d, d, J=10.5, 3.6 Hz, 1H), 4.42–4.34 (m, 1H), 4.32–4.28 (d, J=12.9 Hz, 1H), 4.24–4.19 (d, J=12.9 Hz, 1H), 3.86–3.79 (d, d, J=16.5, 3.0 Hz, 1H), 3.76–3.67 (m, 3H), 3.41–3.38 (m, 1H), 2.88–2.79 (d, d, J=18.3, 3.6 Hz, 1H), 2.74–2.65 (m, 4H), 2.54–2.45 (d, d, d, J=16.2, 8.1, 4.2 Hz, 1H), 1.71–1.61 (m, 2H), 1.42–1.32 (m, 4H), 0.95–0.90 (t, J=6.9 Hz, 3H); MS 627 (M+H).

The third aspect of Category III comprises scaffolds having the formula:

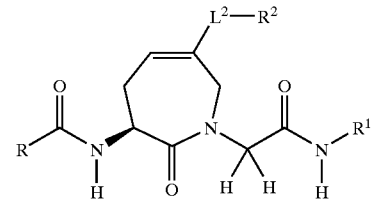

wherein R, R$^1$, L$^2$ and R$^2$ are described herein below in Table V.

TABLE V

| No. | R | R$^1$ | —L$^2$—R$^2$ |
|---|---|---|---|
| 313 | phenyl | 2-hydroxy-5-oxo-tetrahydrofuran-3-yl | —CH$_2$NHCOC$_6$H$_5$ |
| 314 | 2-naphthyl | 2-hydroxy-5-oxo-tetrahydrofuran-3-yl | —CH$_2$NHCOC$_6$H$_5$ |

TABLE V-continued

| No. | R | R¹ | —L²—R² |
|---|---|---|---|
| 315 | 1-isoquinolinyl | 2-hydroxy-5-oxo-tetrahydrofuran-3-yl | —CH$_2$NHCOC$_6$H$_5$ |
| 316 | phenyl | 2-hydroxy-5-oxo-tetrahydrofuran-3-yl | —CH$_2$NHCO[4-CH(CH$_3$)$_2$C$_6$H$_4$] |
| 317 | 2-naphthyl | 2-hydroxy-5-oxo-tetrahydrofuran-3-yl | —CH$_2$NHCO[4-CH(CH$_3$)$_2$C$_6$H$_4$] |
| 318 | 1-isoquinolinyl | 2-hydroxy-5-oxo-tetrahydrofuran-3-yl | —CH$_2$NHCO[4-CH(CH$_3$)$_2$C$_6$H$_4$] |
| 319 | phenyl | 2-hydroxy-5-oxo-tetrahydrofuran-3-yl | —CH$_2$NHCO(4-n-pentylC$_6$H$_4$) |
| 320 | 2-naphthyl | 2-hydroxy-5-oxo-tetrahydrofuran-3-yl | —CH$_2$NHCO(4-n-pentylC$_6$H$_4$) |
| 321 | 1-isoquinolinyl | 2-hydroxy-5-oxo-tetrahydrofuran-3-yl | —CH$_2$NHCO(4-n-pentylC$_6$H$_4$) |
| 322 | phenyl | 2-hydroxy-5-oxo-tetrahydrofuran-3-yl | —CH$_2$NHCO(2-FC$_6$H$_4$) |
| 323 | 2-naphthyl | 2-hydroxy-5-oxo-tetrahydrofuran-3-yl | —CH$_2$NHCO(2-FC$_6$H$_4$) |
| 324 | 1-isoquinolinyl | 2-hydroxy-5-oxo-tetrahydrofuran-3-yl | —CH$_2$NHCO(2-FC$_6$H$_4$) |
| 325 | phenyl | 2-hydroxy-5-oxo-tetrahydrofuran-3-yl | —CH$_2$NHCO(3-FC$_6$H$_4$) |
| 326 | 2-naphthyl | 2-hydroxy-5-oxo-tetrahydrofuran-3-yl | —CH$_2$NHCO(3-FC$_6$H$_4$) |
| 327 | 1-isoquinolinyl | 2-hydroxy-5-oxo-tetrahydrofuran-3-yl | —CH$_2$NHCO(3-FC$_6$H$_4$) |
| 328 | phenyl | 2-hydroxy-5-oxo-tetrahydrofuran-3-yl | —CH$_2$NHCO(4-FC$_6$H$_4$) |
| 329 | 2-naphthyl | 2-hydroxy-5-oxo-tetrahydrofuran-3-yl | —CH$_2$NHCO(4-FC$_6$H$_4$) |
| 330 | 1-isoquinolinyl | 2-hydroxy-5-oxo-tetrahydrofuran-3-yl | —CH$_2$NHCO(4-FC$_6$H$_4$) |
| 331 | phenyl | 2-hydroxy-5-oxo-tetrahydrofuran-3-yl | —CH$_2$NHCO(2-CH$_3$C$_6$H$_4$) |
| 332 | 2-naphthyl | 2-hydroxy-5-oxo-tetrahydrofuran-3-yl | —CH$_2$NHCO(2-CH$_3$C$_6$H$_4$) |
| 333 | 1-isoquinolinyl | 2-hydroxy-5-oxo-tetrahydrofuran-3-yl | —CH$_2$NHCO(2-CH$_3$C$_6$H$_4$) |
| 334 | phenyl | 2-hydroxy-5-oxo-tetrahydrofuran-3-yl | —CH$_2$NHCO(3-CH$_3$C$_6$H$_4$) |
| 335 | 2-naphthyl | 2-hydroxy-5-oxo-tetrahydrofuran-3-yl | —CH$_2$NHCO(3-CH$_3$C$_6$H$_4$) |
| 336 | 1-isoquinolinyl | 2-hydroxy-5-oxo-tetrahydrofuran-3-yl | —CH$_2$NHCO(3-CH$_3$C$_6$H$_4$) |
| 337 | phenyl | 2-hydroxy-5-oxo-tetrahydrofuran-3-yl | —CH$_2$NHCO(4-CH$_3$C$_6$H$_4$) |
| 338 | 2-naphthyl | 2-hydroxy-5-oxo-tetrahydrofuran-3-yl | —CH$_2$NHCO(4-CH$_3$C$_6$H$_4$) |
| 339 | 1-isoquinolinyl | 2-hydroxy-5-oxo-tetrahydrofuran-3-yl | —CH$_2$NHCO(4-CH$_3$C$_6$H$_4$) |
| 340 | phenyl | 2-hydroxy-5-oxo-tetrahydrofuran-3-yl | —CH$_2$NHCO(2-OCH$_3$C$_6$H$_4$) |
| 341 | 2-naphthyl | 2-hydroxy-5-oxo-tetrahydrofuran-3-yl | —CH$_2$NHCO(2-OCH$_3$C$_6$H$_4$) |
| 342 | 1-isoquinolinyl | 2-hydroxy-5-oxo-tetrahydrofuran-3-yl | —CH$_2$NHCO(2-OCH$_3$C$_6$H$_4$) |
| 343 | phenyl | 2-hydroxy-5-oxo-tetrahydrofuran-3-yl | —CH$_2$NHCO(3-OCH$_3$C$_6$H$_4$) |
| 344 | 2-naphthyl | 2-hydroxy-5-oxo-tetrahydrofuran-3-yl | —CH$_2$NHCO(3-OCH$_3$C$_6$H$_4$) |
| 345 | 1-isoquinolinyl | 2-hydroxy-5-oxo-tetrahydrofuran-3-yl | —CH$_2$NHCO(3-OCH$_3$C$_6$H$_4$) |
| 346 | phenyl | 2-hydroxy-5-oxo-tetrahydrofuran-3-yl | —CH$_2$NHCO(4-OCH$_3$C$_6$H$_4$) |
| 347 | 2-naphthyl | 2-hydroxy-5-oxo-tetrahydrofuran-3-yl | —CH$_2$NHCO(4-OCH$_3$C$_6$H$_4$) |
| 348 | 1-isoquinolinyl | 2-hydroxy-5-oxo-tetrahydrofuran-3-yl | —CH$_2$NHCO(4-OCH$_3$C$_6$H$_4$) |
| 349 | 1-isoquinolinyl | 2-ethoxy-5-oxo-tetrahydrofuran-3-yl | —CH$_2$NHCOC$_6$H$_5$ |
| 350 | phenyl | 2-ethoxy-5-oxo-tetrahydrofuran-3-yl | —CH$_2$NHCOC$_6$H$_5$ |
| 351 | 2-naphthyl | 2-ethoxy-5-oxo-tetrahydrofuran-3-yl | —CH$_2$NHCOC$_6$H$_5$ |
| 352 | 1-isoquinolinyl | 2-ethoxy-5-oxo-tetrahydrofuran-3-yl | —CH$_2$NHCO[4-CH(CH$_3$)$_2$C$_6$H$_4$] |
| 353 | phenyl | 2-ethoxy-5-oxo-tetrahydrofuran-3-yl | —CH$_2$NHCO[4-CH(CH$_3$)$_2$C$_6$H$_4$] |
| 354 | 2-naphthyl | 2-ethoxy-5-oxo-tetrahydrofuran-3-yl | —CH$_2$NHCO[4-CH(CH$_3$)$_2$C$_6$H$_4$] |
| 355 | 1-isoquinolinyl | 2-ethoxy-5-oxo-tetrahydrofuran-3-yl | —CH$_2$NHCO(4-n-pentylC$_6$H$_4$) |
| 356 | phenyl | 2-ethoxy-5-oxo-tetrahydrofuran-3-yl | —CH$_2$NHCO(4-n-pentylC$_6$H$_4$) |
| 357 | 2-naphthyl | 2-ethoxy-5-oxo-tetrahydrofuran-3-yl | —CH$_2$NHCO(4-n-pentylC$_6$H$_4$) |
| 358 | 1-isoquinolinyl | 2-ethoxy-5-oxo-tetrahydrofuran-3-yl | —CH$_2$NHCO(2-FC$_6$H$_4$) |
| 359 | phenyl | 2-ethoxy-5-oxo-tetrahydrofuran-3-yl | —CH$_2$NHCO(2-FC$_6$H$_4$) |
| 360 | 2-naphthyl | 2-ethoxy-5-oxo-tetrahydrofuran-3-yl | —CH$_2$NHCO(2-FC$_6$H$_4$) |
| 361 | 1-isoquinolinyl | 2-ethoxy-5-oxo-tetrahydrofuran-3-yl | —CH$_2$NHCO(3-FC$_6$H$_4$) |
| 362 | phenyl | 2-ethoxy-5-oxo-tetrahydrofuran-3-yl | —CH$_2$NHCO(3-FC$_6$H$_4$) |
| 363 | 2-naphthyl | 2-ethoxy-5-oxo-tetrahydrofuran-3-yl | —CH$_2$NHCO(3-FC$_6$H$_4$) |
| 364 | 1-isoquinolinyl | 2-ethoxy-5-oxo-tetrahydrofuran-3-yl | —CH$_2$NHCO(4-FC$_6$H$_4$) |
| 365 | phenyl | 2-ethoxy-5-oxo-tetrahydrofuran-3-yl | —CH$_2$NHCO(4-FC$_6$H$_4$) |
| 366 | 2-naphthyl | 2-ethoxy-5-oxo-tetrahydrofuran-3-yl | —CH$_2$NHCO(4-FC$_6$H$_4$) |
| 367 | 1-isoquinolinyl | 2-ethoxy-5-oxo-tetrahydrofuran-3-yl | —CH$_2$NHCO(2-CH$_3$C$_6$H$_4$) |
| 368 | phenyl | 2-ethoxy-5-oxo-tetrahydrofuran-3-yl | —CH$_2$NHCO(2-CH$_3$C$_6$H$_4$) |
| 369 | 2-naphthyl | 2-ethoxy-5-oxo-tetrahydrofuran-3-yl | —CH$_2$NHCO(2-CH$_3$C$_6$H$_4$) |
| 370 | 1-isoquinolinyl | 2-ethoxy-5-oxo-tetrahydrofuran-3-yl | —CH$_2$NHCO(3-CH$_3$C$_6$H$_4$) |
| 371 | phenyl | 2-ethoxy-5-oxo-tetrahydrofuran-3-yl | —CH$_2$NHCO(3-CH$_3$C$_6$H$_4$) |
| 372 | 2-naphthyl | 2-ethoxy-5-oxo-tetrahydrofuran-3-yl | —CH$_2$NHCO(3-CH$_3$C$_6$H$_4$) |
| 373 | 1-isoquinolinyl | 2-ethoxy-5-oxo-tetrahydrofuran-3-yl | —CH$_2$NHCO(4-CH$_3$C$_6$H$_4$) |
| 374 | phenyl | 2-ethoxy-5-oxo-tetrahydrofuran-3-yl | —CH$_2$NHCO(4-CH$_3$C$_6$H$_4$) |
| 375 | 2-naphthyl | 2-ethoxy-5-oxo-tetrahydrofuran-3-yl | —CH$_2$NHCO(4-CH$_3$C$_6$H$_4$) |
| 376 | 1-isoquinolinyl | 2-ethoxy-5-oxo-tetrahydrofuran-3-yl | —CH$_2$NHCO(2-OCH$_3$C$_6$H$_4$) |
| 377 | phenyl | 2-ethoxy-5-oxo-tetrahydrofuran-3-yl | —CH$_2$NHCO(2-OCH$_3$C$_6$H$_4$) |
| 378 | 2-naphthyl | 2-ethoxy-5-oxo-tetrahydrofuran-3-yl | —CH$_2$NHCO(2-OCH$_3$C$_6$H$_4$) |
| 379 | 1-isoquinolinyl | 2-ethoxy-5-oxo-tetrahydrofuran-3-yl | —CH$_2$NHCO(3-OCH$_3$C$_6$H$_4$) |
| 380 | phenyl | 2-ethoxy-5-oxo-tetrahydrofuran-3-yl | —CH$_2$NHCO(3-OCH$_3$C$_6$H$_4$) |
| 381 | 2-naphthyl | 2-ethoxy-5-oxo-tetrahydrofuran-3-yl | —CH$_2$NHCO(3-OCH$_3$C$_6$H$_4$) |
| 382 | 1-isoquinolinyl | 2-ethoxy-5-oxo-tetrahydrofuran-3-yl | —CH$_2$NHCO(4-OCH$_3$C$_6$H$_4$) |
| 383 | phenyl | 2-ethoxy-5-oxo-tetrahydrofuran-3-yl | —CH$_2$NHCO(4-OCH$_3$C$_6$H$_4$) |
| 384 | 2-naphthyl | 2-ethoxy-5-oxo-tetrahydrofuran-3-yl | —CH$_2$NHCO(4-OCH$_3$C$_6$H$_4$) |

The compounds of the third aspect of Category III can be suitably prepared by the procedure outlined herein below, utilizing intermediates such as 23 as a starting point which can be synthesized by the procedure described in Scheme VIII.

Scheme X

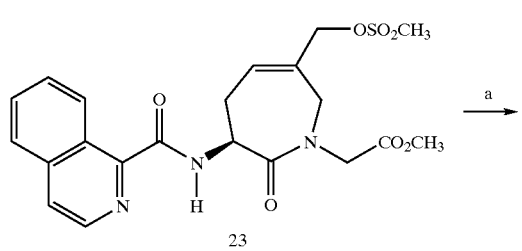
23 a →

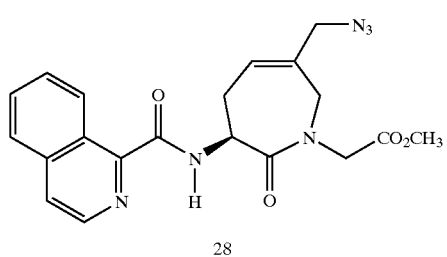
28

Reagents and conditions: a) NaN₃, DMF; 50° C., 18 hr.

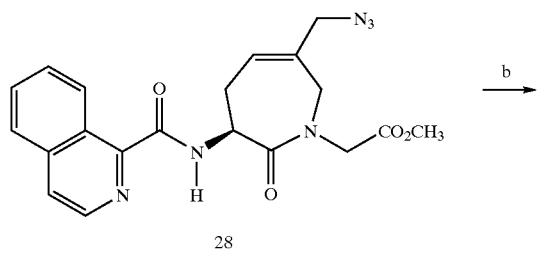
28 b →

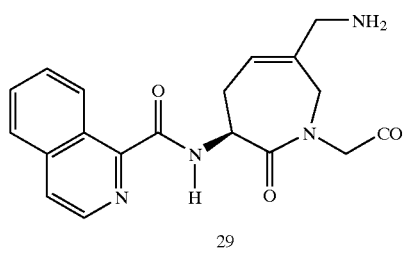
29

Reagents and conditions: b) Ph₃P, H₂O, THF; rt, 18 hr.

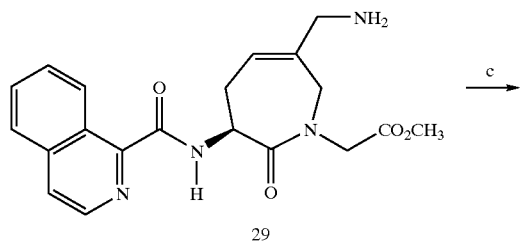
29 c →

-continued

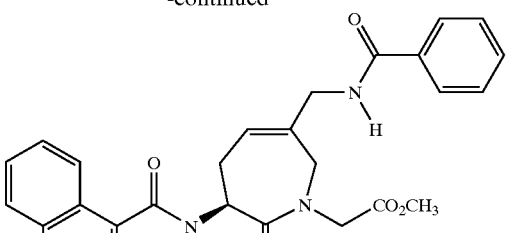
30

Reagents and conditions: c) PhCOCl, Et₃N, THF; rt.

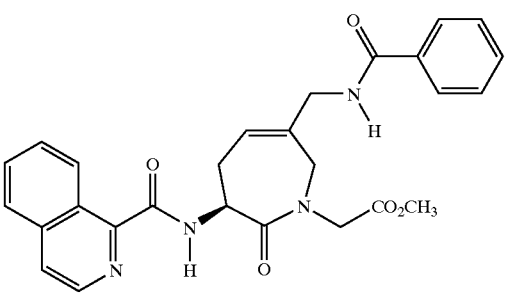
30 d →

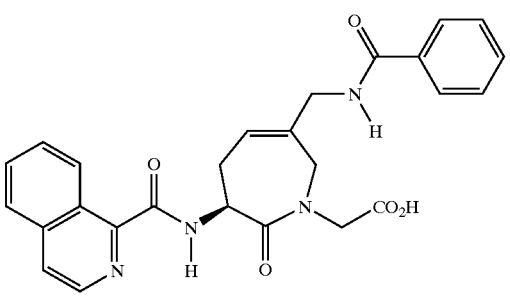
31

Reagents and conditions: d) LiOH, THF/H₂O, rt, 2.5 hrs.

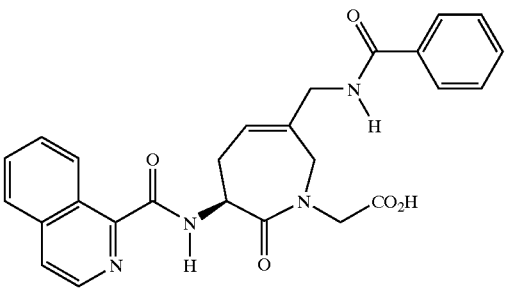
31 e →

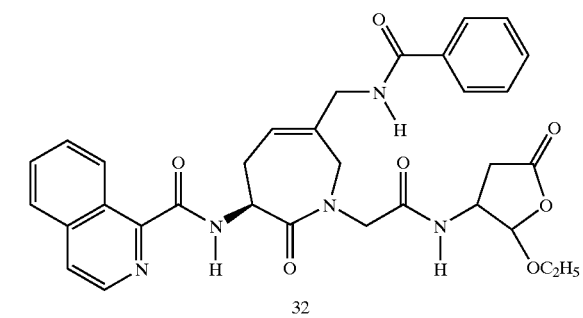
32

-continued

Reagents and conditions: e) (2-ethoxy-5-oxo-tetrahydrofurany-3-yl)-carbamic acid allyl ester; N,N-dimethylbarbituric acid, (Ph₃P)₄Pd, CH₂Cl₂, EDCl, HOBt

EXAMPLE 7

Isoquinoline-1-carboxylic acid {6-(benzenesulfony-lamino-methyl)-1-[(2-hydroxy-5-oxo-tretrahydro-furan-3-ylcarbamoyl)-methyl]-2-oxo-2,3,4,7-tetrahydro-1H-azepin-3-yl}-amide (32)

Preparation of {6-azidomethyl-3-[(isoquinoline-1-carbonyl)-amino]-2-oxo-2,3,4,7-tetrahydro-azepin-1-yl}-acetic methyl ester (28): To a solution of {6-[(methane-sulfonyl)methyl]-3-[(isoquinoline-1-carbonyl)-amino]-2-oxo-2,3,4,7-tetrahydro-azepin-1-yl}-acetic acid methyl ester, 23, (1.62 g, 3.52 mmol) in DMF(10 mL) is added sodium azide at room temperature. The reaction is then heated to 50° C. and stirred 18 hours after which time the solution is diluted with water. The resulting solution is extracted three times with CH₂Cl₂ (70 mL), the organic layers combined and washed with saturated NaHCO₃, saturated NaCl, and dried (Na₂SO₄). The solvent is removed in vacuo and the resulting residue is purified by HPLC to afford 0.46 g (59% yield) of the desired product. ¹H NMR (CDCl₃) δ 9.49–9.46 (m, 1H), 9.21–9.19 (d, J=6.9 Hz, 1H), 8.48–8.46 (m, 1H), 7.81–7.74 (m, 2H), 7.69–7.60 (m, 2H), 5.83–5.81 (m, 1H), 5.51–5.43 (m, 1H), 4.76–4.69 d, d, J=17.4, 2.4 Hz, 1H), 4.46–4.40 (d, J=17.4 Hz, 1H), 4.20–4.14 (d, J=17.7 Hz, 1H), 3.84–3.76 (d, J=13.2 Hz, 1H), 3.74–3.70 (m, 3H), 3.68–3.64 (d, J=13.2 Hz, 1H), 3.44–3.39 d, J=17.7 Hz, 1H), 2.99–2.92 (d, d, J=18.3, 3.9 Hz, 1H), 2.50–2.40 (d, d, J=15.6, 14.7 Hz, 1H); MS 409 (M+H)⁺.

Preparation of {6-(aminomethyl)-3-[(isoquinoline-1-carbonyl)-amino-2-oxo-2,3,4,7-tetrahydro-azepin-1-yl}-acetic acid methyl ester (29): A solution of {6-azidomethyl-3-[(isoquinoline-1-carbonyl)-amino]-2-oxo-2,3,4,7-tetrahydro-azepin-1-yl}-acetic methyl ester, 28, (0.46 g, 1.12 mmol) in THF (10 mL) and 5 drops of water is treated with triphenylphosphine (0.6 g, 2.25 mmol) at room temperature. The solution is stirred for 18 hours after which the solvent is solvent is removed in vacuo and the resulting residue is purified by HPLC to afford the desired product which is immediately used for the next step.

Preparation of {6-(benzoylamino-methyl)-3-[(isoquinoline-1-carbonyl)-amino]-2-oxo-2,3,4,7-tetrahydro-azepin-1-yl}-acetic acid methyl ester (30): To a solution of {6-(aminomethyl)-3-[(isoquinoline-1-carbonyl)-amino]-2-oxo-2,3,4,7-tetrahydro-azepin-1-yl}-acetic acid methyl ester, 29, (0.14 g, 0.37 mmol) in THF(1 mL) is added benzoyl chloride (80 μl, 0.75 mmol) and triethyl amine (0.71 mL, 4.99 mmol). The reaction is complete with a few minutes. Methanol (5 mL) is added to the reaction mixture and then the solvents are removed in vacuo to provide a residue which is purified by HPLC to afford 84 mg (46% yield) of the desired product. ¹H NMR (CDCl₃) δ 9.37–9.33 (d, J=9.4 Hz, 1H), 9.06–9.03 (d, J=5.5 Hz, 1H), 7.73–7.64 (m, 4H), 7.59–7.48 (m, 2H), 7.41–7.48 (m, 4H), 5.68 (bs, 1H), 5.37–5.30 (m, 1H), 4.644.57 (d, d, J=17.5, 2.37 Hz, 1H), 4.4.6–4.40 (d, J=17.6 Hz, 1H), 4.15–4.08 (d, d, J=14.5, 6.9 Hz, 1H), 3.82–3.76 (d, J=17.6 Hz, 1H), 3.76–3.70 (d, d, J=14.7 Hz, 1H), 3.42 (s, 3H), 3.38–3.33 (d, J=17.6 Hz, 1H), 2.81–2.76 (m, 1H), 2.35–2.25 (d, d, J=16.3, 14.2 Hz, 1H); ¹³C (CDCl₃) 172.6, 170.5, 168.0, 165.9, 148.2, 141.0, 137.7, 134.3, 133.8, 132.4, 132.3, 132.0, 130.7, 129.0, 128.9, 127.7, 127.6, 127.5, 127.2, 124.7, 52.6, 50.5, 49.3, 49.1, 46.7, 32.6; MS 487 (M+H).

Preparation of {6-(benzoylamino-methyl)-3-[(isoquinoline-1-carbonyl)-amino]-2-oxo-2,3,4,7-tetrahydro-azepin-1-yl}-acetic acid (31): A solution containing {6-(benzoylamino-methyl)-3-[(isoquinoline-1-carbonyl)-amino]-2-oxo-2,3,4,7-tetrahydro-azepin-1-yl}-acetic acid methyl ester, 30, (84 mg, 0.17 mmol) in THF/H₂O (4 mL of 3:1) is treated with excess LiOH and the solution stirred for 2.5 hours at room temperature. The solution is then acidified and extracted with EtOAc. The EtOAc layer was dried (Na₂SO₄) and concentrated to the crude product which is used without further purification.

Preparation of isoquinoline-1-carboxylic acid {6-(benzoylamino-methyl)-1-[(2-ethoxy-5-oxo-tetrahydro-furan-3-ylcarbamoyl)-methyl]-2-oxo-2,3,4,7,-tetrahydro-1H-azepin-3-yl}-amide (32): A catalytic amount of Pd(Ph₃P)₄ is added to a solution of (2-ethoxy-5-oxo-furan-3-yl)-carbamic acid allyl ester (100 mg, 0.43 mmol) and N,N-dimethylbarbituric acid (135 mg, 0.86 mmol) in CH₂Cl₂ (5 mL). The solution is stirred at room temperature for 15 minutes then {6-(benzoylamino-methyl)-3-[(isoquinoline-1-carbonyl)-amino]-2-oxo-2,3,4,7-tetrahydro-azepin-1-yl}-acetic acid, 31, prepared in the previous step, is dissolved in CH₂Cl₂/DMF (2 mL of 1:1) and added. HOBt (54 mg, 0.40 mmol) and EDCl (77 mg, 0.40 mmol) are added and the solution stirred for 5 hours after which time it is diluted with EtOAc, washed with saturated NaHCO₃ and brine, dried (Na₂SO₄), and concentrated in vacuo. The resulting residue is purified over silica (EtOAc/hexane) to afford the desired product.

The compounds of this category wherein R¹ comprises the cysteine trap 2-hydroxy-5-oxo-tetrahydrofuran-3-yl can be prepared by the procedure outlined in Scheme XI as indicated in the following example starting with compound 32.

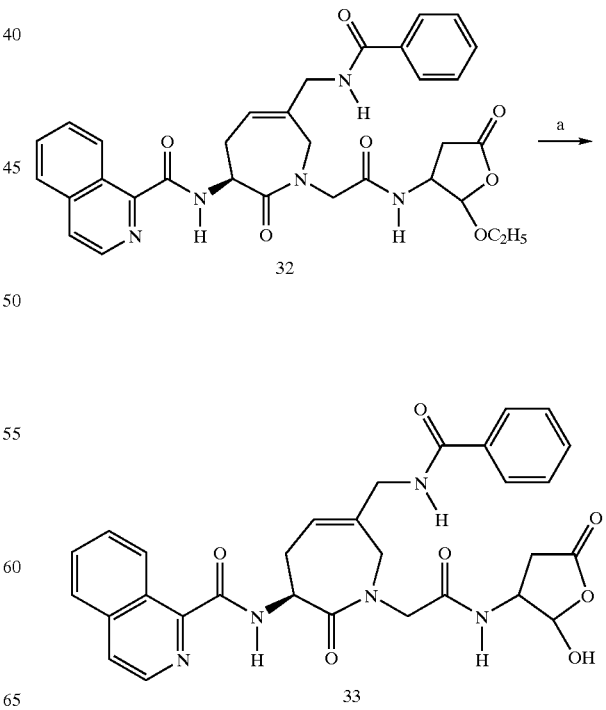

Scheme XI

Reagents and conditions: (a) TFA. CH₃CN, H₂O; rt.

EXAMPLE 8

Isoquinoline-1-carboxylic acid {6-(benzoylamino-methyl)-1-[(2-hydroxy-5-oxo-tetrahydro-furan-3-ylcarbamoyl)-methyl]-2-oxo-2,3,4,7,-tetrahydro-1H-azepin-3-yl}-amide (33)

Preparation of isoquinoline-1-carboxylic acid {6-(benzoylamino-methyl)-1-[(2-hydroxy-5-oxo-tetrahydro-furan-3-ylcarbamoyl)-methyl]-2-oxo-2,3,4,7,-tetrahydro-1H-azepin-3-yl}-amide (33): A solution of isoquinoline-1-carboxylic acid {6-(benzoylamino-methyl)-1-[(2-ethoxy-5-oxo-tetrahydro-furan-3-ylcarbamoyl)-methyl]-2-oxo-2,3,4,7,-tetrahydro-1H-azepin-3-yl}-amide, 32, as prepared in the above example, in $CH_3CN/H_2O$ is treated with excess trifluoroacetic acid. The solution is stirred several hours then purified by preparative reverse phase HPLC to afford 51 mg (51% yield) of the desired product. $^1$H NMR ($CD_3OD$) δ 9.15–9.12 (d, J=8.4 Hz, 1H), 8.56–8.54 (d, J=5.7 Hz, 1H), 8.08–8.04 (m, 2H), 7.92–7.76 (m, 4H), 7.57–7.50 (m, 3H), 5.83 (bs, 1H), 5.61–5.56 (d, d, J=12.6, 3.9 Hz, 1H), 4.90–4.85 (d, J=17.4 Hz, 1H), 4.63–4.60 (m, 1H), 4.41–4.01 (m, 3H), 3.65–3.58 (d, d, J=17.4, 2.7 Hz, 1H), 2.91–2.85 (bd, J=18.9 Hz, 1H), 2.75–2.65 (m, 1H), 2.55–2.46 (m, 2H); MS 572 (M+H).

Other non-limiting examples of compounds which comprise this aspect of Category III include:

Naphthalene-2-carboxylic acid {1-[(2-hydroxy-5-oxo-tetrahydro-furan-3-ylcarbamoyl)-methyl]-6-[(3-methoxy-benzylamino)-methyl]-2-oxo-2,3,4,7-tetrahydro-1H-azepin-3-yl}-amide: $^1$H NMR ($CD_3OD$) δ 8.47 (s, 1H), 8.02–7.92 (m, 4H), 7.65–7.56 (m, 2H), 7.44–7.38 (d, d, J=8.4, 8.1 Hz, 1H), 7.17–7.15 (m, 2H), 7.04–7.01 (d, d, J=8.4, 1.8 Hz, 1H), 6.10 (bs, 1H), 5.52–5.46 (d, d, J=12.9, 4.5 Hz, 1H), 4.92–4.85 (m, 2H), 4.81–4.75 (d, d, J=16.2, 1.8 Hz, 1H), 4.65–4.61 (d, d, J=8.4, 3.6 Hz, 1H), 4.40–4.20 (m, 3H), 3.86 (s, 3H), 3.83–3.81 (m, 1H), 3.72 (s, 2H), 3.38 (s, 2H), 2.85–2.78 (m, 1H), 2.75–2.56 (m, 2H), 2.54–2.44 (d, d, J=16.2, 8.1, 3.9 Hz, 1H); MS 588 (M+H).

Naphthalene-2-carboxylic acid {1-[(2-hydroxy-5-oxo-tetrahydro-furan-3-ylcarbamoyl)-methyl]-6-[(2-methoxy-benzylamino)-methyl]-2-oxo-2,3,4,7-tetrahydro-1H-azepin-3-yl}-amide: $^1$H NMR ($CD_3OD$) δ 8.48 (s, 1H), 8.03–7.93 (m, 4H), 7.66–7.57 (m, 2H), 7.52–7.46 (m, 2H), 7.16–7.13 (d, J=9.3 Hz, 1H), 7.10–7.05 (d, d, d, J=8.4, 7.2, 0.6 Hz, 1H), 6.11 (bs, 1H), 5.54–5.48 (d, d, J=12.6, 3.9 Hz, 1H), 4.88–4.85 (m, 1H), 4.77–4.70 (d, d, J=16.2, 3.6 Hz, 1H), 4.63–4.59 (d, d, J=7.5, 3.6 Hz, 1H), 4.34–4.29 (m, 3H), 3.99 (s, 3H), 3.89–3.84 (d, J=15.9 Hz, 1H), 3.75–3.67 (d, d, J=17.4, 6.3 Hz, 1H), 3.72 (s, 2H), 2.87–2.79 (d, d, J=17.7, 3.6 Hz, 1H), 2.73–2.59 (m, 2H), 2.53–2.44 (d, d, d, J=16.5, 8.1, 3.3 Hz, 1H); MS 588 (M+H).

Naphthalene-2-carboxylic acid {1-[(2-hydroxy-5-oxo-tetrahydro-furan-3-ylcarbamoyl)-methyl]-6-[(3-methoxy-benzylamino)-methyl]-2-oxo-2,3,4,7-tetrahydro-1H-azepin-3-yl}-amide: $^1$H NMR ($CD_3OD$) δ 8.47 (s, 1H), 8.02–7.92 (m, 4H), 7.65–7.56 (m, 2H), 7.44–7.38 (d, d, J=8.4, 8.1 Hz, 1H), 7.17–7.15 (m, 2H), 7.04–7.01 (d, d, J=8.4, 1.8 Hz, 1H), 6.10 (bs, 1H), 5.52–5.46 (d, d, J=12.9, 4.5 Hz, 1H), 4.92–4.85 (m, 2H), 4.81–4.75 (d, d, J=16.2, 1.8 Hz, 1H), 4.65–4.61 (d, d, J=8.4, 3.6 Hz, 1H), 4.40–4.20 (m, 3H), 3.86 (s, 3H), 3.83–3.81 (m, 1H), 3.72 (s, 2H), 3.38 (s, 2H), 2.85–2.78 (m, 1H), 2.75–2.56 (m, 2H), 2.54–2.44 (d, d, J=16.2, 8.1, 3.9 Hz, 1H); MS 588 (M+H).

Naphthalene-2-carboxylic acid {1-[(2-hydroxy-5-oxo-tetrahydro-furan-3-ylcarbamoyl)-methyl]-6-[(2-methoxy-benzylamino)-methyl]-2-oxo-2,3,4,7-tetrahydro-1H-azepin-3-yl}-amide: $^1$H NMR ($CD_3OD$) δ 8.48 (s, 1H), 8.03–7.93 (m, 4H), 7.66–7.57 (m, 2H), 7.52–7.46 (m, 2H), 7.16–7.13 (d, J=9.3 Hz, 1H), 7.10–7.05 (d, d, d, J=8.4, 7.2, 0.6 Hz, 1H), 6.11 (bs, 1H), 5.54–5.48 (d, d, J=12.6, 3.9 Hz, 1H), 4.88–4.85 (m, 1H), 4.77–4.70 (d, d, J=16.2, 3.6 Hz, 1H), 4.63–4.59 (d, d, J=7.5, 3.6 Hz, 1H), 4.34–4.29 (m, 3H), 3.99 (s, 3H), 3.89–3.84 (d, J=15.9 Hz, 1H), 3.75–3.67 (d, d, J=17.4, 6.3 Hz, 1H), 3.72 (s, 2H), 2.87–2.79 (d, d, J=17.7, 3.6 Hz, 1H), 2.73–2.59 (m, 2H), 2.53–2.44 (d, d, d, J=16.5, 8.1, 3.3 Hz, 1H); MS 588 (M+H).

Naphthalene-2-carboxylic acid {6-[(2-fluoro-benzoylamino)-methyl]-1-[3-(2-hydroxy-5-oxo-tetrahydro-furan-3-yl)-2-oxo-propyl]-2-oxo-2,3,4,7-tetrahydro-1H-azepin-3-yl}-amide: $^1$H NMR ($CD_3OD$) δ 8.46 (s, 1H), 8.02–7.91 (m, 4H), 7.80–7.75 (m, 1H), 7.64–7.52 (m, 3H), 7.34–7.21 (m, 2H), 5.83 (bs, 1H), 5.58–5.52 (d, d, J=12.9, 4.5 Hz, 1H), 4.88–4.83 (m, 1H), 4.64–4.61 (d, d, J=7.2, 3.6 Hz, 1H), 4.37–4.24 (m, 3H), 4.05 (s, 2H), 3.63–3.56 (d, d, J=18.0, 3.3 Hz, 1H), 2.79–2.47 (m, 4H); MS 589 (M+H).

Naphthalene-2-carboxylic acid {6-[(3-fluoro-benzoylamino)-methyl]-1-[3-(2-hydroxy-5-oxo-tetrahydro-furan-3-yl)-2-oxo-propyl]-2-oxo-2,3,4,7-tetrahydro-1H-azepin-3-yl}-amide: $^1$H NMR ($CD_3OD$) δ 8.46 (s, 1H), 8.00–7.91 (m, 4H), 7.76–7.73 (m, 1H), 7.65–7.49 (m, 4H), 7.34–7.28 (m, 1H), 5.81 (bs, 1H), 5.56–5.51 (d, d, J=12.3, 2.9 Hz, 1H), 4.89–4.82 (m, 1H), 4.64–4.61 (m, 1H), 4.39–4.14 (m, 3H), 4.03 (s, 2H), 3.62–3.55 (d, d, J=18.0, 3.3 Hz, 1H), 2.78–2.65 (m, 2H), 2.61–2.47 (m, 2H); MS 589 (M+H).

Naphthalene-2-carboxylic acid {6-[(4-fluoro-benzoylamino)-methyl]-1-[3-(2-hydroxy-5-oxo-tetrahydro-furan-3-yl)-2-oxo-propyl]-2-oxo-2,3,4,7-tetrahydro-1H-azepin-3-yl}-amide: $^1$H NMR ($CD_3OD$) δ 8.45 (s, 1H), 8.00–7.91 (m, 4H), 7.63–7.54 (m, 2h), 7.26–7.20 (m, 2H), 5.82 (bs, 1H), 5.56–5.50 (d, d, J=12.9, 4.5 Hz, 1H), 4.88–4.81 (m, 1H), 4.63–4.61 (m, 1H), 4.39–4.12 (m, 3H), 4.02 (s, 2H), 3.63–3.56 (d, d, J=17.7, 3.0 Hz, 1H), 2.77–2.66 (m, 2H), 2.60–2.47 (m, 2H); MS 589 (M+H).

Naphthalene-2-carboxylic acid {1-[(2-hydroxy-5-oxo-tetrahydro-furan-3-ylcarbamoyl)-methyl]-6-[(2-methoxy-benzoylamino)-methyl]-2-oxo-2,3,4,7-tetrahydro-1H-azepin-3-yl}-amide: $^1$H NMR ($CD_3OD$) δ 8.47 (s, 1H), 8.02–7.88 (m, 5H), 7.64–7.50 (m, 3H), 7.19–7.16 (d, J=8.1 Hz), 7.11–7.06 (d, d, J=8.4, 7.5 Hz, 1H), 5.82 (bs, 1H), 5.60–5.54 (d, d, J=12.9, 4.2 Hz, 1H), 4.86–4.83 (m, 1H), 4.64–4.60 (d, d, J=7.8, 3.9 Hz, 1H), 4.35–4.13 (m, 3H), 4.08 (s, 2H), 4.01 (s, 3H), 3.63–3.56 (d, d, J=18.0, 3.0 Hz, 1H), 2.80–2.62 (m, 2H), 2.57 (m, 2H); MS 601 (M+H).

Naphthalene-2-carboxylic acid {1-[(2-hydroxy-5-oxo-tetrahydro-furan-3-ylcarbamoyl)-methyl]-6-[(3-methoxy-benzoylamino)-methyl]-2-oxo-2,3,4,7-tetrahydro-1H-azepin-3-yl}-amide: $^1$H NMR ($CD_3OD$) δ 8.46 (s, 1H), 8.00–7.91 (m, 4H), 7.63–7.54 (m, 2H), 7.49–7.38 (m, 3H), 7.13–7.10 (m, 1H), 5.80 (s, 1H), 5.56–5.51 (d, d, J=12.9, 4.5 Hz, 1H), 4.88–4.80 (m, 1H), 4.63–4.60 (d, d, J=4.8, 4.2 Hz, 1H), 4.40–4.22 (m, 3H), 4.08 (s, 2H), 3.87 (s, 3H), 3.62–3.55 (d, d, J=17.7, 2.7 Hz, 1H), 2.78–2.65 (m, 2H), 2.60–2.47 (m, 2H); MS 601 (M+H).

Naphthalene-2-carboxylic acid {1-[(2-hydroxy-5-oxo-tetrahydro-furan-3-ylcarbamoyl)-methyl]-6-[(4-methoxy-benzoylamino)-methyl]-2-oxo-2,3,4,7-tetrahydro-1H-azepin-3-yl}-amide: $^1$H NMR ($CD_3OD$) δ 8.45 (s, 1H), 7.99–7.85 (m, 6H), 7.62–7.54 (m, 2H), 7.04–6.99 (m, 2H), 5.80 (bs, 1H), 5.55–5.50 (d, J=12.3, 3.9 Hz, 1H), 4.88–4.80 (m, 1H), 4.63–4.60 (d, d, J=3.6, 3.6 Hz, 1H), 4.42–4.13 (m, 3H), 4.00 (s, 2H), 3.86 (s, 3H), 3.61–3.55 (d, J=17.1, 1.8 Hz, 1H), 2.77–2.65 (m, 2H), 2.55–2.47 (m, 2H); MS 601 (M+H).

Naphthalene-2-carboxylic acid {6-benzylsulfanylmethyl-1-[(2-hydroxy-5-oxo-tetrahydro-furan-3-ylcarbamoyl)-methyl]-2-oxo-2,3,4,7-tetrahydro-1H-azepin-3-yl}-amide: $^1$H NMR (CD$_3$OD) δ 8.46 (s, 1H), 8.01–7.91 (m, 4H), 7.63–7.55 (m, 2H), 7.35–7.22 (m, 5H), 5.56–5.48 (m, 2H), 4.75–4.69 (d, J=17.1 Hz, 1H), 4.66–4.63 (d, d, J=3.6, 3.6 Hz, 1H), 4.41–4.34 (m, 2H), 4.16–4.10 (d, d, J=16.5, 2.4 Hz, 1H), 3.68–3.67 (d, J=2.7 Hz, 1H), 3.58–3.51 (d, d, J=17.4, 4.8 Hz, 1H), 3.38 (s, 2H), 3.18 (d, J=14.1 Hz, 1H), 3.04–2.99 (d, J=13.5 Hz, 1H), 2.76–2.66 (m, 2H), 2.58–2.49 (m, 2H); MS 574 (M+H).

Naphthalene-2-carboxylic acid {1-[(2-hydroxy-5-oxo-tetrahydro-furan-3-ylcarbamoyl)-methyl]-2-oxo-6-phenylsulfanylmethyl-2,3,4,7-tetrahydro-1H-azepin-3-yl}-amide: $^1$H NMR (CD$_3$OD) δ 8.45 (s, 1H), 8.01–7.90 (m, 4H), 7.63–7.55 (m, 2H), 7.44–7.23 (m, 5H), 5.52–5.47 (m, 2H), 4.68–4.79 (m, 1H), 4.66–4.63 (d, d, J=4.2, 4.2 Hz, 1H), 4.47–4.33 (m, 2H), 4.16–4.10 (d, d, J=16.2, 2.4 Hz, 1H), 3.72–3.65 (m, 2H), 3.52–3.48 (d, J=13.5 Hz, 1H), 3.39–3.38 (m, 1H), 2.77–2.64 (m, 2H), 2.58–2.49 (m, 2H), 2.43–2.33 (d, d, J=16.8, 13.8 Hz, 1H); MS 560 (M+H).

The fourth aspect of Category III comprises scaffolds having the formula:

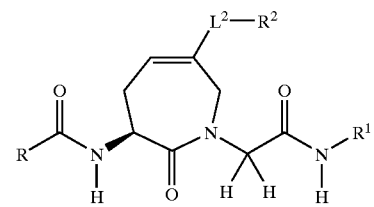

wherein R, R$^1$, L$^2$ and R$^2$ are described herein below in Table VI.

TABLE VI

| No. | R | R$^1$ | —L$^2$—R$^2$ |
|---|---|---|---|
| 313 | phenyl | 2-hydroxy-5-oxo-tetrahydrofuran-3-yl | —CH$_2$NHSO$_2$C$_6$H$_5$ |
| 314 | 2-naphthyl | 2-hydroxy-5-oxo-tetrahydrofuran-3-yl | CH$_2$NHSO$_2$C$_6$H$_5$ |
| 315 | 1-isoquinolinyl | 2-hydroxy-5-oxo-tetrahydrofuran-3-yl | CH$_2$NHSO$_2$C$_6$H$_5$ |
| 319 | phenyl | 2-hydroxy-5-oxo-tetrahydrofuran-3-yl | —CH$_2$NHSO$_2$(4-n-pentylC$_6$H$_4$) |
| 320 | 2-naphthyl | 2-hydroxy-5-oxo-tetrahydrofuran-3-yl | —CH$_2$NHSO$_2$(4-n-pentylC$_6$H$_4$) |
| 321 | 1-isoquinolinyl | 2-hydroxy-5-oxo-tetrahydrofuran-3-yl | —CH$_2$NHSO$_2$(4-n-pentylC$_6$H$_4$) |
| 322 | phenyl | 2-hydroxy-5-oxo-tetrahydrofuran-3-yl | —CH$_2$NHSO$_2$(2-FC$_6$H$_4$) |
| 323 | 2-naphthyl | 2-hydroxy-5-oxo-tetrahydrofuran-3-yl | —CH$_2$NHSO$_2$(2-FC$_6$H$_4$) |
| 324 | 1-isoquinolinyl | 2-hydroxy-5-oxo-tetrahydrofuran-3-yl | —CH$_2$NHSO$_2$(2-FC$_6$H$_4$) |
| 325 | phenyl | 2-hydroxy-5-oxo-tetrahydrofuran-3-yl | —CH$_2$NHSO$_2$(3-FC$_6$H$_4$) |
| 326 | 2-naphthyl | 2-hydroxy-5-oxo-tetrahydrofuran-3-yl | —CH$_2$NHSO$_2$(3-FC$_6$H$_4$) |
| 327 | 1-isoquinolinyl | 2-hydroxy-5-oxo-tetrahydrofuran-3-yl | —CH$_2$NHSO$_2$(3-FC$_6$H$_4$) |
| 328 | phenyl | 2-hydroxy-5-oxo-tetrahydrofuran-3-yl | —CH$_2$NHSO$_2$(4-FC$_6$H$_4$) |
| 329 | 2-naphthyl | 2-hydroxy-5-oxo-tetrahydrofuran-3-yl | —CH$_2$NHSO$_2$(4-FC$_6$H$_4$) |
| 330 | 1-isoquinolinyl | 2-hydroxy-5-oxo-tetrahydrofuran-3-yl | —CH$_2$NHSO$_2$(4-FC$_6$H$_4$) |
| 331 | phenyl | 2-hydroxy-5-oxo-tetrahydrofuran-3-yl | —CH$_2$NHSO$_2$(2-CH$_3$C$_6$H$_4$) |
| 332 | 2-naphthyl | 2-hydroxy-5-oxo-tetrahydrofuran-3-yl | —CH$_2$NHSO$_2$(2-CH$_3$C$_6$H$_4$) |
| 333 | 1-isoquinolinyl | 2-hydroxy-5-oxo-tetrahydrofuran-3-yl | —CH$_2$NHSO$_2$(2-CH$_3$C$_6$H$_4$) |
| 334 | phenyl | 2-hydroxy-5-oxo-tetrahydrofuran-3-yl | —CH$_2$NHSO$_2$(3-CH$_3$C$_6$H$_4$) |
| 335 | 2-naphthyl | 2-hydroxy-5-oxo-tetrahydrofuran-3-yl | —CH$_2$NHSO$_2$(3-CH$_3$C$_6$H$_4$) |
| 336 | 1-isoquinolinyl | 2-hydroxy-5-oxo-tetrahydrofuran-3-yl | —CH$_2$NHSO$_2$(3-CH$_3$C$_6$H$_4$) |
| 337 | phenyl | 2-hydroxy-5-oxo-tetrahydrofuran-3-yl | —CH$_2$NHSO$_2$(4-CH$_3$C$_6$H$_4$) |
| 338 | 2-naphthyl | 2-hydroxy-5-oxo-tetrahydrofuran-3-yl | —CH$_2$NHSO$_2$(4-CH$_3$C$_6$H$_4$) |
| 339 | 1-isoquinolinyl | 2-hydroxy-5-oxo-tetrahydrofuran-3-yl | —CH$_2$NHSO$_2$(4-CH$_3$C$_6$H$_4$) |
| 340 | phenyl | 2-hydroxy-5-oxo-tetrahydrofuran-3-yl | —CH$_2$NHSO$_2$(2-OCH$_3$C$_6$H$_4$) |
| 341 | 2-naphthyl | 2-hydroxy-5-oxo-tetrahydrofuran-3-yl | —CH$_2$NHCO(2-OCH$_3$C$_6$H$_4$) |
| 342 | 1-isoquinolinyl | 2-hydroxy-5-oxo-tetrahydrofuran-3-yl | —CH$_2$NHCO(2-OCH$_3$C$_6$H$_4$) |
| 343 | phenyl | 2-hydroxy-5-oxo-tetrahydrofuran-3-yl | —CH$_2$NHCO(3-OCH$_3$C$_6$H$_4$) |
| 344 | 2-naphthyl | 2-hydroxy-5-oxo-tetrahydrofuran-3-yl | —CH$_2$NHCO(3-OCH$_3$C$_6$H$_4$) |
| 345 | 1-isoquinolinyl | 2-hydroxy-5-oxo-tetrahydrofuran-3-yl | —CH$_2$NHCO(3-OCH$_3$C$_6$H$_4$) |
| 346 | phenyl | 2-hydroxy-5-oxo-tetrahydrofuran-3-yl | —CH$_2$NHCO(4-OCH$_3$C$_6$H$_4$) |
| 347 | 2-naphthyl | 2-hydroxy-5-oxo-tetrahydrofuran-3-yl | —CH$_2$NHCO(4-OCH$_3$C$_6$H$_4$) |
| 348 | 1-isoquinolinyl | 2-hydroxy-5-oxo-tetrahydrofuran-3-yl | —CH$_2$NHCO(4-OCH$_3$C$_6$H$_4$) |
| 349 | 1-isoquinolinyl | 2-ethoxy-5-oxo-tetrahydrofuran-3-yl | —CH$_2$NHCOC$_6$H$_5$ |
| 350 | phenyl | 2-ethoxy-5-oxo-tetrahydrofuran-3-yl | —CH$_2$NHCOC$_6$H$_5$ |
| 351 | 2-naphthyl | 2-ethoxy-5-oxo-tetrahydrofuran-3-yl | —CH$_2$NHCOC$_6$H$_5$ |
| 352 | 1-isoquinolinyl | 2-ethoxy-5-oxo-tetrahydrofuran-3-yl | —CH$_2$NHCO[4-CH(CH$_3$)$_2$C$_6$H$_4$] |
| 353 | phenyl | 2-ethoxy-5-oxo-tetrahydrofuran-3-yl | —CH$_2$NHCO[4-CH(CH$_3$)$_2$C$_6$H$_4$] |
| 354 | 2-naphthyl | 2-ethoxy-5-oxo-tetrahydrofuran-3-yl | —CH$_2$NHCO[4-CH(CH$_3$)$_2$C$_6$H$_4$] |
| 355 | 1-isoquinolinyl | 2-ethoxy-5-oxo-tetrahydrofuran-3-yl | —CH$_2$NHCO(4-n-pentylC$_6$H$_4$) |
| 356 | phenyl | 2-ethoxy-5-oxo-tetrahydrofuran-3-yl | —CH$_2$NHCO(4-n-pentylC$_6$H$_4$) |
| 357 | 2-naphthyl | 2-ethoxy-5-oxo-tetrahydrofuran-3-yl | —CH$_2$NHCO(4-n-pentylC$_6$H$_4$) |
| 358 | 1-isoquinolinyl | 2-ethoxy-5-oxo-tetrahydrofuran-3-yl | —CH$_2$NHCO(2-FC$_6$H$_4$) |
| 359 | phenyl | 2-ethoxy-5-oxo-tetrahydrofuran-3-yl | —CH$_2$NHCO(2-FC$_6$H$_4$) |
| 360 | 2-naphthyl | 2-ethoxy-5-oxo-tetrahydrofuran-3-yl | —CH$_2$NHCO(2-FC$_6$H$_4$) |
| 361 | 1-isoquinolinyl | 2-ethoxy-5-oxo-tetrahydrofuran-3-yl | —CH$_2$NHCO(3-FC$_6$H$_4$) |
| 362 | phenyl | 2-ethoxy-5-oxo-tetrahydrofuran-3-yl | —CH$_2$NHCO(3-FC$_6$H$_4$) |
| 363 | 2-naphthyl | 2-ethoxy-5-oxo-tetrahydrofuran-3-yl | —CH$_2$NHCO(3-FC$_6$H$_4$) |
| 364 | 1-isoquinolinyl | 2-ethoxy-5-oxo-tetrahydrofuran-3-yl | —CH$_2$NHCO(4-FC$_6$H$_4$) |
| 365 | phenyl | 2-ethoxy-5-oxo-tetrahydrofuran-3-yl | —CH$_2$NHCO(4-FC$_6$H$_4$) |
| 366 | 2-naphthyl | 2-ethoxy-5-oxo-tetrahydrofuran-3-yl | —CH$_2$NHCO(4-FC$_6$H$_4$) |
| 367 | 1-isoquinolinyl | 2-ethoxy-5-oxo-tetrahydrofuran-3-yl | —CH$_2$NHCO(2-CH$_3$C$_6$H$_4$) |

TABLE VI-continued

| No. | R | R¹ | —L²—R² |
|-----|---|----|--------|
| 368 | phenyl | 2-ethoxy-5-oxo-tetrahydrofuran-3-yl | —CH$_2$NHCO(2-CH$_3$C$_6$H$_4$) |
| 369 | 2-naphthyl | 2-ethoxy-5-oxo-tetrahydrofuran-3-yl | —CH$_2$NHCO(2-CH$_3$C$_6$H$_4$) |
| 370 | 1-isoquinolinyl | 2-ethoxy-5-oxo-tetrahydrofuran-3-yl | —CH$_2$NHCO(3-CH$_3$C$_6$H$_4$) |
| 371 | phenyl | 2-ethoxy-5-oxo-tetrahydrofuran-3-yl | —CH$_2$NHCO(3-CH$_3$C$_6$H$_4$) |
| 372 | 2-naphthyl | 2-ethoxy-5-oxo-tetrahydrofuran-3-yl | —CH$_2$NHCO(3-CH$_3$C$_6$H$_4$) |
| 373 | 1-isoquinolinyl | 2-ethoxy-5-oxo-tetrahydrofuran-3-yl | —CH$_2$NHCO(4-CH$_3$C$_6$H$_4$) |
| 374 | phenyl | 2-ethoxy-5-oxo-tetrahydrofuran-3-yl | —CH$_2$NHCO(4-CH$_3$C$_6$H$_4$) |
| 375 | 2-naphthyl | 2-ethoxy-5-oxo-tetrahydrofuran-3-yl | —CH$_2$NHCO(4-CH$_3$C$_6$H$_4$) |
| 376 | 1-isoquinolinyl | 2-ethoxy-5-oxo-tetrahydrofuran-3-yl | —CH$_2$NHCO(2-OCH$_3$C$_6$H$_4$) |
| 377 | phenyl | 2-ethoxy-5-oxo-tetrahydrofuran-3-yl | —CH$_2$NHCO(2-OCH$_3$C$_6$H$_4$) |
| 378 | 2-naphthyl | 2-ethoxy-5-oxo-tetrahydrofuran-3-yl | —CH$_2$NHCO(2-OCH$_3$C$_6$H$_4$) |
| 379 | 1-isoquinolinyl | 2-ethoxy-5-oxo-tetrahydrofuran-3-yl | —CH$_2$NHCO(3-OCH$_3$C$_6$H$_4$) |
| 380 | phenyl | 2-ethoxy-5-oxo-tetrahydrofuran-3-yl | —CH$_2$NHCO(3-OCH$_3$C$_6$H$_4$) |
| 381 | 2-naphthyl | 2-ethoxy-5-oxo-tetrahydrofuran-3-yl | —CH$_2$NHCO(3-OCH$_3$C$_6$H$_4$) |
| 382 | 1-isoquinolinyl | 2-ethoxy-5-oxo-tetrahydrofuran-3-yl | —CH$_2$NHCO(4-OCH$_3$C$_6$H$_4$) |
| 383 | phenyl | 2-ethoxy-5-oxo-tetrahydrofuran-3-yl | —CH$_2$NHCO(4-OCH$_3$C$_6$H$_4$) |
| 384 | 2-naphthyl | 2-ethoxy-5-oxo-tetrahydrofuran-3-yl | —CH$_2$NHCO(4-OCH$_3$C$_6$H$_4$) |

The compounds of the fourth aspect of Category III can be suitably prepared by the procedure outlined herein below, utilizing intermediates such as 29 as a starting point which can be synthesized by the procedure described in Scheme X.

Scheme XII

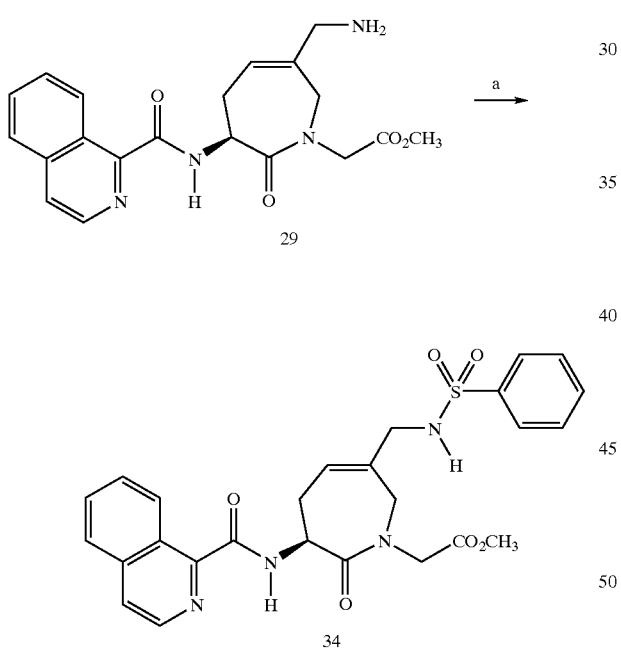

Reagents and conditions: a) PhSO$_2$Cl, Et$_3$N, THF; rt.

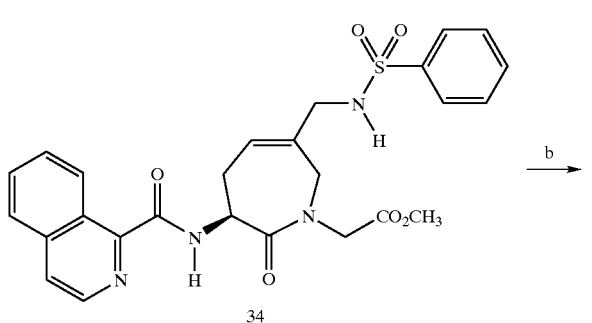

34

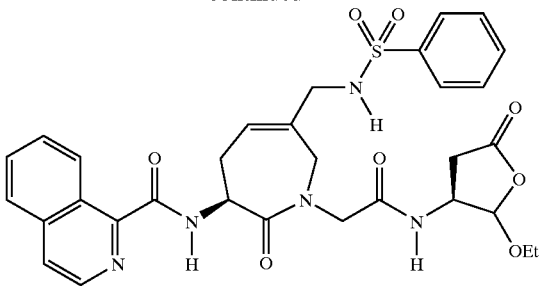

35

(b) Several steps as in Schemes X and XI

Compound 34 can be taken forward in the synthesis of compounds of the fourth aspect of Category III analogs in the same manner as depicted herein above in Scheme X and Scheme XI.

EXAMPLE 9

Isoquinoline-1-carboxylic acid {6-(benzenesulfonylamino-methyl)-1-[(2-ethoxy-5-oxo-tetrahydro-furan-3-ylcarbamoyl)-methyl]-2-oxo-2,3,4,7-tetrahydro-1H-azepin-3-yl}-amide(35)

Preparation of {6-(Benzenesulfonylamino-methyl)-3-[(isoquinoline-1-carbonyl)-amino]-2-oxo-2,3,4,7-tetrahydro-azepin-1-yl}-acetic acid methyl ester (34) To {6-aminomethyl-3-[(isoquinoline-1-carbonyl)-amino]-2-oxo-2,3,4,7-tetrahydro-azepin-1-yl}-acetic acid methyl ester (29) (0.14 g, 0.37 mmol) in 1 mL THF was added benzene sulfonyl chloride (0.132 mL, 0.75 mmol) and triethyl amine (0.71 mL, 4.99 mmol) were added at rt. The reaction was completed instantly and quenched with 5 mL methanol and the solvent was removed under vacuum. After HPLC purification obtained 84 mg (46%) of 34. MS 523 (M+H).

Preparation of Isoquinoline-1-carboxylic acid {6-(benzenesulfonylamino-methyl)-1-[(2-ethoxy-5-oxo-tetrahydrofuran-3-ylcarbamoyl)-methyl]-2-oxo-2,3,4,7-tetrahydro-1H-azepin-3-yl}-amide (35): A solution containing {6-

(Benzenesulfonylamino-methyl)-3-[(isoquinoline-1-carbonyl)-amino]-2-oxo-2,3,4,7-tetrahydro-azepin-1-yl}-acetic acid methyl ester (34) (84 mg, 0.17 mmol) in 4 mL of 3:1 THF/H$_2$O was treated with excess LiOH and stirred for 2.5 h at rt. The solution was acidified and extracted with EtOAc. The EtOAc layer was dried (Na$_2$SO$_4$) and concentrated to give the crude carboxylic acid. A catalytic amount of Pd(Ph$_3$P)$_4$ is added to a solution of (2-ethoxy-5-oxo-furan-3-yl)-carbamic acid allyl ester (0.24 g, 1.0 mmol) and N,N-dimethylbarbituric acid (0.38 g, 2.4 mmol) in CH$_2$Cl$_2$ (5 mL). The solution is stirred for 15 minutes at room temperature after which {6-(Benzenesulfonylamino-methyl)-3-[(isoquinoline-1-carbonyl)-amino]-2-oxo-2,3,4,7-tetrahydro-azepin-1-yl}-acetic acid (0.069 g) is added as a solution in CH$_2$Cl$_2$/DMF (2 mL, 1:1), followed by HOBt (0.126 g, 0.93 mmol) and EDCl (0.18 g, 0.93 mmol). The solution is stirred for 5 hours, diluted with EtOAc, washed with saturated NaHCO$_3$ and brine, dried (Na$_2$SO$_4$), and concentrated in vacuo. The resulting residue us purified over silica (EtOAc/hexane) to afford the desired compound.

The compounds of this category wherein R$^1$ comprises the cysteine trap 2-hydroxy-5-oxo-tetrahydrofuran-3-yl can be prepared by the procedure outlined in Scheme XII as indicated in the following example starting with compound 35.

Scheme XIII

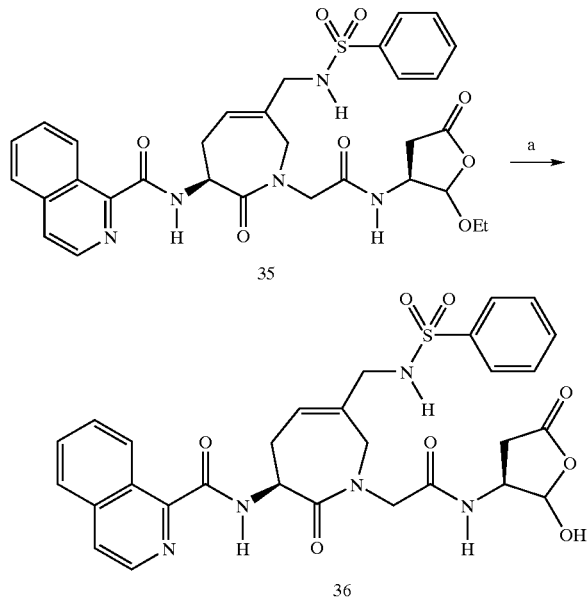

Reagents and conditions: (a) TFA. CH$_3$CN, H$_2$O; rt

EXAMPLE 10

Isoquinoline-1-carboxylic acid {6-(benzenesulfonylamino-methyl)-1-[(2-hydroxy-5-oxo-tetrahydro-furan-3-ylcarbamoyl)-methyl]-2-oxo-2,3,4,7-tetrahydro-1H-azepin-3-yl}-amide(36)

Preparation of Isoquinoline-1-carboxylic acid {6-(benzenesulfonylamino-methyl)-1-[(2-hydroxy-5-oxo-tetrahydro-furan-3-ylcarbamoyl)-methyl]-2-oxo-2,3,4,7-tetrahydro-1H-azepin-3-yl}-amide (36): A solution of isoquinoline-1-carboxylic acid {6-(benzenesulfonylamino-methyl)-1-[(2-ethoxy-5-oxo-tetrahydro-furan-3-ylcarbamoyl)-methyl]-2-oxo-2,3,4,7-tetrahydro-1H-azepin-3-yl}-amide, 35, as prepared in the above example, in CH$_3$CN/H$_2$O is treated with excess trifluoroacetic acid. The solution is stirred several hours then purified by preparative reverse phase HPLC to afford 150 mg (65% yield) of the desired product. $^1$H NMR (CD$_3$OD) δ 9.14–9.11 (d, J=8.7 Hz, 1H), 8.55–8.53 (d, J=5.4 Hz, 1H), 8.07–8.03 (m, 2H), 7.93–7.85 (m, 3H), 7.81–7.76 (m, 1H), 7.68–7.60 (m, 3H), 5.68 (bs, 1H), 5.49–5.43 (d, d, J=12.3, 3.9 Hz, 1H), 4.68–4.62 (m, 2H), 4.41–4.32 (m, 1H), 4.30–4.01 (m, 2H), 3.55–3.48 (m, 3H), 2.81–2.67 (m, 2H), 2.57–2.49 (d, d, d, J=16.2, 8.4, 1.2 Hz, 1H), 2.46–2.36 (d, d, J=15.0, 15.0 Hz, 1H); MS 608 (M+H).

Other non-limiting examples of compounds which comprise this aspect of Category III include:

Isoquinoline-1-carboxylic acid [(2-hydroxy-5-oxo-tetrahydro-furan-3-ylcarbamoyl)-methyl]-6-(methanesulfonylamino-methyl)-2-oxo-2,3,4,7-tetrahydro-1H-azepin-3-yl]-amide: $^1$H NMR (CD$_3$OD) δ 9.17–9.14 (d, J=8.7 Hz, 1H), 8.57–8.55 (d, J=5.7 Hz, 1H), 8.07–8.04 (m, 2H), 7.90–7.85 (d, d, d, J=8.1, 6.9, 1.2 Hz, 1H), 7.82–7.76 (d, d, d, J=8.4, 6.9, 1.5 Hz, 1H), 5.86 (bs, 1H), 5.62–5.56 (d, d, J=12.6, 4.2 Hz, 1 H), 4.85–4.79 (bd, J=17.7 Hz, 1H), 4.67–4.63 (m, 1H), 4.37–4.18 (m, 3H), 3.71–3.51 (m, 3H), 2.91–2.85 (d, d, J=18.0, 3.0 Hz, 1H), 2.76–2.66 (m, 1H), 2.56–2.48 (m, 2H); MS 546 (M+H).

Naphthalene-2-carboxylic acid {6-(benzenesulfonylamino-methyl)-1-[(2-hydroxy-5-oxo-tetrahydro-furan-3-ylcarbamoyl)-methyl]-2-oxo-2,3,4,7-tetrahydro-1H-azepin-3-yl}-amide: $^1$H NMR (CD$_3$OD) δ 8.45 (s, 1H), 8.01–7.89 (m, 6H), 7.67–7.55 (m, 5H), 5.67 (bs, 1H), 5.43–5.38 (d, d, J=12.3, 3.9 Hz, 1H), 4.69–4.59 (m, 2H), 4.40–4.32 (m, 1H), 4.19 (s, 2H), 3.51 (s, 2H), 3.46–3.45 (d, J=3.6 Hz, 1H), 2.77–2.64 (m, 2H), 2.60–2.41 (m, 2H); MS 607 (M+H).

Naphthalene-2-carboxylic acid {1-[(2-hydroxy-5-oxo-tetrahydro-furan-3-ylcarbamoyl)-methyl]-6-[(4-methoxy-benzenesulfonylamino)-methyl}-2-oxo-2,3,4,7-tetrahydro-1H-azepin-3-yl}-amide: $^1$H NMR (CD$_3$OD) δ 8.46 (s, 1H), 8.02–7.92 (m, 4H), 7.85–7.82 (d, J=8.7 Hz, 2H), 7.64–7.56 (m, 2H), 7.14–7.11 (d, J=9.3 Hz, 1H), 5.67 (bs, 1H), 5.41–5.35 (d, d, J=12.6, 4.2 Hz, 1H), 4.69–4.66 (d, d, J=4.8, 4.2 Hz, 1H), 4.62–4.58 (d, J=16.5 Hz, 1H), 4.40–4.31 (m, 1H), 4.25–4.13 (m, 2H), 3.96 (s, 3H), 3.53–3.33 (m, 3H), 2.77–2.64 (m, 2H), 2.57–2.49 (m, 2H); MS 637.4 (M+H).

Naphthalene-2-carboxylic acid {1-[(2-hydroxy-5-oxo-tetrahydro-furan-3-ylcarbamoyl)-methyl]-2-oxo-6-[(toluene-3-sulfonylamino)-methyl]-2,3,4,7-tetrahydro-1H-azepin-3-yl}-amide: $^1$H NMR (CD$_3$OD) δ 8.46 (s, 1H), 8.02–7.91 (m, 4H), 7.72–7.68 (m, 2H), 7.62–7.56 (m, 2H), 7.51–7.49 (m, 2H), 5.67 (bs, 1H), 5.43–5.37 (d, d, J=12.9, 4.5 Hz, 1H), 4.69–4.66 (d, d, J=4.5, 3.9 Hz, 1H), 4.65–4.59 (d, J=16.8 Hz, 1H), 4.40–4.31 (m, 1H), 4.26–4.19 (d, J=16.5 Hz, 1H), 4.18–4.12 (d, J=16.5 Hz, 1H), 3.53–3.46 (m, 3H), 2.77–2.67 (m, 2H), 2.57–2.49 (m, 2H), 2.47 (s, 3H); MS 621.2 (M+H).

Naphthalene-2-carboxylic acid {1-[(2-hydroxy-5-oxo-tetrahydro-furan-3-ylcarbamoyl)-methyl]-2-oxo-6-[(toluene-2-sulfonylamino)-methyl]-2,3,4,7-tetrahydro-1H-azepin-3-yl}-amide: $^1$H NMR (CD$_3$OD) δ 8.46 (s, 1H), 8.02–7.94 (m, 5H), 7.64–7.52 (m, 3H), 7.44–7.38 (m, 2H), 5.66 (bs, 1H), 5.38–5.33 (d, d, J=12.6, 4.2 Hz, 1H), 4.68–4.65 (d, d, J=5.4, 3.9 Hz, 1H), 4.61–4.55 (d, J=17.1 Hz, 1H), 4.37–4.32 (m, 1H), 4.25–4.20 (d, J=16.5 Hz, 1H), 4.18–4.12 (d, J=16.5 Hz, 1H), 3.61–3.47 (m, 3H), 2.71 (s, 3H), 2.62–2.44 (m, 4H); MS 620.95 (M+H).

Naphthalene-2-carboxylic acid {1-[(2-hydroxy-5-oxo-tetrahydro-furan-3-ylcarbamoyl)-methyl]-2-oxo-6-[(toluene-4-sulfonylamino)-methyl]-2,3,4,7-tetrahydro-1H-azepin-3-yl}-amide: $^1$H NMR (CD$_3$OD) δ 8.44 (s, 1H), 7.98–7.90 (m, 4H), 7.78–7.76 (d, J=8.4 Hz, 2H), 7.62–7.53 (m, 2H), 7.42–7.39 (d, J=8.1 Hz, 1H), 5.63 (bs, 1h), 5.38–5.33 (d, d, J=12.9, 4.5 Hz, 1H), 4.69–4.66 (d, d, J=4.8, 4.2 Hz, 1H), 4.62–4.56 (d, J=18.3 Hz, 1H), 4.26–4.20 (d, J=16.2 Hz, 1H), 4.18–4.11 (d, J=16.5 Hz, 1H), 3.52–3.44 (m, 3H), 2.77–2.67 (m, 2H), 2.60–2.49 (m, 2H), 2.42 (s, 3H); MS 620.67 (M+H).

Naphthalene-2-carboxylic acid {1-[(2-hydroxy-5-oxo-tetrahydro-furan-3-ylcarbamoyl)-methyl]-6-[(3-methyoxy-benzenesulfonylamino)-methyl]-2-oxo-2,3,4,7-tetrahydro-1H-azepin-3-yl}-amide: $^1$H NMR (CD$_3$OD) δ 8.44 (s, 1H), 7.99–7.90 (m, 4H), 7.62–7.41 (m, 5H), 7.21–7.18 (d, J=8.1 Hz, 1H), 5.66 (bs, 1H), 5.42–5.37 (d, d, J=12.3, 4.2 Hz, 1H), 4.69–4.66 (d, d, J=4.5, 4.2 Hz, 1H), 4.64–4.59 (d, J=13.2 Hz, 1H), 4.41–4.32 (m 1H), 4.25–4.20 (d, J=16.2 Hz, 1H), 4.19–4.13 (d, J=17.4 Hz, 1H), 3.87 (s, 3H), 3.53–3.46 (m, 3H), 2.77–2.67 (m, 2H), 2.57–2.46 (m, 2H); MS 637.3 (M+H).

Naphthalene-2-carboxylic acid {1-[1-(2-hydroxy-5-oxo-tetrahydro-furan-3-ylcarbamoyl)-ethyl]-6-[(4-methoxy-benzenesulfonylamino)-(3R)-methyl]-2-oxo-2,3,4,7-tetrahydro-1H-azepin-3-yl}-amide: MS 651 (M+H).

Naphthalene-2-carboxylic acid {1-[1-(2-hydroxy-5-oxo-tetrahydro-furan-3-ylcarbamoyl)-ethyl]-6-[(4-methoxy-benzenesulfonylamino)-(3S)-methyl]-2-oxo-2,3,4,7-tetrahydro-1H-azepin-3-yl}-amide: MS 651 (M+H).

The compositions which comprise Category IV or the interleukin-1β converting enzyme inhibitors according to the present invention comprise a 4,6-substituted-[1,4]thiazepan-5-one ring system scaffold having the formula:

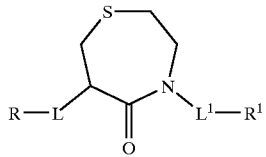

the first which comprises scaffolds having the formula:

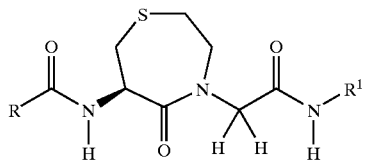

wherein R and R$^1$ are defined herein below in Table VI

TABLE VI

| No. | R | R$^1$ |
|---|---|---|
| 385 | phenyl | 2-hydroxy-5-oxo-tetrahydrofuran-3-yl |
| 386 | 3-fluorophenyl | 2-hydroxy-5-oxo-tetrahydrofuran-3-yl |
| 387 | 4-fluorophenyl | 2-hydroxy-5-oxo-tetrahydrofuran-3-yl |
| 388 | 3-trifluoromethylphenyl | 2-hydroxy-5-oxo-tetrahydrofuran-3-yl |
| 389 | 4-trifluoromethylphenyl | 2-hydroxy-5-oxo-tetrahydrofuran-3-yl |
| 390 | 3-methoxyphenyl | 2-hydroxy-5-oxo-tetrahydrofuran-3-yl |
| 391 | 4-methoxyphenyl | 2-hydroxy-5-oxo-tetrahydrofuran-3-yl |

TABLE VI-continued

| No. | R | R$^1$ |
|---|---|---|
| 392 | 3-acetylphenyl | 2-hydroxy-5-oxo-tetrahydrofuran-3-yl |
| 393 | 4-acetylphenyl | 2-hydroxy-5-oxo-tetrahydrofuran-3-yl |
| 394 | 3-benzoylphenyl | 2-hydroxy-5-oxo-tetrahydrofuran-3-yl |
| 395 | 1-naphthyl | 2-hydroxy-5-oxo-tetrahydrofuran-3-yl |
| 396 | 2-naphthyl | 2-hydroxy-5-oxo-tetrahydrofuran-3-yl |
| 397 | 2-quinolinyl | 2-hydroxy-5-oxo-tetrahydrofuran-3-yl |
| 398 | 1-isoquinolinyl | 2-hydroxy-5-oxo-tetrahydrofuran-3-yl |
| 399 | 2-benzothiaphenyl | 2-hydroxy-5-oxo-tetrahydrofuran-3-yl |
| 400 | phenyl | 2-ethoxy-5-oxo-tetrahydrofuran-3-yl |
| 401 | 3-fluorophenyl | 2-ethoxy-5-oxo-tetrahydrofuran-3-yl |
| 402 | 4-fluorophenyl | 2-ethoxy-5-oxo-tetrahydrofuran-3-yl |
| 403 | 3-trifluoromethylphenyl | 2-ethoxy-5-oxo-tetrahydrofuran-3-yl |
| 404 | 4-trifluoromethylphenyl | 2-ethoxy-5-oxo-tetrahydrofuran-3-yl |
| 405 | 3-methoxyphenyl | 2-ethoxy-5-oxo-tetrahydrofuran-3-yl |
| 406 | 4-methoxyphenyl | 2-ethoxy-5-oxo-tetrahydrofuran-3-yl |
| 407 | 3-acetylphenyl | 2-ethoxy-5-oxo-tetrahydrofuran-3-yl |
| 408 | 4-acetylphenyl | 2-ethoxy-5-oxo-tetrahydrofuran-3-yl |
| 409 | 3-benzoylphenyl | 2-ethoxy-5-oxo-tetrahydrofuran-3-yl |
| 410 | 1-naphthyl | 2-ethoxy-5-oxo-tetrahydrofuran-3-yl |
| 411 | 2-naphthyl | 2-ethoxy-5-oxo-tetrahydrofuran-3-yl |
| 412 | 2-quinolinyl | 2-ethoxy-5-oxo-tetrahydrofuran-3-yl |
| 413 | 1-isoquinolinyl | 2-ethoxy-5-oxo-tetrahydrofuran-3-yl |
| 414 | 2-benzothiaphenyl | 2-ethoxy-5-oxo-tetrahydrofuran-3-yl |

The compounds of Category IV can be suitably prepared by the procedure outlined herein below utilizing intermediate 37 which can be synthesized by the procedure described in Scheme XII.

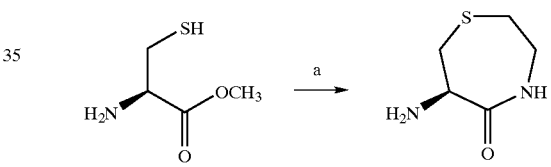

Reagents and conditions: a) aminochloroethane, HCl, Et$_3$N, MeOH.

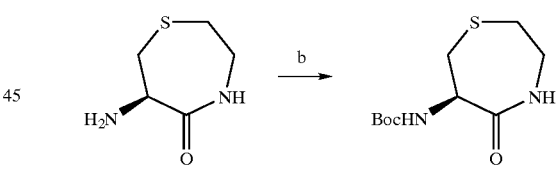

Reagents and conditions: b) (Boc)$_2$O, Et$_3$N, MeOH.

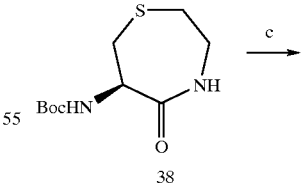

Reagents and conditions: c) KHMDS, BrCH$_2$CO$_2$C$_2$H$_5$, THF, -78° C., 2 hrs.

-continued

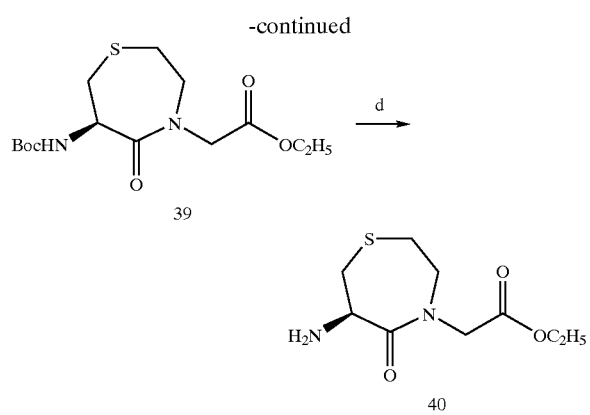

Reagents and conditions: d) TFA, dichloromethane.

Thiazepinone starting material, 6-amino-[1,4]thiazepan-5-one, 37, can be prepared from L-cysteine methylester and aminochloroethane hydrochloride via the procedure described by H. Tanaka et al., *FEBS Lett.*, 174, p. 76 (1984).

Preparation of (5-oxo-[1-,4]thiazepan-6-yl)-carbamic acid tert-butyl ester (38): To a solution of 6-amino-[1,4]thiazepan-5-one (37) (2.00 g, 13.70 mmol) in methanol (50 mL) is added Boc$_2$O (4.50 g, 20.50 mmol) and triethylamine (2.90 mL, 20.50 mmol). The reaction was stirred overnight at room temperature. The reaction mixture is concentrated in vacuo and the crude material obtained purified by flash chromatography on silica gel (EtOAc/hexanes) to afford the desired product 2 (2.40 g, 70%) as a light yellow oil; $^1$H NMR (CD$_3$OD): 6.04 (m, 2H), 4.76 (m, 1H), 3.76–2.66 (m, 2H), 2.83–2.67 (m, 4H), 1.49 (m, 9H); ESI MS 247.10 (M+H).

Preparation of (6-tert-butoxycarbonylamino-5-oxo-[1,4]thiazepa-4-yl)-acetic acid ethyl ester (39): A solution of the (5-oxo-[1-,4]thiazepan-6-yl)-carbamic acid tert-butyl ester (38) (0.20 g, 00.81 mmol) in THF (10 mL) is cooled to –78° C. and KHMDS (0.5 M in Toluene, 2.20 mL, 1.06 mmol) is added followed by ethyl bromoacetate (1.63 mmol, 0.20 mL). The reaction was stirred at –78° C. 2 hours. The solution is quenched with saturated ammonium chloride solution and extracted with ethyl acetate (3×20 mL). The organic layers are combined and dried over Na$_2$SO$_4$ and concentrated in vacuo. The resulting crude oil the desired product 36 is used without further purification.

Preparation of (6-amino-5-oxo-[1,4]thiazepa-4-yl)-acetic acid ethyl ester 40): To a solution of the (6-tert-butoxycarbonylamino-5-oxo-[1,4]thiazepa-4-yl)-acetic acid ethyl ester (39) (0.39 g, 1.16 mmol) in dichloromethane (3 mL) is added trifluoroacetic acid (3 mL). The solution is stirred for 3 hours at room temperature. The solution is concentrated in vacuo and treated with saturated NaHCO$_3$. Solid NaCl is added to the resulting aqueous solution and the solution is extracted with EtOAc. The organic layer was dried (MgSO$_4$) and concentrated in vacuo. The crude product obtained was then purified by flash chromatography on silica gel (EtOAc/hexanes) to afford the amine 37 (0.20 g, 74%) as a white foamy solid; $^1$H NMR (CD$_3$OD): δ 4.75 (dd, J=2.1, 9.6 Hz, 1H), 4.36–4.18 (m, 4H), 4.12–4.03 (m, 1H), 3.86 (ddd, J=1.8, 5.7, 16.5 Hz, 1H), 3.08 (m, 2H), 2.81–2.65 (m, 2H), 1.30 (m, 3H); ESI MS 233.09 (M+H).

Intermediate 40, prepared by the procedure herein above, can be reacted with a suitable reagent which introduces the selected R unit into the compound scaffold as described in Scheme XIII herein below.

Scheme XIII

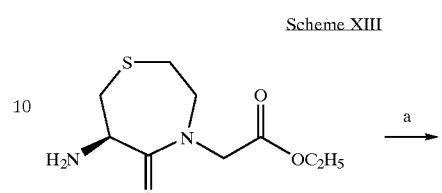

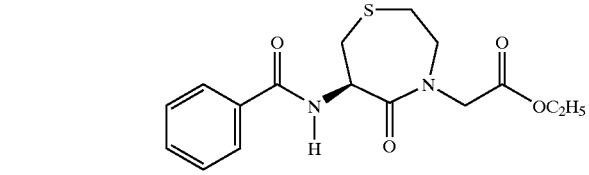

Reagents and conditions: a) benzoyl chloride, Et$_3$N, THF.

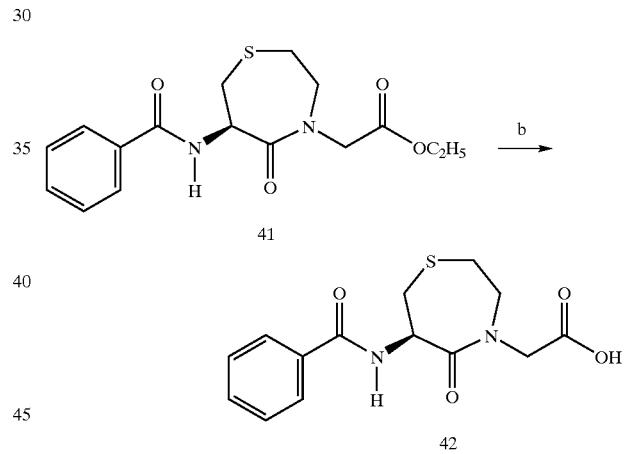

Reagents and conditions: b) LiOH, THF/H$_2$O, rt, 2.5 hrs.

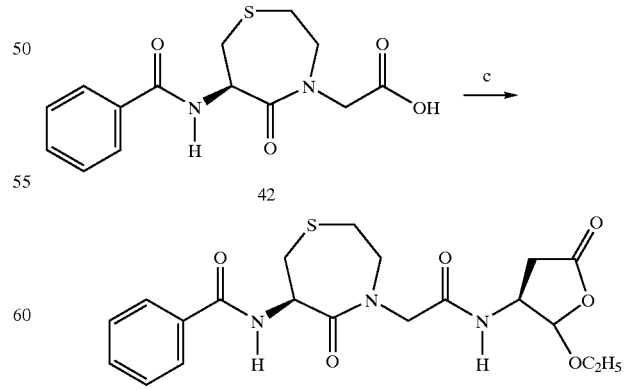

Reagents and conditions: c) (2-ethoxy-5-oxo-tetrahydrofurany-3-yl)-carbamic acid; N,N-dimethylbarbituric acid, (Ph$_3$P)$_4$Pd, CH$_2$Cl$_2$, EDCl, HOBt.

EXAMPLE 11

N-{4-[(2-ethoxy-5-oxo-tetrahydro-furan-3-ylcarbamoyl)-methyl]-5-oxo-1-[1,4]thiazepan-6-yl}-benzamide (43)

Preparation of (6-benzoylamino-5-oxo-[1,4]thiazepa-4-yl)-acetic acid ethyl ester (41): A solution of (6-amino-5-oxo-[1,4]thiazepa-4-yl)-acetic acid ethyl ester, 40, (0.40 g, 1.70 mmol) in THF (15 mL) is treated with Et₃N (0.36 mL, 2.59 mmol) followed by benzoyl chloride (0.22 mL, 1.87 mmol). The solution is stirred for 1.5 hours at room temperature before being quenched with MeOH and concentrated in vacuo. The crude product is then purified over silica gel (EtOAc/hexane) to afford (0.48 g, 84%) of the desired product as white crystalline material.

Preparation of (6-benzoylamino-5-oxo-[1,4]thiazepa-4-yl)-acetic acid (42): A solution of (6-benzoylamino-5-oxo-[1,4]thiazepa-4-yl)-acetic acid ethyl ester, 41, (0.14 g, 0.41 mmol) in 4 mL of 3:1 THF/H₂O is treated with excess LiOH and stirred for 2.5 hours at room temperature. The solution is then acidified and extracted with EtOAc. The EtOAc layer is dried (MgSO₄) and concentrated in vacuo to yield the desired product (0.11 g, 84%).

Preparation of N-{4-[(2-ethoxy-5-oxo-tetrahydro-furan-3-ylcarbamoyl)-methyl]-5-oxo-1-[1,4]thiazepan-6-yl}-benzamide (43): A catalytic amount of Pd(Ph₃P)₄ is added to a solution of (2-ethoxy-5-oxo-tetrahydrofuran-3-yl)-carbamic acid allyl ester (0.21 g, 0.93 mmol) and N,N-dimethylbarbituric acid (0.300, 1.86 mmol) in 15 mL CH₂Cl₂ at room temperature. The solution is stirred at room temperature for 15 minutes and (6-benzoylamino-5-oxo-[1,4]thiazepa-4-yl)-acetic acid, 42, (0.10 g, 0.31 mmol) is added as a solution in 1 mL CH₂Cl₂, followed by 1-hydroxybenzotriazole (0.11 g, 0.78 mmol) and 1-(3-dimethyl-aminopropyl)-3-ethyl-carbodiimide hydrochloride (0.15 g, 0.78 mmol). The solution is stirred for 5 hours then diluted with EtOAc, washed with saturated NaHCO₃, brine, dried (MgSO₄), and concentrated in vacuo. Purification over silica gel afforded 0.1 g of the desired product (74% yield).

The compounds of this category wherein R¹ comprises the cysteine trap 2-hydroxy-5-oxo-tetrahydrofuran-3-yl can be prepared by the procedure outlined in Scheme VII as indicated in the following example starting with compound 43.

Scheme XIV

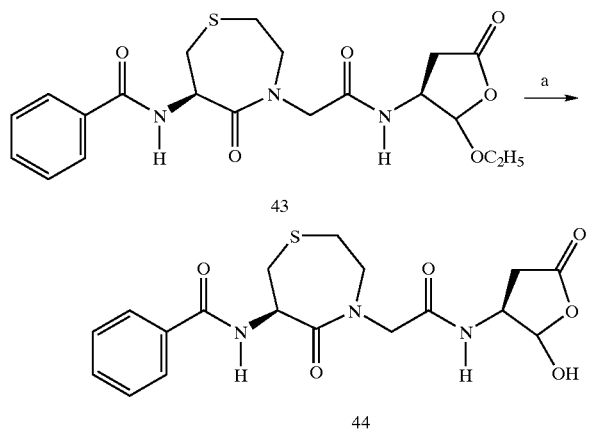

Reagents and conditions: a) TFA, acetonitrile/water.

EXAMPLE 12

N-{4-[(2-hydroxy-5-oxo-tetrahydro-furan-3-ylcarbamoyl)-methyl]-5-oxo-1-[1,4]thiazepan-6-yl}-benzamide (44)

Preparation of N-{4-[(2-hydroxy-5-oxo-tetrahydro-furan-3-ylcarbamoyl)-methyl]-5-oxo-1-[1,4]thiazepan-6-yl}-benzamide (44): A solution of N-{4-[(2-ethoxy-5-oxo-tetrahydro-furan-3-ylcarbamoyl)-methyl]-5-oxo-1-[1,4]thiazepan-6-yl}-benzamide, 43, (0.10 g, 0.26 mmol) in acetonitrile/water is treated with trifluoroacetic acid. After stirring for 3 hours the solution is concentrated in vacuo and the crude product purified by preparative reverse phase HPLC to afford (0.06 g, 58%) of the 8 as a white solid; ¹H NMR (CD₃OD): δ 7.93 (m, 2H), 7.61 (m, 1H), 7.52 (m, 2H), 5.48 (d, J=10.5 Hz, 1H), 4.66–4.59 (m, 1H), 4.49 (m, 1H), 4.34 (m, 2H), 4.00 (Abq, J=16.5 Hz, 1H), 3.77 (m, 2H), 3.68 (m, 1H), 3.42 (m, 1H), 3.25 (m, 1H), 2.70 (m, 1H), 2.51 (m, 1H); ESI MS 408.04 (M+H).

Other non-limiting examples of compounds which comprise this aspect of Category III include:

Naphthalene-2-carboxylic acid-{4-[(2-hydroxy-5-oxo-tetrahydro-furanyl-3-ylcarbamoyl)-methyl]-5-oxo-[1,4]thiazepan-6-yl]benzamide ¹H NMR (CD₃OD): δ 8.47 (bs, 1H), 8.05–7.92 (m, 4H), 7.62 (m, 2H), 5.43 (m, 1H), 4.64 (m, 1H), 4.36 (m, 1H), 4.24–4.12 (m, 3H), 3.86 (m, 1H), 2.99 (m, 3H), 2.71 (m, 2H), 2.55 (m, 1H), 1.21 (m, 1H); ESI MS 458.09 (M+H).

5-Chloro-N-{4-[(2-hydroxy-5-oxo-tetrahydro-furan-3-ylcarbamoyl)-methyl]-5-oxo-[1,4]thiazepan-6-yl}-2-methyl-benzamide ¹H NMR (CD₃OD): 7.49 (s, 1H), 7.38 (d, J=6.6 Hz, 1H), 7.28 (d, J=8.4 Hz, 1H), 5.32 (d, J=7.0 Hz, 1H), 4.63 (m, 1H), 4.34 (m, 1H), 4.18 (d, 2H), 4.09 (m, 1H), 3.83–3.78 (m, 1H), 3.06–2.93 (m, 2H), 2.88–2.83 (m, 2H), 2.75–2.66 (m, 2H), 2.55 (d, J=8.8 Hz, 1H), 2.42 (s, 3H). MS m/z 456 (M+H)⁺

Benzo[b]thiophene-2-carboxylic acid {4-[(2-hydroxy-5-oxo-tetrahydro-furan-3-ylcarbamoyl)-methyl]-5-oxo-[1,4]thiazepan-6-yl}-amide ¹H NMR (CD₃OD): 8.07 (s, 1H), 7.95 (dd, J=13.7, 1.5 Hz, 2H), 7.48 (m, 2H), 5.35 (d, J=7.3 Hz, 1H), 4.64 (m, 1H), 4.38–4.28 (m, 1H), 4.21 (dd, J=8.4, 1.8 Hz, 2H), 4.18–4.09 (m, 1H), 3.86–3.79 (m, 1H), 3.07–2.98 (m, 2H), 2.92–2.86 (dd, J=13.9,2.2 Hz, 1H), 2.75–2.67 (m, 2H), 2.58–2.52 (m, 2H). MS m/z 464 (M+H)⁺

Isoquinoline-1-carboxylic acid {4-[(2-hydroxy-5-oxo-tetrahydro-furan-3-ylcarbamoyl)-methyl]-5-oxo-[1,4]thiazepan-6-yl}-amide ¹H NMR (CD₃OD): δ 9.19 (d, J=8.6 Hz, 1H), 8.55 (d, J=5.5 Hz, 1H), 8.05 (m, 2H), 7.88 (m, 1H), 7.80 (m, 1H), 5.43 (t, 1H), 4.64 (m, 1H), 4.35 (m, 1H), 4.29–4.23 (d, J=19.1 Hz, 1H), 4.17–4.10 (m, 2H), 3.85 (m, 1H), 3.34 (m, 1H), 3.00 (m, 2H), 2.75–2.67 (m, 2H), 2.55 (m, 1H). MS m/z 459 (M+H)⁺

The fifth category of interleukin-1β converting enzyme inhibitors according to the present invention relates to compounds comprising a 4,6-substituted-[1,4]thiazepan-5-one ring system scaffold having the formula:

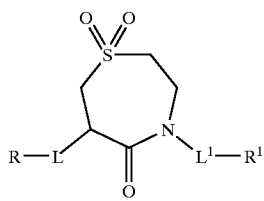

the first aspect of which comprises scaffolds having the formula:

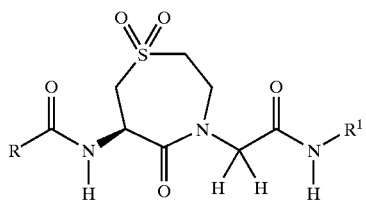

wherein R and R¹ are defined herein below in Table VII.

TABLE VII

| No. | R | R¹ |
|---|---|---|
| 415 | phenyl | 2-hydroxy-5-oxo-tetrahydrofuran-3-yl |
| 416 | 3-fluorophenyl | 2-hydroxy-5-oxo-tetrahydrofuran-3-yl |
| 417 | 4-fluorophenyl | 2-hydroxy-5-oxo-tetrahydrofuran-3-yl |
| 418 | 3-trifluoromethylphenyl | 2-hydroxy-5-oxo-tetrahydrofuran-3-yl |
| 419 | 4-trifluoromethylphenyl | 2-hydroxy-5-oxo-tetrahydrofuran-3-yl |
| 420 | 3-methoxyphenyl | 2-hydroxy-5-oxo-tetrahydrofuran-3-yl |
| 421 | 4-methoxyphenyl | 2-hydroxy-5-oxo-tetrahydrofuran-3-yl |
| 422 | 3-acetylphenyl | 2-hydroxy-5-oxo-tetrahydrofuran-3-yl |
| 423 | 4-acetylphenyl | 2-hydroxy-5-oxo-tetrahydrofuran-3-yl |
| 424 | 3-benzoylphenyl | 2-hydroxy-5-oxo-tetrahydrofuran-3-yl |
| 425 | 1-naphthyl | 2-hydroxy-5-oxo-tetrahydrofuran-3-yl |
| 426 | 2-naphthyl | 2-hydroxy-5-oxo-tetrahydrofuran-3-yl |
| 427 | 2-quinolinyl | 2-hydroxy-5-oxo-tetrahydrofuran-3-yl |
| 428 | 1-isoquinolinyl | 2-hydroxy-5-oxo-tetrahydrofuran-3-yl |
| 429 | 2-benzothiaphenyl | 2-hydroxy-5-oxo-tetrahydrofuran-3-yl |
| 430 | phenyl | 2-ethoxy-5-oxo-tetrahydrofuran-3-yl |
| 431 | 3-fluorophenyl | 2-ethoxy-5-oxo-tetrahydrofuran-3-yl |
| 432 | 4-fluorophenyl | 2-ethoxy-5-oxo-tetrahydrofuran-3-yl |
| 433 | 3-trifluoromethylphenyl | 2-ethoxy-5-oxo-tetrahydrofuran-3-yl |
| 434 | 4-trifluoromethylphenyl | 2-ethoxy-5-oxo-tetrahydrofuran-3-yl |
| 435 | 3-methoxyphenyl | 2-ethoxy-5-oxo-tetrahydrofuran-3-yl |
| 436 | 4-methoxyphenyl | 2-ethoxy-5-oxo-tetrahydrofuran-3-yl |
| 437 | 3-acetylphenyl | 2-ethoxy-5-oxo-tetrahydrofuran-3-yl |
| 438 | 4-acetylphenyl | 2-ethoxy-5-oxo-tetrahydrofuran-3-yl |
| 439 | 3-benzoylphenyl | 2-ethoxy-5-oxo-tetrahydrofuran-3-yl |
| 440 | 1-naphthyl | 2-ethoxy-5-oxo-tetrahydrofuran-3-yl |
| 441 | 2-naphthyl | 2-ethoxy-5-oxo-tetrahydrofuran-3-yl |
| 442 | 2-quinolinyl | 2-ethoxy-5-oxo-tetrahydrofuran-3-yl |
| 443 | 1-isoquinolinyl | 2-ethoxy-5-oxo-tetrahydrofuran-3-yl |
| 444 | 2-benzothiaphenyl | 2-ethoxy-5-oxo-tetrahydrofuran-3-yl |

The compounds of Category V can be suitably prepared by the procedure outlined herein below utilizing intermediate 43, which can be synthesized by the procedure described in Scheme XV.

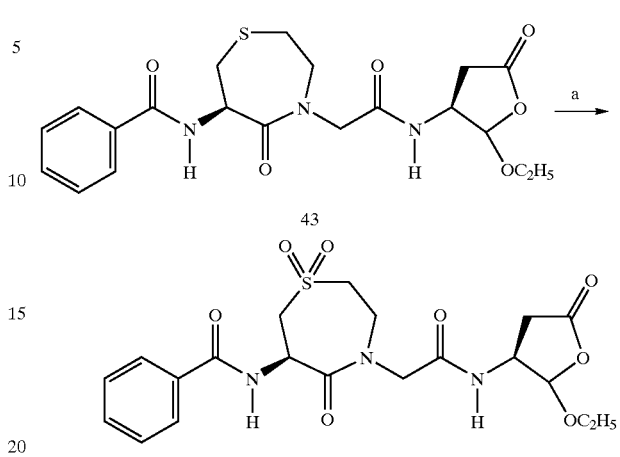

Reagents and conditions: a) m-CPBA, DCM, rt 1 hr.

EXAMPLE 13

N-{4-[(2-Ethoxy-5-oxo-tetrahydro-furan-3-ylcarbamoyl)-methyl]-1,1,5-trioxo-1$\lambda^6$-[1,4]thiazepan-6-yl}-benzamide (45)

Preparation of N-{4-[(2-ethoxy-5-oxo-tetrahydro-furan-3-ylcarbamoyl)-methyl]-1,1,5-trioxo-1$\lambda^6$-[1,4]thiazepan-6-yl}-benzamide (42): To a solution of N-{4-[(2-ethoxy-5-oxo-tetrahydro-furan-3-ylcarbamoyl)-methyl]-5-oxo-1-[1,4]thiazepan-6-yl}-benzamide, 40, (0.02 g, 0.04 mmol) in dichloromethane (3 mL) is added NaHCO$_3$ (0.01 g, 0.08 mmol) followed by m-chloroperbenzoic acid (0.03 g, 0.08 mmol). The reaction mixture is stirred at room temperature for 1 hour. The reaction mixture is then filtered and triturated with ether (3×10 mL), and the crude product purified by preparative reverse phase HPLC to afford 0.01 g (71% yield) of the desired product as a white solid.

The compounds of this category wherein R¹ comprises the cysteine trap 2-hydroxy-5-oxo-tetrahydrofuran-3-yl can be prepared by the procedure outlined in Scheme XVI as indicated in the following example starting with compound 45.

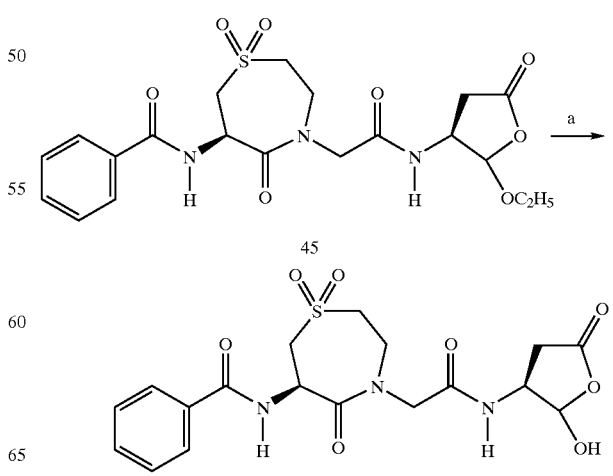

-continued
Reagents and conditions: a) TFA, acetonitrile/water.

EXAMPLE 14

N-{4-[(2-Hydroxy-5-oxo-tetrahydro-furan-3-ylcarbamoyl)-methyl]-1,1,5-trioxo-1λ$^6$-[1,4]thiazepan-6-yl}-benzamide (46)

Preparation of N-{4-[(2-hydroxy-5-oxo-tetrahydro-furan-3-ylcarbamoyl)-methyl]-1,1,5-trioxo-1λ$^6$-[1,4]thiazepan-6-yl}-benzamide (46): A solution of N-{4-[(2-ethoxy-5-oxo-tetrahydro-furan-3-ylcarbamoyl)-methyl]-1,1,5-trioxo-1λ$^6$-[1,4]thiazepan-6-yl}-benzamide, 45, (0.03 g, 0.05 mmol) in acetonitrile/water is treated with trifluoroacetic acid. After stirring for 3 hours the solution is concentrated in vacuo and the crude product purified by preparative reverse phase HPLC to afford 0.02 g (77% -yield) of the desired product as a white solid.) $^1$H NMR (CD$_3$OD): δ 7.90 (m, 2H), 7.62–7.46 (m, 3H), 5.46 (d, J=10.5 Hz, 1H), 4.61 (m, 1H), 4.51 (dd, J=16.3, 5.1 Hz, 1H), 4.36 (m, 2H), 4.02 (dd, J=16.0, 3.3 Hz, 1H), 3.84–3.64 (m, 3H), 3.42 (m, 1H), 3.26 (m, 1H), 2.68 (m, 1H), 2.52 (m, 1H); ESI MS 440.06 (M+H).

Other non-limiting examples of compounds which comprise this aspect of Category III include:

5-Chloro-N-{4-[(2-hydroxy-5-oxo-tetrahydro-furan-3-ylcarbamoyl)-methyl]-1,1,5-trioxo-1λ$^6$-[1,4]thiazepan-6-yl}-2-methyl-benzamide $^1$H NMR (CD$_3$OD): 7.55 (d, J=1.2 Hz, 1H), 7.40 (dd, J=8.2, 2.2 Hz, 1H), 7.28 (d, J=8.0 Hz, 1H), 5.43 (d, J=11.0 Hz, 1H), 4.63 (m, 1H), 4.54–4.48 (dd, J=16.6, 4.7 Hz, 1H), 4.35 (m, 2H), 4.01 (dd, J=16.1, 2.4H, 1H), 3.84–3.74 (m, 2H), 3.68 (m, 1H), 3.42–3.35 (m, 2H), 2.67 (m, 1H), 2.54 (m, 1H), 2.43 (s, 3H). MS m/z 488 (M+H)

Naphthalene-2-carboxylic acid{4-[(2-hydroxy-5-oxo-tetrahydro-furanyl-3-ylcarbamoyl)-methyl]-1,1,5-trioxo-1λ$^6$-[1,4]thiazepan-6-yl]benzamide $^1$H NMR (CD$_3$OD): δ 8.49 (bs, 1H), 8.04 (m, 4H), 7.62 (m, 2H), 5.54 (d, J=10.2 Hz, 1H), 4.64 (m, 1H), 4.53 (dd, J=16.5, 5.7 Hz, 1H), 4.36 (m, 2H), 4.05 (Abq, J=16.5 Hz, 1H), 3.87–3.69 (m, 3H), 3.50 (m, 1H), 3.26 (m, 1H), 2.68 (m, 1H), 2.53 (m, 1H); ESI MS 490.08 (M+H).

Benzo[b]thiophene-2-carboxylic acid {4-[(2-hydroxy-5-oxo-tetrahydro-furan-3-ylcarbamoyl)-methyl]-1,1,5-trioxo-1λ$^6$-[1,4]thiazepan-6-yl}-amide $^1$H NMR (CD$_3$OD): 8.08 (s, 1H), 7.94 (dd, J=4.7, 3.0 Hz, 2H), 7.47 (m, 2H), 5.48 (d, J=10.6 Hz, 1H), 4.64 (m, 1H), 4.55–4.48 (dd, J=16.5, 5.5 Hz, 1H), 4.38–4.29 (m, 2H), 4.07–4.01 (dd, J=16.3, 3.4 Hz, 1H), 3.85–3.73 (m, 2H), 3.72–3.68 (d, J=11.0,1H), 3.48–3.44 (dd, J=13.9, 3.0 Hz, 1H), 3.35–3.28 (m, 1H), 2.73–2.66 (m, 1H), 2.56–2.53 (m, 1H). MS m/z 494 (M+H)

Isoquinoline-1-carboxylic acid {4-[(2-hydroxy-5-oxo-tetrahydro-furan-3-ylcarbamoyl)-methyl]-1,1,5-trioxo-1λ$^6$-[1,4]thiazepan-6-yl}-amide $^1$H NMR (CD$_3$OD): 9.27 (d, J=9.2 Hz, 1H), 8.56 (d, 1H), 8.03 (d, J=6.6 Hz, 2H), 7.88–7.75 (m, 2H), 5.56–5.53 (d, J=10.6 Hz, 1H), 4.67–4.63 (m, 1H), 4.51–4.44 (dd, J=16.3, 3.8 Hz, 1H), 4.40–4.32 (m, 2H), 4.17–4.11 (d, J=16.9 Hz, 1H), 3.86–3.74 (m, 2H), 3.70–3.60 (m, 1H), 3.55–3.51 (m, 1H), 3.38–3.29 (m, 1H), 2.74–2.67 (m, 1H), 2.58–2.54 (m, 1H). MS m/z 491 (M+H)

The cysteine traps of the present invention can be prepared by any convenient method selected by the formulator. The following is a description of the preparation of (2-ethoxy-5-oxo-tetrahydrofuran-3-yl)-carbamic acid allyl ester which is used to introduce one category of cysteine trap into the scaffolds of the present invention.

Scheme XVIII

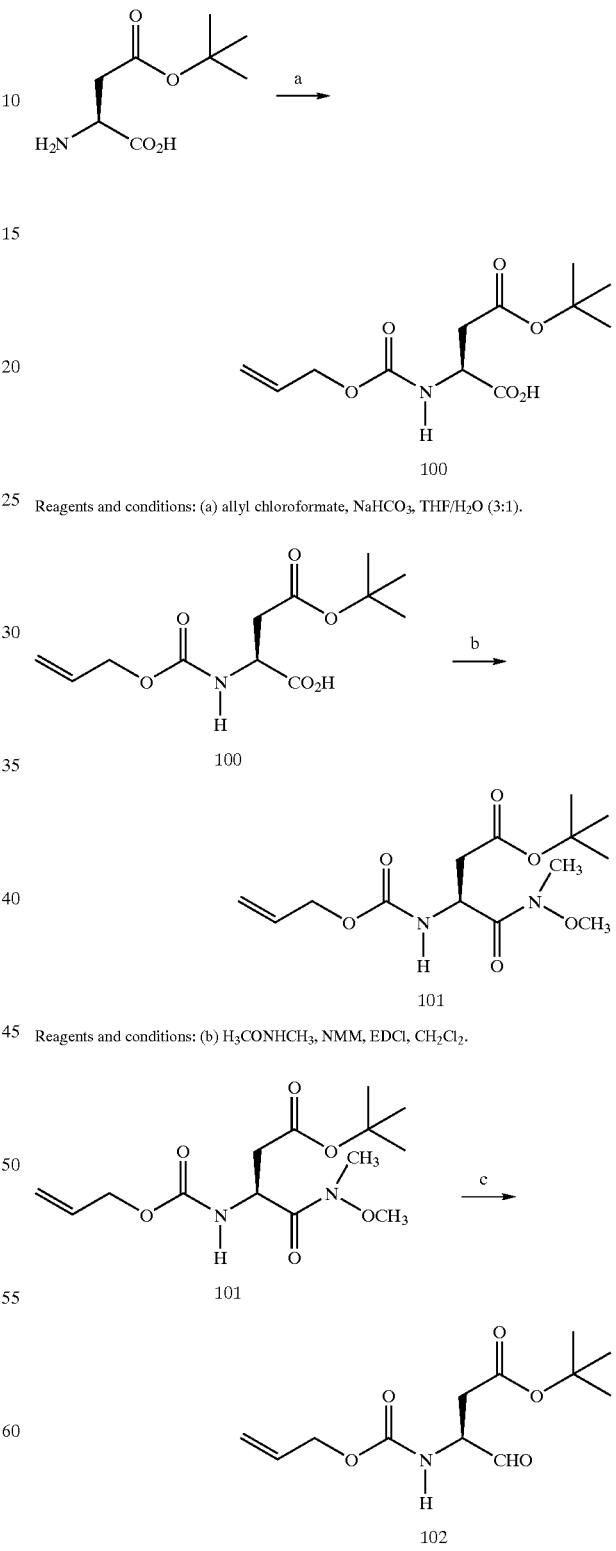

Reagents and conditions: (a) allyl chloroformate, NaHCO$_3$, THF/H$_2$O (3:1).

Reagents and conditions: (b) H$_3$CONHCH$_3$, NMM, EDCl, CH$_2$Cl$_2$.

Reagents and conditions: (c) LAH, THF/H$_2$O (3:1).

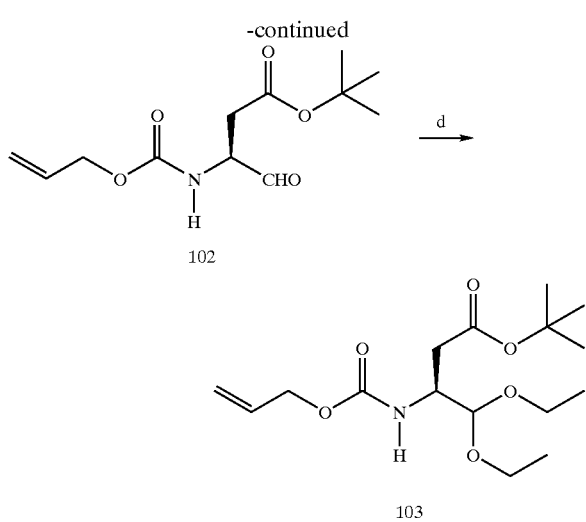

Reagents and conditions: (d) CH(OC₂H₅)₃, PTSA, EtOH.

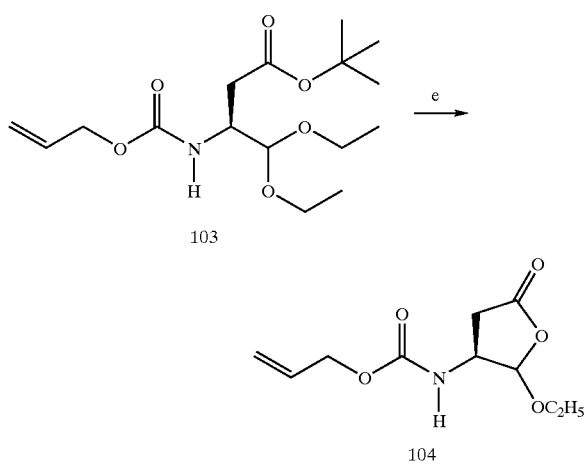

Reagents and conditions: (e) TFA, CH₂Cl₂.

EXAMPLE 13

(2-Ethoxy-5-oxo-tetrahydro-furan-3-yl)-carbamic acid allyl ester (104)

Preparation of 2-allyloxycarbonylamino-succinic acid 4-tert-butyl ester (100): L-aspartic acid β-t-butyl ester (30.3 g, 0.160 mol) is dissolved in 100 mL THF and 300 mL H₂O. Under cooling (ice bath) and with stirring, allyl chloroformate (38.8 mL, 44.1 g, 0.365 mol) and sodium bicarbonate (60.1 g, 0.715 mol) are added in one portion. After the consumption of the starting material, the mixture is acidified to a pH of 2 using 6 N HCl and then extracted with ether (3×400 mL). The ether layer is dried with MgSO₄ and concentrated under reduced pressure. The residue is purified over silica (CH₂Cl₂/MeOH/acetic acid 3:97:0.1) to furnish 40.7 g (90% yield) of the desired product as a clear oil.

Preparation of 3-allyloxycarbonylamino-N-methoxy-N-methyl-succinamic acid tert-butyl ester (101): 2-Allyloxycarbonylamino-succinic acid 4-tert-butyl ester, 100, (43.4 g, 0.159 mol) is dissolved in CH₂Cl₂ (900 mL). To this solution O,N-dimethyl-hydroxylamine hydrochloride (18.6 g, 0.191 mol), 4-Methyl-morpholine (21.0 mL, 19.3 g, 0.191 mol), and 1-(3-Dimethylaminopropyl)-3-ethylcarbodiimide hydrochloride (36.6 g, 0.191 mol) are added. After the consumption of the starting material, the solution is washed with 1.0 N HCl (2×400 mL) and brine (1×250 mL). The organic layer is concentrated in vacuo and the residue purified over silica (hexanes/ethyl acetate 65:35) to afford 40.8 g (81% yield) of the desired product as a clear oil.

Preparation of 3-allyloxycarbonylamino-4-oxo-butyric acid tert-butyl ester (102): A solution of 3-allyloxycarbonylamino-N-methoxy-N-methyl-succinamic acid tert-butyl ester, 101, (24.3 g, 76.8 mmol) in THF (60 mL) is treated at −78° C. with lithium aluminum hydride (1 M in THF, 39 mL, 39 mmol) dissolved in ether (200 mL) over 5 minutes. After the consumption of starting material, the solution is cautiously quenched with 1.0 N HCl, washed with 1.0 N HCl (2×100 mL) and brine (1×150 mL). The organic layer is concentrated in vacuo to afford 18.2 g (91% yield) of the desired product as a clear oil.

Preparation of 3-allyloxycarbonylamino-4,4-diethoxybutyric acid tert-butyl ester (103): To a solution of 3-allyloxycarbonylamino-4-oxo-butyric acid tert-butyl ester, 102, (13.3 g, 51.7 mmol) in anhydrous ethanol (75 mL) is added ethyl orthoformate (45 mL, 0.270 mol), p-toluenesulfonic acid (0.15 g, cat.) and 4 Å molecular sieves (10 g, kiln dried) under N₂. After the consumption of starting material, the sieves are removed by filtration and the solvent removed in vacuo to provide the desired compound as a clear oil which is used directly without further purification. MS (ESI): m/e=332.21 (M+H).

Preparation of (2-ethoxy-5-oxo-tetrahydro-furan-3-yl)-carbamic acid allyl ester (104). A solution of the crude 3-Allyloxycarbonylamino-4,4-diethoxy-butyric acid tert-butyl ester, 103, obtained in the procedure above, in CH₂Cl₂ (50 mL) is treated with triflouroacetic acid (50 mL). After the consumption of starting material, the organics are reduced under vacuum. The residual triflouroacetic acid is removed with ethyl acetate by azeotroping conditions. The final residue is purified over silica (hexanes/ethyl acetate 80:20) to afford 10.1 g (85% yield) of the desired product as a slightly yellow oil. ¹H-NMR, (300 MHz, CDCl₃): δ 1.23 (m, 3H), 2.41–2.54 (m, 1H), 2.82–3.06 (m, 2H), 3.61–3.73 (m, 1H), 3.82–3.98 (m, 1H), 4.06–4.25 (m, 1H), 4.61 (br s, 2H), 5.24–5.53 (m, 3H), 5.86–6.01 (m, 1H); MS (ESI): m/e=230.03 (M+H).

The following are non-limiting examples of other analogs prepared by the procedures described herein above.

N-{1-[(2-Hydroxy-5-oxo-tetrahydrofuran-3-ylcarbamoyl)methyl]-6-methyl-2-oxo-2,3,4,7-tetrahydro-1H-azepin-3-yl}-benzamide;

N-{1-[(2-Ethoxy-5-oxo-tetrahydrofuran-3-ylcarbamoyl)methyl]-6-methyl-2-oxo-2,3,4,7-tetrahydro-1H-azepin-3-yl}-benzamide;

N-{1-[(2-Hydroxy-5-oxo-tetrahydrofuran-3-yl-carbamoyl)methyl]-6-(benzene-sulfonylaminomethyl)-2-oxo-2,3,4,7-tetrahydro-1H-azepin-3-yl}-benzamide;

N-{1-[(2-Ethroxy-5-oxo-tetrahydrofuran-3-yl-carbamoyl)methyl]-6-(benzene-sulfonylaminomethyl)-2-oxo-2,3,4,7-tetrahydro-1H-azepin-3-yl}-benzamide Naphthalene-1-carboxylic acid {1-[(2-hydroxy-5-oxo-tetrahydrofuran-3-yl-carbamoyl)methyl]-6-methyl-2-oxo-2,3,4,7-tetrahydro-1H-azepin-3-yl}-amide;

Naphthalene-1-carboxylic acid {1-[(2-ethoxy-5-oxo-tetrahydrofuran-3-yl-carbamoyl)methyl]-6-methyl-2-oxo-2,3,4,7-tetrahydro-1H-azepin-3-yl}-amide;

Naphthalene-1-carboxylic acid {6-(benzenesulfonylaminomethyl)-1-[(2-hydroxy-5-oxo-tetrahydrofuran-3-yl-carbamoyl)methyl]-2-oxo-2,3,4,7-tetrahydro-1H-azepin-3-yl}-amide;

Naphthalene-1-carboxylic acid {6-(benzenesulfonylaminomethyl)-1-[(2-ethoxy-5-oxo-tetrahydrofuran-3-yl-carbamoyl)methyl]-2-oxo-2,3,4,7-tetrahydro-1H-azepin-3-yl}-amide;
Naphthylene-1-carboxylic acid {6-benzylaminomethyl-1-[(2-hydroxy-5-oxo-tetrahydrofuran-3-yl-carbamoyl)methyl]-2-oxo-2,3,4,7-tetrahydro-1H-azepin-3-yl}-amide;
Naphthylene-1-carboxylic acid {6-benzylaminomethyl-1-[(2-ethoxy-5-oxo-tetrahydrofuran-3-yl-carbamoyl)methyl]-2-oxo-2,3,4,7-tetrahydro-1H-azepin-3-yl}-amide;
Isoquinoline-1-carboxylic acid {1-[(2-hydroxy-5-oxo-tetrahydrofuran-3-yl-carbamoyl)methyl]-6-methyl-2-oxo-2,3,4,7-tetrahydro-1H-azepin-3-yl}-amide;
Isoquinoline-1-carboxylic acid {1-[(2-ethoxy-5-oxo-tetrahydrofuran-3-yl-carbamoyl)methyl]-6-methyl-2-oxo-2,3,4,7-tetrahydro-1H-azepin-3-yl}-amide;
Isoquinoline-1-carboxylic acid {6-(benzenesulfonylaminomethyl)-1-[(2-hydroxy-5-oxo-tetrahydrofuran-3-yl-carbamoyl)methyl]-2-oxo-2,3,4,7-tetrahydro-1H-azepin-3-yl}-amide;
Isoquinoline-1-carboxylic acid {6-(benzenesulfonylaminomethyl)-1-[(2-ethoxy-5-oxo-tetrahydrofuran-3-yl-carbamoyl)methyl]-2-oxo-2,3,4,7-tetrahydro-1H-azepin-3-yl}-amide;
Isoquinoline-1-carboxylic acid {6-(methylsulfonylaminomethyl)-1-[(2-hydroxy-5-oxo-tetrahydrofuran-3-yl-carbamoyl)methyl]-2-oxo-2,3,4,7-tetrahydro-1H-azepin-3-yl}-amide;
Isoquinoline-1-carboxylic acid {6-(benzenesulfonylaminomethyl)-1-[(2-ethoxy-5-oxo-tetrahydrofuran-3-yl-carbamoyl)methyl]-2-oxo-2,3,4,7-tetrahydro-1H-azepin-3-yl}-amide;
Isoquinoline-1-carboxylic acid {6-(benzoylaminomethyl)-1-[(2-hydroxy-5-oxo-tetrahydrofuran-3-yl-carbamoyl)methyl]-2-oxo-2,3,4,7-tetrahydro-1H-azepin-3-yl}-amide;
Isoquinoline-1-carboxylic acid {6-(benzoylaminomethyl)-1-[(2-ethoxy-5-oxo-tetrahydrofuran-3-yl-carbamoyl)methyl]-2-oxo-2,3,4,7-tetrahydro-1H-azepin-3-yl}-amide;
Isoquinoline-1-carboxylic acid {6-morpholinomethyl-1-[(2-hydroxy-5-oxo-tetrahydrofuran-3-yl-carbamoyl)methyl]-2-oxo-2,3,4,7-tetrahydro-1H-azepin-3-yl}-amide;
Isoquinoline-1-carboxylic acid {6-morpholinomethyl-1-[(2-ethoxy-5-oxo-tetrahydrofuran-3-yl-carbamoyl)methyl]-2-oxo-2,3,4,7-tetrahydro-1H-azepin-3-yl}-amide;
Isoquinoline-1-carboxylic acid {6-allylaminomethyl-1-[(2-hydroxy-5-oxo-tetrahydrofuran-3-yl-carbamoyl)methyl]-2-oxo-2,3,4,7-tetrahydro-1H-azepin-3-yl}-amide;
Isoquinoline-1-carboxylic acid {6-allylaminomethyl-1-[(2-ethoxy-5-oxo-tetrahydrofuran-3-yl-carbamoyl)methyl]-2-oxo-2,3,4,7-tetrahydro-1H-azepin-3-yl}-amide;
Isoquinoline-1-carboxylic acid {6-phenylaminomethyl-1-[(2-hydroxy-5-oxo-tetrahydrofuran-3-yl-carbamoyl)methyl]-2-oxo-2,3,4,7-tetrahydro-1H-azepin-3-yl}-amide;
Isoquinoline-1-carboxylic acid {6-phenylaminomethyl-1-[(2-ethoxy-5-oxo-tetrahydrofuran-3-yl-carbamoyl)methyl]-2-oxo-2,3,4,7-tetrahydro-1H-azepin-3-yl}-amide;
Isoquinoline-1-carboxylic acid {6-benzylaminomethyl-1-[(2-hydroxy-5-oxo-tetrahydrofuran-3-yl-carbamoyl)methyl]-2-oxo-2,3,4,7-tetrahydro-1H-azepin-3-yl}-amide;
Isoquinoline-1-carboxylic acid {6-benzylaminomethyl-1-[(2-ethoxy-5-oxo-tetrahydrofuran-3-yl-carbamoyl)methyl]-2-oxo-2,3,4,7-tetrahydro-1H-azepin-3-yl}-amide;
Isoquinoline-1-carboxylic acid {6-piperidin-1-ylmethyl-1-[(2-hydroxy-5-oxo-tetrahydrofuran-3-yl-carbamoyl)methyl]-2-oxo-2,3,4,7-tetrahydro-1H-azepin-3-yl}-amide;
Isoquinoline-1-carboxylic acid {6-piperidin-1-ylmethyl-1-[(2-ethoxy-5-oxo-tetrahydrofuran-3-yl-carbamoyl)methyl]-2-oxo-2,3,4,7-tetrahydro-1H-azepin-3-yl}-amide;
Isoquinoline-1-carboxylic acid {6-hydroxymethyl-1-[(2-hydroxy-5-oxo-tetrahydrofuran-3-yl-carbamoyl)methyl]-2-oxo-2,3,4,7-tetrahydro-1H-azepin-3-yl}-amide;
Isoquinoline-1-carboxylic acid {6-hydroxymethyl-1-[(2-ethoxy-5-oxo-tetrahydrofuran-3-yl-carbamoyl)methyl]-2-oxo-2,3,4,7-tetrahydro-1H-azepin-3-yl}-amide;
Benzo[b]thiophene-2-carboxylic {1-[(2-hydroxy-5-oxo-tetrahydrofuran-3-yl-carbamoyl)methyl]-2-oxo-2,3,4,7-tetrahydro-1H-azepin-3-yl}-amide;
Benzo[b]thiophene-2-carboxylic {1-[(2-ethoxy-5-oxo-tetrahydrofuran-3-yl-carbamoyl)methyl]-2-oxo-2,3,4,7-tetrahydro-1H-azepin-3-yl}-amide.
N-{1-[(2-Hydroxy-5-oxo-tetrahydrofuran-3-ylcarbamoyl)methyl]-2-oxo-2,3,4,7-tetrahydro-1H-azepin-3-yl}-benzamide;
N-{1-[(2-Ethoxy-5-oxo-tetrahydrofuran-3-ylcarbamoyl)methyl]-2-oxo-2,3,4,7-tetrahydro-1H-azepin-3-yl}-benzamide;
Isoquinoline-1-carboxylic acid {1-[(2-hydroxy-5-oxo-tetrahydrofuran-3-yl-carbamoyl)methyl]-2-oxo-2,3,4,7-tetrahydro-1H-azepin-3-yl}-amide;
Isoquinoline-1-carboxylic acid {1-[(2-ethoxy-5-oxo-tetrahydrofuran-3-yl-carbamoyl)methyl]-2-oxo-2,3,4,7-tetrahydro-1H-azepin-3-yl}-amide;
Naphthylene-1-carboxylic acid {1-[(2-hydroxy-5-oxo-tetrahydrofuran-3-yl-carbamoyl)methyl]-2-oxo-2,3,4,7-tetrahydro-1H-azepin-3-yl}-amide;
Naphthylene-1-carboxylic acid {1-[(2-ethoxy-5-oxo-tetrahydrofuran-3-yl-carbamoyl)methyl]-2-oxo-2,3,4,7-tetrahydro-1H-azepin-3-yl}-amide;
Benzo[b]thiophene-2-carboxylic {1-[(2-hydroxy-5-oxo-tetrahydrofuran-3-yl-carbamoyl)methyl]-2-oxo-2,3,4,7-tetrahydro-1H-azepin-3-yl}-amide;
Benzo[b]thiophene-2-carboxylic {1-[(2-ethoxy-5-oxo-tetrahydrofuran-3-yl-carbamoyl)methyl]-2-oxo-2,3,4,7-tetrahydro-1H-azepin-3-yl}-amide;
3-Fluoro-N-{1-[(2-hydroxy-5-oxo-tetrahydrofuran-3-ylcarbamoyl)methyl]-2-oxo-2,3,4,7-tetrahydro-1H-azepin-3-yl}-benzamide;
3-Fluoro-N-{1-[(2-ethoxy-5-oxo-tetrahydrofuran-3-ylcarbamoyl)methyl]-2-oxo-2,3,4,7-tetrahydro-1H-azepin-3-yl}-benzamide;
3-Trifluoromethyl-N-{1-[(2-hydroxy-5-oxo-tetrahydrofuran-3-ylcarbamoyl)methyl]-2-oxo-2,3,4,7-tetrahydro-1H-azepin-3-yl}-benzamide;
3-Trifluoromethyl-N-{1-[(2-ethoxy-5-oxo-tetrahydrofuran-3-ylcarbamoyl)methyl]-2-oxo-2,3,4,7-tetrahydro-1H-azepin-3-yl}-benzamide;
3-Acetyl-N-{1-[(2-hydroxy-5-oxo-tetrahydrofuran-3-ylcarbamoyl)methyl]-2-oxo-2,3,4,7-tetrahydro-1H-azepin-3-yl}-benzamide;
3-Acetyl-N-{1-[(2-ethoxy-5-oxo-tetrahydrofuran-3-ylcarbamoyl)methyl]-2-oxo-2,3,4,7-tetrahydro-1H-azepin-3-yl}-benzamide;
3-Benzoyl-N-{1-[(2-hydroxy-5-oxo-tetrahydrofuran-3-ylcarbamoyl)methyl]-2-oxo-2,3,4,7-tetrahydro-1H-azepin-3-yl}-benzamide;
3-Benzoyl-N-{1-[(2-ethoxy-5-oxo-tetrahydrofuran-3-ylcarbamoyl)methyl]-2-oxo-2,3,4,7-tetrahydro-1H-azepin-3-yl}-benzamide;
3-Methoxy-N-{1-[(2-hydroxy-5-oxo-tetrahydrofuran-3-ylcarbamoyl)methyl]-2-oxo-2,3,4,7-tetrahydro-1H-azepin-3-yl}-benzamide;

3-Methoxy-N-{1-[(2-ethoxy-5-oxo-tetrahydrofuran-3-ylcarbamoyl)methyl]-2-oxo-2,3,4,7-tetrahydro-1H-azepin-3-yl}-benzamide.

N-{4-[(2-Hydroxy-5-oxo-tetrahydrofuran-3-ylcarbamoyl)methyl]-5-oxo-[1,4]thiazepan-6-yl}-benzamide;

N-{4-[(2-Ethoxy-5-oxo-tetrahydrofuran-3-ylcarbamoyl)methyl]-5-oxo-[1,4]thiazepan-6-yl}-benzamide;

Naphthalene-2-carboxylic acid {4-[(2-hydroxy-5-oxo-tetrahydrofuran-3-ylcarbamoyl)methyl]-5-oxo-[1,4]thiazepan-6-yl}-amide;

Naphthalene-2-carboxylic acid {4-[(2-ethoxy-5-oxo-tetrahydrofuran-3-ylcarbamoyl)methyl]-5-oxo-[1,4]thiazepan-6-yl}-amide;

Isoquinoline-1-carboxylic acid {4-[(2-hydroxy-5-oxo-tetrahydrofuran-3-ylcarbamoyl)methyl]-5-oxo-[1,4]thiazepan-6-yl}-amide;

Isoquinoline-1-carboxylic acid {4-[(2-ethoxy-5-oxo-tetrahydrofuran-3-ylcarbamoyl)methyl]-5-oxo-[1,4]thiazepan-6-yl}-amide;

3-Fluoro-N-{4-[(2-hydroxy-5-oxo-tetrahydrofuran-3-ylcarbamoyl)methyl]-5-oxo-[1,4]thiazepan-6-yl}-benzamide;

3-Fluoro-N-{4-[(2-Ethoxy-5-oxo-tetrahydrofuran-3-ylcarbamoyl)methyl]-5-oxo-[1,4]thiazepan-6-yl}-benzamide;

3-Trifluoromethyl-N-{4-[(2-hydroxy-5-oxo-tetrahydrofuran-3-ylcarbamoyl)methyl]-5-oxo-[1,4]thiazepan-6-yl}-benzamide;

3-Trifluoromethyl-N-{4-[(2-ethoxy-5-oxo-tetrahydrofuran-3-ylcarbamoyl)methyl]-5-oxo-[1,4]thiazepan-6-yl}-benzamide.

N-{4-[(2-Hydroxy-5-oxo-tetrahydrofuran-3-ylcarbamoyl)methyl]-1,1,5-trioxo-1$\lambda^6$-[1,4]thiazepan-6-yl}-benzamide;

N-{4-[(2-Ethoxy-5-oxo-tetrahydrofuran-3-ylcarbamoyl)methyl]-1,1,5-trioxo-1$\lambda^6$-[1,4]thiazepan-6-yl}-benzamide;

Naphthalene-2-carboxylic acid {4-[(2-hydroxy-5-oxo-tetrahydrofuran-3-ylcarbamoyl)methyl]-1,1,5-trioxo-1$\lambda^6$-[1,4]thiazepan-6-yl}-amide;

Naphthalene-2-carboxylic acid {4-[(2-ethoxy-5-oxo-tetrahydrofuran-3-ylcarbamoyl)methyl]-1,1,5-trioxo-1$\lambda^6$-[1,4]thiazepan-6-yl}-amide;

Isoquinoline-1-carboxylic acid {4-[(2-hydroxy-5-oxo-tetrahydrofuran-3-ylcarbamoyl)methyl]-1,1,5-trioxo-1$\lambda^6$-[1,4]thiazepan-6-yl}-amide;

Isoquinoline-1-carboxylic acid {4-[(2-ethoxy-5-oxo-tetrahydrofuran-3-ylcarbamoyl)methyl]-1,1,5-trioxo-1$\lambda^6$-[1,4]thiazepan-6-yl}-amide.

Formulations

The present invention also relates to compositions or formulations which comprise the interleukin-1β converting enzyme inhibitors according to the present invention. In general, the compositions of the present invention comprise:

a) an effective amount of one or more interleukin-1β converting enzyme inhibitors according to the present invention; and b) one or more pharmaceutically acceptable excipients.

For the purposes of the present invention the term "excipient" and "carrier" are used interchangeably throughout the description of the present invention and said terms are defined herein as, "ingredients which are used in the practice of formulating a safe and effective pharmaceutical composition."

The formulator will understand that excipients are used primarily to serve in delivering a safe, stable, and functional pharmaceutical, serving not only as part of the overall vehicle for delivery but also as a means for achieving effective absorption by the recipient of the active ingredient. An excipient may fill a role as simple and direct as being an inert filler, or an excipient as used herein may be part of a pH stabilizing system or coating to insure delivery of the ingredients safely to the stomach. The formulator can also take advantage of the fact the compounds of the present invention have improved cellular potency, pharmacokinetic properties, as well as improved oral bioavailability.

Method of Use

The present invention also relates to methods for controlling the activity of Caspase enzymes. Caspase enzymes are responsible for mediating the extracellular release of cytokines. Because the control of Caspase enzyme activity directly affects a number of disease states and disease processes in humans and higher mammals, the present invention also comprises a method for controlling a number of diseases found to afflict humans and higher mammals.

The first aspect of the methods of the present invention relate to methods for mediating and controlling the extracellular release of the cytokine interleukin-1β. This cytokine activity is modulated by reversibly or irreversibly inhibiting interleukin-1β converting enzyme (Caspase-1, ICE). The method comprises the step of administering to a human or higher mammal an effective amount of a composition comprising one or more of the interleukin-1β converting enzyme inhibitors according to the present invention.

In a second aspect, as stated herein, Caspase-1 (ICE) is responsible for the cleavage of the inactive precursor of interleukin-1β (IL-1β) to release the active cytokine interleukin-1β. It has been discovered that Caspase-1 is localized to monocyte membranes and therefore inflammatory disorders caused by or otherwise exacerbated by the extracellular presence of the cytokine IL-1β can be treated by the inhibition of Caspase-1.[1,2] These inflammatory disorders include rheumatoid arthritis.

Regulation of the enzyme Caspase-1, (ICE) by way of administering a composition capable of reversibly or irreversibly inhibiting said enzymes, provides a method for controlling, modulating, mediating, or otherwise abating the inflammation of joints and other forms of synovial tissue associated with osteoarthritis and rheumatoid arthritis.

It is now recognized that in addition to degeneration of neurons associated with Huntington's disease, Caspase-3 expression is up-regulated in apoptotic hippocampal neurons from Alzheimer's disease patients.[3]

Regulation of the enzyme Caspase-3 by way of administering a composition capable of reversibly or irreversibly inhibiting said enzymes, provides a method for controlling, modulating, mediating, or otherwise abating the hippocampal neuron damage associated with Alzheimer's disease because of the over expression of one or more Caspase enzymes and the extracellular release of cytokines.

There is a growing preponderance of evidence to indicate that one or more Caspase enzymes are inappropriately activated in neurogenerative disorders and contribute to the death of neurons, in fact, activated Caspase-8 Has been identified in degenerating neurons from Huntington's disease patients.[4] Caspase-1 Has been implicated as a mediating factor in cell apoptosis. Apoptosis itself is the most common mechanism by which an organism removes unwanted or damaged cells and this ability is critically important during normal tissue development, inter alia, homeostasis, remodeling, immune response, and defense processes. Apoptosis is, therefore, implicated as contributing to several neurological disorders including Huntington's disease.[5]

Regulation of the enzyme Caspase-1, (ICE) and/or the enzyme Caspase-8, individually or collectively, by way of administering a composition capable of reversibly or irreversibly inhibiting said enzymes, provides a method for controlling, modulating, mediating, or otherwise abating the neurogenerative disorders associated with Huntington's disease.

As can be seen from the above, cell apoptosis, as well as up regulation of Caspase enzymes is a cause for not only inflammatory disease (arthritis and the like) but the degeneration of neurons and the cause of associated neurological disorders, inter alia, Parkinson's disease, Huntington's Disease and Alzheimer's disease.

The present invention therefore encompasses a method for treating separately or collectively one or more diseases, said method comprising the step of contacting a human or higher mammal with a composition comprising one or more of the Caspase inhibitors of the present invention.

As it relates to the specifically controlling the extracellular release of IL-1□ this cytokine has been implicated as a major catabolic cytokine in the degenerative cascade leading to the loss of cartilage in osteoarthritic patients[6] and to joint inflammation and the associated pain.[7] Indeed, interleukin-1β converting enzyme (ICE) is presently the only enzyme known to be responsible for the release of interleukin-1β. This release occurs when the precursor form of interleukin-1β is converted to an active form, which is then released extracellularly. It has been discovered that the presence of joint synovitis and synovial effusion in osteoarthritic patients is the direct response to the local formation of pro-inflammatory cytokines, particularly, interleukin-1β.[8]

Osteoarthritis is a degenerative articular disorder associated with progressive structural changes in cartilage, bone and synovial tissue leading to the total loss of cartilage and joint function. It has been found that interleukin-1β is elevated in chondrocytes derived from osteoarthric joints as compared to normal non-arthritic cartilage and synovium. It has been reported that inhibition of interleukin-1β using an ICE inhibitor significantly reduces cartilage protoglycan loss in the collagen-induced arthritis model.[9]

It has now been surprisingly found that administering one or more of said compounds comprises a method for controlling or modulating the loss of cartilage in osteoarthritic patients. In addition, administering said compounds comprises a method for controlling or modulating the joint inflammation and pain associated with the swelling of tissue associated with extracellular release of cytokines.

The compounds of the present invention can be administered prophylacticly. For example, in cases wherein inflammation and cartilage damage is anticipated because of ageing or other high risk, inter alia, obesity, sports activity or which inflammation and damage is anticipated as a side effect resulting from the treatment of a more severe disease state (e.g. via chemotherapy).

Because the interleukin-1β converting enzyme inhibitors of the present invention can be delivered in a manner wherein more than one site of control can be achieved, more than one disease state can be modulated at the same time. Non-limiting examples of diseases which are affected by control or inhibition of interleukin-1β converting enzyme, thereby modulating the presence of IL-1β (excessive cytokine activity), include osteoarthritis, rheumatoid arthritis, diabetes, human Immunodeficiency virus (HIV) infection.

A method for controlling osteoarthritis in humans or higher mammals, said method comprising the step of administering to a human or higher mammal and effective amount of a composition comprising one or more of the interleukin-1β converting enzyme inhibitors The following citations footnoted herein above are included herein by reference.
1. Schreiber, R. D. et al., In *Samter's Immunologic Diseases:* Frank, M. M. et al. Eds.:Little, Brown and Co,: Boston, Mass. (1994); 279–310.
2. Ghayur T.; et al, *High Throughput Screening for Novel Anti-Inflammatories.* Khan M. (Ed.) Birkhauser Verlag Publishers, Basel, Switzerland (2000) 35–48.
3. Gervais, F. et al., *Cell* (1999), 97, 395–406.
4. Sánchez, I.; et al., *Neuron* (1999), 22, 623–633.
5. Perutz, M. F.; et al., *Trends Biochem. Sci.* (1999), 24(2) 58–63
6. J-P Pelletier et al., "Cytokines and Inflammation in Cartilage Degradation": in *Osteoarthritis, Rheumatic Disease Clinics of North America,* ed. R. W. Moskowith, (Philadelphia: W. B. Sanders, 1993), 545–568.
7. F. Fernandez-Madrid et al., "Magnetic Resonace Features of Osteoarthritis of the Knee," *J. Magn. Reson. Imaging,* 12 (1994): 703–709.
8. S. A. Stimpson et al., "Exacerbation of Arthritis by IL-1 in Rat Joints Previously Injured by Peptidoglycan-Polysaccharide," *J. Immunol.* 140 (1988): 2964–2969.
9. W. B. van den Berg et al., "Amelioration of Established Murine Collagen-induced Arthritis with anti-IL-1 Treatment," *Clin. Exp. Immunol.* 95, (1994): 237–243.

Procedures

The compounds of the present invention can be evaluated for efficacy, for example, measurements of ICE inhibition constants, $K_i$, and $IC_{50}$ values can be obtained by any method chosen by the formulator. Conveniently the formulator can measure the release of, inter alia, IL-1β or cleavage of substrates by Caspace-1, Caspace-3, and Caspace-8.

THP-1 cells are human monocyte cells (mononuclear cells) which are utilized to determine in vitro cytokine inhibition. THP-1 cells, like other cell types, respond to extracellular stimulation. These stimuli include cytokines, as well as lipopolysaccharides (LPS), endotoxins, and even ultra violet light. The specific cellular response elicited by these various forms of stimuli are mediated or otherwise regulated by one or more cellular enzymes.

In the case of Caspase-1 enzyme, a signaling cascade, which includes the release of pro-inflammatory cytokines, inter alia, interleukin-1α, interleukin-1β, and TNF-α can be taken advantage of to determine the ability of chemical species to inhibit the enzyme and consequent release of said cytokines. The enzymes are themselves implicated in various disease states and processes, including cartilage degradation associated with arthritis.

One in vitro assay used to establish activity (preliminary screening) of relevant compounds of the present invention includes the following general concepts and procedures. A control sample of THP-1 cells is first stimulated to release a cytokine, in this case IL-1β, exposing the cell to LPS. The THP-1 cells which are utilized to measure suppression of cytokine release, are first incubated with the inhibitors of the present invention prior to stimulation with LPS. The supernatant from each screening sample is analyzed by standard hIL-1β ELISA protocol. The cells which remain after removal of the supernatant are treated with MTS tetrazolium to establish cell viability.

The in vitro results are reported as the $IC_{50}$, defined herein as:

$$IC_{50} = \frac{[I]}{\left[\frac{V_o}{V_i}\right] - 1}$$

wherein $V_i$ is the initial rate of substrate cleaved in the presence of the test compound at concentration [I], and $V_o$ is the rate of substrate cleavage in the control sample.

Non-limiting examples of suitable assays include:
i) UV-visible substrate enzyme assay as described by L. Al Reiter, *Int. J. Peptide Protein Res.*, 43, 87–96 (1994).
ii) Fluorescent substrate enzyme assay as described by Thornberry et al., *Nature*, 356, 768–774 (1992) and Thornberry et al., *Biochemistry*, 33, 393–3940 (1994).
iii) PBMC Cell assay as described in U.S. Pat. No. 6,204,261 B1 Batchelor et al., issued Mar. 20, 2001.

All documents cited in the Detailed Description of the Invention are, are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A compound or its enantiomeric or diasteriomeric form or a pharmaceutically acceptable salt thereof, said compound having the formula:

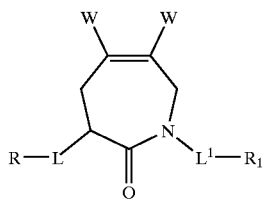

wherein each W is hydrogen of a unit having the formula $—(L^2)_j—R^2$, the index j is 0 or 1;
wherein R is a ring chosen from:
i) substituted or unsubstituted $C_3-C_{10}$ non-aromatic carbocyclic;
ii) substituted or unsubstituted $C_6-C_{10}$ aryl;
iii) substituted or unsubstituted $C_1-C_{10}$ heterocyclic; and
iv) substituted or unsubstituted $C_1-C_{10}$ heteroaryl;
$R^1$ is a cysteine trap;
each $R^3$ is independently selected from the group consisting of:
i) hydrogen;
ii) a hydrocarbyl unit having the formula: $—[C(R^3)_2]_p(CH=CH)_qR^3$;
iii) $—C(=Z)R^3$;
iv) $—C(=Z)AR^3$;
v) $—C(=Z)[C(R^3)_2]_p(CH=CH)_qR^3$;
vi) $—C(=Z)N(R^3)_2$;
vii) $—C(=Z)NR^3N(R^3)_2$;

viii) $—CN$;
xix) $—CF_3$;
x) $—N(R^3)_2$;
xi) $—NR^3CN$;
xii) $—NR^3C(=Z)R^3$;
xiii) $—NR^3C(=Z)N(R^3)_2$;
xiv) $—NHN(R^3)_2$;
xv) $—NHOR^3$;
xvi) $—NO^2$;
xvii) $—OR^3$;
xviii) $—OCF_3$;
xix) $—F$, $—Cl$, $—Br$, or $—I$;
—xx) $—SO_3M$;
—xxi) $—OSO_3M$;
xxii) $—SO_2N(R^3)_2$;
xxiii) $—SO_2R^3$;
xxiv) $—P(O)(OR^3)R^3$;
xxv) $—P(O)(OR^3)_2$;
xxvi) and mixtures thereof;

each $R^3$ is independently hydrogen, substituted or unsubstituted $C_1-C_{20}$ linear, branched, or cyclic alkyl, substituted or unsubstituted $C_6-C_{20}$ aryl, $C_1-C_{20}$ substituted or unsubstituted heterocyclic, $C_1-C_{20}$ substituted or unsubstituted heteroaryl; Z is O, S, or $NR^3$; M is hydrogen, or a salt forming cation; the index p is from 0 to 12; the index q is from 0 to 12;

L, $L^1$, and $L^2$ are each independently a linking group having the formula:

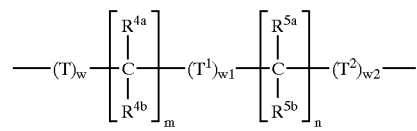

T, $T^1$, and $T^2$ are each independently selected from the group consisting of:
i) $—NR^6—$;
ii) $—O—$;
iii) $—S(O)_2—$;
iv) $—NR^6S(O)_2—$; and
v) $—S(O)_2NR^6—$;

$R^6$ is hydrogen, substituted or unsubstituted $C_1-C_{10}$ linear, branched, or cyclic alkyl, $C_6-C_{10}$ aryl, and $C_7-C_{12}$ alkylenearyl; the indices w, $w^1$, and $w^2$ are each independently 0 or 1;

$R^{4a}$, $R^{4b}$, $R^{5a}$, and $R^{5b}$ are each independently:
i) hydrogen;
ii) $C_1-C_4$ linear, branched, and cyclic alkyl;
iii) $R^{4a}$ and $R^{4b}$ or $R^{5a}$, and $R^{5b}$ can be taken together to form a carbonyl unit; and
iv) two $R^{3a}$ or two $R^{3b}$ units from adjacent carbon atoms or two $R^{4a}$ or two $R^{4b}$ units from adjacent carbon atoms can be taken together to form a double bond;
the index m is from 0 to 5; the index n is from 0 to 5.

2. A compound according to claim 1 comprising a scaffold having the formula:

i)

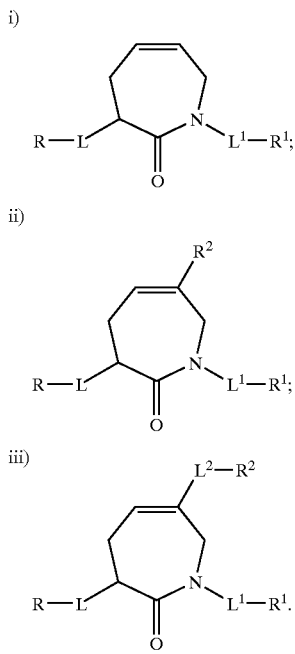

ii)

iii)

3. A compound according to claim 1 wherein $R^1$ is a reversible cysteine trap having the formula:

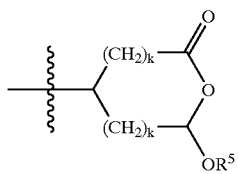

wherein $R^5$ is hydrogen; $C_1$–$C_4$ alkyl; substituted or unsubstituted $C_6$–$C_{10}$ aryl; and substituted or unsubstituted ($C_7$–$c_{20}$) alkylenearyl; each index k is independently 0, 1, or 2.

4. A compound according to claim 3 wherein $R^1$ is a reversible cysteine trap having the formula:

a)

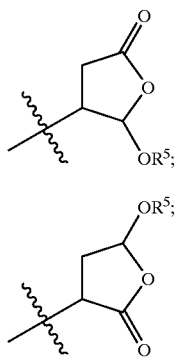

b)

-continued c)

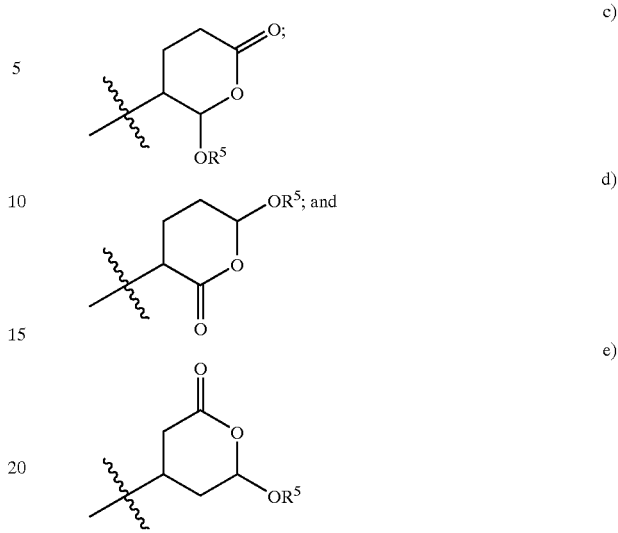

d)

e)

wherein $R^5$ is hydrogen, $C_1$–$C_4$ alkyl, or benzyl.

5. A compound according to claim 1 wherein $R^1$ is a reversible cysteine trap having the formula:

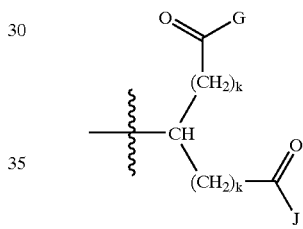

wherein G is —OH or a labile unit and J is a unit selected from the group:
  i) hydrogen;
  ii) substituted or unsubstituted $C_6$–$C_{10}$ aryl;
  iii) substituted or unsubstituted $C_7$–$C_{20}$ alkylenearyl;
  iv) substituted or unsubstituted $C_1$–$C_{10}$ heteroaryl;
  v) —$CH_2N(R^{21})_2$;
  vi) —$C(O)R^{21}$;
  vii) —$C(O)N(R^{21})_2$; and
  viii) —$C(O)OR^{21}$;
  $R^{21}$ is hydrogen, substituted or unsubstituted $C_6$–$C_{10}$ aryl, substituted or unsubstituted $C_6$–$C_{10}$ alkylenearyl, and substituted or unsubstituted $C_1$–$C_{10}$ heteroaryl; each index k is independently 0, 1, or 2.

6. A compound according to claim 5 wherein $R^1$ has the formula:

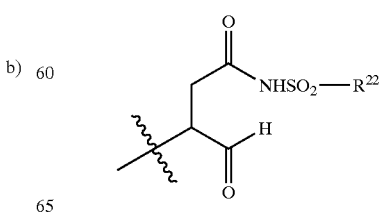

wherein $R^{22}$ is $C_1$–$C_4$ alkyl.

7. A compound according to claim 5 wherein $R^1$ has the formula:

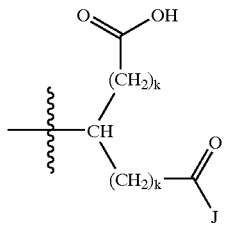

wherein J is —$(CH)_u R^{23}$; $R^{23}$ is a substituted or unsubstituted $C_6$–$C_{10}$ aryl; the index u is from 0 to 10.

8. A compound according to claim 7 wherein J is selected from the group consisting of benzyl, 2-phenylethyl, 3-phenylpropyl, 4-phenylbutyl, and 5-phenylpentyl.

9. A compound according to claim 5 wherein J is —$(CH_2)N(R^{21})_2$ and one $R^{21}$ is hydrogen and the other is an alkylenearyl unit selected from the group consisting of benzyl, 2-phenylethyl, 3-phenylpropyl, 4-phenylbutyl, and 5-phenylpentyl.

10. A compound according to claim 5 wherein J is an alkylenearyl unit selected from the group consisting of benzyl, 2-phenylethyl, 3-phenylpropyl, 4-phenylbutyl, and 5-phenylpentyl.

11. A compound according to claim 1 wherein $R^1$ is an α,α-difluoro ketone reversible cysteine trap having the formula:

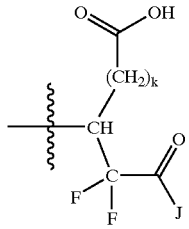

wherein J is a unit selected from the group:
i) hydrogen;
ii) substituted or unsubstituted $C_6$–$C_{10}$ aryl;
iii) substituted or unsubstituted $C_7$–$C_{20}$ alkylenearyl;
iv) substituted or unsubstituted $C_1$–$C_{10}$ heteroaryl;
v) —$CH_2N(R^{21})_2$;
vi) —$C(O)R^{21}$;
vii) —$C(O)N(R^{21})_2$; and
viii) —$C(O)OR^{21}$;

$R^{21}$ is hydrogen, substituted or unsubstituted $C_6$–$C_{10}$ aryl, substituted or unsubstituted $C_6$–$C_{10}$ alkylenearyl, and substituted or unsubstituted $C_1$–$C_{10}$ heteroaryl; each index k is independently 0, 1, or 2.

12. A compound according to claim 1 wherein $R^1$ is an irreversible cysteine trap having the formula:

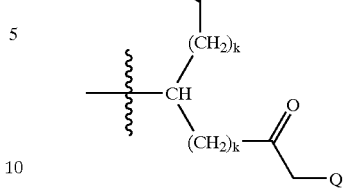

wherein Q is a leaving group selected from:
i) substituted or unsubstituted $C_2$–$C_{10}$ heterocyclic or $C_1$–$C_{10}$ heteroaryl;
ii) —$OC(O)R^{11}$;
iii) —$NHSO_2R^{12}$;
iv) —$ONR^{13}C(O)R^{13}$;
v) halogen;
vi) —$NHC(O)OR^{14}$;
vii) —$NHC(O)NHR^{15}$;
ix) —$OR^{16}$;
x) —$SR^{17}$;
xi) —$SSR^{18}$;
xii) —$SSO_3R^{19}$; and
xiii) —$OP(O)(R^{20})_2$;

wherein $R^{11}$ is $C_6$–$C_{10}$ aryl, $C_7$–$C_{20}$ alkylenearyl, —$NHR^{24}$; $R^{24}$ is $C_1$–$C_4$ alkyl; $R^{12}$ is $C_1$–$C_{12}$ linear, branched, or cyclic alkyl; $R^{13}$ is hydrogen, $C_1$–$C_4$ alkyl, substituted or unsubstituted $C_6$–$C_{10}$ aryl, substituted or unsubstituted $C_7$–$C_{20}$ alkylenearyl, or two $R^{13}$ units can be taken together to form a fused or no-fused ring having from 3 to 12 atoms; $R^{14}$ is substituted or unsubstituted $C_6$–$C_{10}$ aryl or substituted or unsubstituted $C_7$–$C_{20}$ alkylenearyl; $R^{15}$ is $C_1$–$C_4$ alkyl, substituted or unsubstituted $C_6$–$C_{10}$ aryl, and substituted or unsubstituted $C_7$–$C_{20}$ alkylenearyl; $R^{16}$ is $C_1$–$C_4$ alkyl; $R^{17}$ and $R^{18}$ are substituted or unsubstituted $C_6$–$C_{10}$ aryl, and substituted or unsubstituted $C_7$–$C_{20}$ alkylenearyl; $R^{19}$ is hydrogen, $C_1$–$C_4$ alkyl, substituted or unsubstituted $C_6$–$C_{10}$ aryl, and substituted or unsubstituted $C_7$–$C_{20}$ alkylenearyl; $R^{20}$ is substituted or unsubstituted $C_6$–$C_{10}$ aryl, and substituted or unsubstituted $C_7$–$C_{20}$ alkylenearyl; each index k is independently 0, 1, or 2.

13. A compound according to claim 12 wherein $R^1$ is a cysteine trap having the formula:

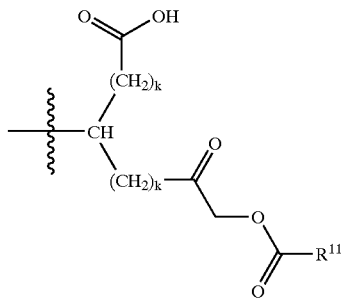

wherein $R^{11}$ is a substituted $C_6$–$C_{10}$ aryl unit.

14. A compound according to claim 13 wherein $R^{11}$ is 2,6-dimethylphenyl or 2,6-dichlorophenyl.

15. A compound according to claim 1 wherein L, $L^1$, and $L^2$ are each independently selected from the group consisting of:
i) —C(O)NH—;
ii) —NHC(O)—;
iii) —NHC(O)NH—;
iv) —C(O)C(O)—;
v) —C(O)—;
vi) —C(O)O—;
vii) —OC(O)—;
viii) —NH—;
ix) —NHS(O)$_2$—;
x) —S(O)$_2$NH—;
xi) —S(O)$_2$—;
xii) and mixtures thereof.

16. A compound according to claim 1 wherein R is a substituted or unsubstituted $C_6$–$C_{10}$ aryl ring selected from the group consisting of phenyl, 2-fluorophenyl, 3-fluorophenyl, 4-fluorophenyl, 3-fluoro-4-methylphenyl, 3-fluoro-4-methoxyphenyl, 3-chloro-2-methylphenyl, 3-chloro-6-methylphenyl, 3-chloro-4-methoxyphenyl, 3-chloro-4-hydroxyphenyl, 3,5-difluorophenyl, 2,6-dichlorophenyl, 2-chlorophenyl, 3-chlorophenyl, 4-chlorophenyl, 3,4-dichlorophenyl, 3,5-dichlorophenyl, 3-chloro-4-fluorophenyl, 2-bromophenyl, 3-bromophenyl, and 4-bromophenyl.

17. A compound according to claim 1 wherein R is a substituted or unsubstituted $C_6$–$C_{10}$ aryl ring selected from the group consisting of 2-methylphenyl, 3-methylphenyl, 4-methylphenyl, 3,5-dimethylphenyl, 2-ethylphenyl, 3-ethylphenyl, 4-ethylphenyl, 3-ethyl-4-methylphenyl 3-propylphenyl, and 3-butylphenyl.

18. A compound according to claim 1 wherein R is a substituted or unsubstituted $C_6$–$C_{10}$ aryl ring selected from the group consisting of 2-methoxyphenyl, 3-methoxyphenyl, 4-methoxyphenyl, 2-ethoxyphenyl, 3-ethoxyphenyl, 4-ethoxyphenyl, 4-propoxyphenyl, 4-butoxyphenyl, and 3,4,5-trimethoxy-phenyl.

19. A compound according to claim 1 wherein R is a substituted or unsubstituted $C_6$–$C_{10}$ aryl ring selected from the group consisting of 3-aminonaphth-2-yl, 4-dimethylaminonaphth-1-yl, 2-aminophenyl, 3-aminophenyl, 4-aminophenyl, 3,4-dimethylaminophenyl, 4-amino-3-chlorophenyl, 4-amino-3,5-dichlorophenyl, 4-dimethylaminophenyl, 2-acetylaminophenyl, 3-acetylaminophenyl, 4-acetylaminophenyl, 4-isobutyrylaminophenyl, 4-propionylaminophenyl, 4-butrylaminophenyl, 4-phenylacetylaminophenyl, 3,4-diacetylaminophenyl, 4-(N-acetyl-N-methylamino)-phenyl, and 4-benzoylaminophenyl.

20. A compound according to claim 1 wherein R is a substituted or unsubstituted $C_6$–$C_{10}$ aryl ring selected from the group consisting of 2-trifluoromethylphenyl, 3-trifluoromethylphenyl, 4-trifluoromethylphenyl, 4-hydroxymethyl-phenyl, naphth-1-yl, naphth-2-yl, 4-biphenyl, 4-phenoxyphenyl, 4-(3-methyl-ureido)-phenyl, 4-sulfamoylphenyl, 3-acetylphenyl, 4-acetylphenyl, 3-hydroxyphenyl, 4-hydroxyphenyl, 4-benzyloxyphenyl, and 4-methanesulfonyl-phenyl.

21. A compound according to claim 1 wherein R is a substituted or unsubstituted $C_3$–$C_{10}$ non-aromatic carbocyclic ring selected from the group consisting of cyclopropyl, cyclobutyl, cyclohexyl, cyclopentyl, cyclohexenyl, and cyclopentanyl.

22. A compound according to claim 1 wherein R is a substituted or unsubstituted $C_1$–$C_{10}$ heteroaryl unit selected from the group consisting of pyridin-2-yl, pyridin-3-yl, pyridin-4-yl, 3-chloropyridin-2-yl, 4-chloropyridin-2-yl, 5-chloropyridin-2-yl, 6-chloropyridin-2-yl, 3-methylpyridin-3-yl, 4-methylpyridin-3-yl, 5-methylpyridin-3-yl, vinyl pyridin-4-yl, and vinyl pyridin-3-yl.

23. A compound according to claim 1 wherein R is a substituted or unsubstituted $C_1$–$C_{10}$ heteroaryl unit selected from the group consisting of thiophen-3-yl, thiophen-2-yl, pyrimidin-2-yl, pyrimidin-4-yl, pyrimidin-5-yl, 2-isobutoxy-pyrimidin-4-yl, 2-isobutylaminopyrimidin-4-yl, 2-phenoxypyrimidin-4-yl, 2-ethyl-5-methyl-2H-pyrazol-3-yl, 2,4-dimethyl-thiazol-5-yl, 5-methyl-isoxazol-3-yl, 1H-imidazol-2-yl, [1,2,3]thiadiazol-5-yl, furan-2-yl, furan-3-yl, 4,5-dimethyl-2-furanyl, 5-bromo-2-furanyl, and 2-(phenylamino)pyrimidin-4-yl.

24. A compound according to claim 1 wherein R is a substituted or unsubstituted $C_1$–$C_{10}$ heterocyclic ring selected from the group consisting of quinolin-2-yl, quinolin-3-yl, quinolin-4-yl, quinolin-5-yl, quinolin-8-yl, isoquinolin-1-yl, isoquinolin-3-yl, 1,2,3,4-tetrahydro-quinolin-2-yl, 1,2,3,4-tetrahydro-quinolin-3-yl, benzofuran-2-yl, benzofuran-3-yl, benzofuran-5-yl, 1H-indol-5-yl, benzo[b]thiophen-5-yl, benzo[b]thiophen-3-yl, benzo[b]thiophen-2-yl, 3H-benzotriazol-5-yl, 1-methyl-1H-indol-2-yl, 3H-benzimidazol-5-yl, 4-methoxy-quinolin-2-yl, and thieno[2,3-b]thiophen-2-yl.

25. A compound according to claim 1 wherein R is a substituted or unsubstituted $C_1$–$C_{10}$ heterocyclic ring selected from the group consisting of pyrrolidin-1-yl, piperidin-1-yl, piperidin-4-yl, and piperazin-1-yl.

26. A compound according to claim 2 having the formula:

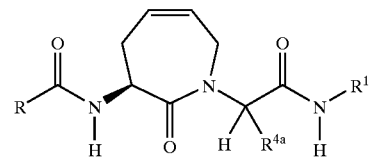

wherein $R^{4a}$ is hydrogen.

27. A compound selected from the group consisting of:
Isoquinoline-1-carboxylic acid {1-[(2-hydroxy-5-oxo-tetra-hydrofuran-3-ylcarbamoyl)methyl]-2-oxo-2,3,4,7-tetrahydro-1H-azepin-3-yl} amide;
Isoquinoline-1-carboxylic acid {1-[(2-ethoxy-5-oxo-tetra-hydrofuran-3-ylcarbamoyl)methyl]-2-oxo-2,3,4,7-tetrahydro-1H-azepin-3-yl} amide;
Naphthalene-2-carboxylic acid {1-[(2-hydroxy-5-oxo-tetra-hydrofuran-3-ylcarbamoyl)methyl]-2-oxo-2,3,4,7-tetrahydro-1H-azepin-3-yl} amide;
Naphthalene-2-carboxylic acid {1-[(2-ethoxy-5-oxo-tetra-hydrofuran-3-ylcarbamoyl)methyl]-2-oxo-2,3,4,7-tetrahydro-1H-azepin-3-yl} amide;
Benzothiaphene-2-carboxylic acid {1-[(2-hydroxy-5-oxo-tetrahydrofuran-3-ylcarbamoyl)methyl]-2-oxo-2,3,4,7-tetrahydro-1H-azepin-3-yl} amide;
Benzothiaphene-2-carboxylic acid {1-[(2-ethoxy-5-oxo-tetrahydrofuran-3-ylcarbamoyl)methyl]-2-oxo-2,3,4,7-tetrahydro-1H-azepin-3-yl} amide;
N-{1-[(2-Hydroxy-5-oxo-tetrahydrofuran-3-ylcarbamoyl)methyl]-2-oxo-2,3,4,7-tetrahydro-1H-azepine-3-yl-benzamide;
N-{1-[(2-Ethoxy-5-oxo-tetrahydrofuran-3-ylcarbamoyl)methyl]-2-oxo-2,3,4,7-tetrahydro-1H-azepine-3-yl-benzamide;
3-Fluoro-N-{1-[(2-hydroxy-5-oxo-tetrahydrofuran-3-ylcarbamoyl)methyl]-2-oxo-2,3,4,7-tetrahydro-1H-azepine-3-yl-benzamide;

3-Fluoro-N-{1-[(2-ethoxy-5-oxo-tetrahydrofuran-3-yl-carbamoyl)methyl]-2-oxo-2,3,4,7-tetrahydro-1H-azepine-3-yl-benzamide;
3-Trifluoromethyl-N-{1-[(2-hydroxy-5-oxo-tetrahydrofuran-3-ylcarbamoyl)methyl]-2-oxo-2,3,4,7-tetrahydro-1H-azepine-3-yl-benzamide;
3-Trifluoromethyl-N-{1-[(2-ethoxy-5-oxo-tetrahydrofuran-3-ylcarbamoyl)methyl]-2-oxo-2,3,4,7-tetrahydro-1H-azepine-3-yl-benzamide;
3-Methoxy-N-{1-[(2-hydroxy-5-oxo-tetrahydrofuran-3-ylcarbamoyl)methyl]-2-oxo-2,3,4,7-tetrahydro-1H-azepine-3-yl-benzamide;
3-Methoxy-N-{1-[(2-ethoxy-5-oxo-tetrahydrofuran-3-yl-carbamoyl)methyl]-2-oxo-2,3,4,7-tetrahydro-1H-azepine-3-yl-benzamide;
3-Acetyl-N-{1-[(2-hydroxy-5-oxo-tetrahydrofuran-3-yl-carbamoyl)methyl]-2-oxo-2,3,4,7-tetrahydro-1H-azepine-3-yl-benzamide;
3-Acetyl-N-{1-[(2-ethoxy-5-oxo-tetrahydrofuran-3-yl-carbamoyl)methyl]-2-oxo-2,3,4,7-tetrahydro-1H-azepine-3-yl-benzamide;
3-Benzoyl-N-{1-[(2-hydroxy-5-oxo-tetrahydrofuran-3-ylcarbamoyl)methyl]-2-oxo-2,3,4,7-tetrahydro-1H-azepine-3-yl-benzamide; and
3-Benzoyl-N-{1-[(2-ethoxy-5-oxo-tetrahydrofuran-3-yl-carbamoyl)methyl]-2-oxo-2,3,4,7-tetrahydro-1H-azepine-3-yl-benzamide.

28. A compound according to claim 2 having the formula:

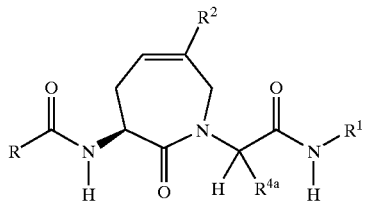

wherein $R^{4a}$ is hydrogen.

29. A compound according to claim 28 wherein $R^2$ is $C_1-C_4$ linear branched or cyclic alkyl.

30. A compound according to claim 2 having the formula:

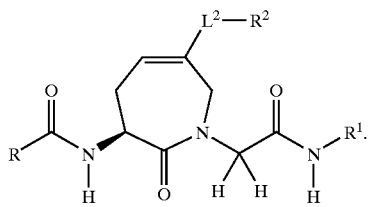

31. A compound according to claim 30 wherein —$L^2R^2$ is selected from the group consisting of benzyl, —$CH_2OH$, —$CH_2SH$, —$CH_2SC_6H_5$ and —$CH_2OC_6H_5$.

32. A compound according to claim 30 wherein —$L^2R^2$ is selected from the group consisting of phenyl, 4-isopropylphenyl, 4-pentylphenyl, 2-fluorophenyl, 3-fluorophenyl, 4-fluorophenyl, 2-methylphenyl, 3-methylphenyl, 4-methylphenyl, 2-methoxyphenyl, 3-methoxyphenyl, and 4-methoxyphenyl.

33. A compound according to claim 30 wherein —$L^2R^2$ is selected from the group consisting of selected from the group consisting of phenyl, 4-isopropylphenyl, 4-pentylphenyl, 2-fluorophenyl, 3-fluorophenyl, 4-fluorophenyl, 2-methylphenyl, 3-methylphenyl, 4-methylphenyl, 2-methoxyphenyl, 3-methoxyphenyl, and 4-methoxyphenyl.

34. A compound according to claim 30 wherein —$L^2R^2$ is selected from the group consisting of —$CH_2NHCOC_6H_5$, —$CH_2NHCO[4-CH(CH_3)_2C_6H_4]$, —$CH_2NHCO(4-n-pentylC_6H_4)$, —$CH_2NHCO(2-FC_6H_4)$, —$CH_2NHCO(3-FC_6H_4)$, —$CH_2NHCO(4-FC_6H_4)$, —$CH_2NHCO(2-CH_3C_6H_4)$, —$CH_2NHCO(3-CH_3C_6H_4)$, —$CH_2NHCO(4-CH_3C_6H_4)$, —$CH_2NHCO(2-OCH_3C_6H_4)$, —$CH_2NHCO(3-OCH_3C_6H_4)$, and —$CH_2NHCO(4-OCH_3C_6H_4)$.

35. A compound according to claim 30 wherein —$L^2R^2$ is selected from the group consisting of —$CH_2NHSO_2C_6H_5$—$CH_2NHSO_2(4-n-pentylC_6H_4)$, —$CH_2NHSO_2(2-FC_6H_4)$, —$CH_2NHSO_2(3-FC_6H_4)$, —$CH_2NHSO_2(4-FC_6H_4)$, —$CH_2NHSO_2(2-CH_3C_6H_4)$, —$CH_2NHSO_2(3-CH_3C_6H_4)$, —$CH_2NHSO_2(4-CH_3C_6H_4)$, —$CH_2NHSO_2(2-OCH_3C_6H_4)$, —$CH_2NHSO_2(3-OCH_3C_6H_4)$, and —$CH_2NHSO_2(4-OCH_3C_6H_4)$.

36. A compound selected from the group consisting of:
Isoquinoline-1-carboxylic acid {6-hydroxymethyl-1-[(2-ethoxy-5-oxo-tetrahydro-furan-3-ylcarbamoyl)-methyl]-2-oxo-2,3,4,7-tetrahydro-1H-azepin-3-yl}-amide;
Isoquinoline-1-carboxylic acid {6-ethoxymethyl-1-[(2-ethoxy-5-oxo-tetrahydro-furan-3-ylcarbamoyl)-methyl]-2-oxo-2,3,4,7-tetrahydro-1H-azepin-3-yl}-amide;
Naphthalene-2-carboxylic acid {6-hydroxymethyl-1-[(2-ethoxy-5-oxo-tetrahydro-furan-3-ylcarbamoyl)-methyl]-2-oxo-2,3,4,7-tetrahydro-1H-azepin-3-yl}-amide;
Naphthalene-2-carboxylic acid {6-ethoxymethyl-1-[(2-ethoxy-5-oxo-tetrahydro-furan-3-ylcarbamoyl)-methyl]-2-oxo-2,3,4,7-tetrahydro-1H-azepin-3-yl}-amide;
Benzothiphene-2-carboxylic acid {6-hydroxymethyl-1-[(2-ethoxy-5-oxo-tetrahydro-furan-3-ylcarbamoyl)-methyl]-2-oxo-2,3,4,7-tetrahydro-1H-azepin-3-yl}-amide;
Benzothiaphene-2-carboxylic acid {6-ethoxymethyl-1-[(2-ethoxy-5-oxo-tetrahydro-furan-3-ylcarbamoyl)-methyl]-2-oxo-2,3,4,7-tetrahydro-1H-azepin-3-yl}-amide;
N-{6-hydroxymethyl-1-[(2-ethoxy-5-oxo-tetrahydro-furan-3-ylcarbamoyl)-methyl]-2-oxo-2,3,4,7-tetrahydro-1H-azepin-3-yl}-benzamide; and
N-{6-ethoxymethyl-1-[(2-ethoxy-5-oxo-tetrahydro-furan-3-ylcarbamoyl)-methyl]-2-oxo-2,3,4,7-tetrahydro-1H-azepin-3-yl}-benzamide.

37. A compound selected from the group consisting of:
Isoquinoline-1-carboxylic acid {6-(benzylamino-methyl)-1-[(2-hydroxy-5-oxo-tetrahydro-furan-3-ylcarbamoyl)-methyl]-2-oxo-2,3,4,7-tetrahydro-1H-azepin-3-yl}-amide;
Isoquinoline-1-carboxylic acid {6-(benzylamino-methyl)-1-[(2-ethoxy-5-oxo-tetrahydro-furan-3-ylcarbamoyl)-methyl]-2-oxo-2,3,4,7-tetrahydro-1H-azepin-3-yl}-amide;
Isoquinoline-1-carboxylic acid {1-[(2-hydroxy-5-oxo-tetrahydro-furan-3-ylcarbamoyl)-methyl]-2-oxo-6-piperidin-1-ylmethyl-2,3,4,7-tetrahydro-1H-azepin-3-yl}-amide;
Isoquinoline-1-carboxylic acid {1-[(2-hydroxy-5-oxo-tetrahydro-furan-3-ylcarbamoyl)-methyl]-2-oxo-6-phenylaminomethyl-2,3,4,6-tetrahydro-1H-azepin-3-yl}-amide;

Isoquinoline-1-carboxylic acid {6-allylaminomethyl-1-[(2-hydroxy-5-oxo-tetrahydro-furan-3-ylcarbamoyl)-methyl]-2-oxo-2,3,4,7-tetrahydro-1H-azepin-3-yl}-amide; and Isoquinoline-1-carboxylic acid {1-[{2-hydroxy-5-oxo-tetrahydro-furan-3-ylcarbamoyl)-methyl]-6-morpholin-4-ylmethyl-2-oxo-2,3,4,7-tetrahydro-1H-azepin-3-yl}-amide.

38. A compound selected from the group consisting of:

Isoquinoline-1-carboxylic acid {6-(benzoylamino-methyl)-1-[(2-hydroxy-5-oxo-tetrahydro-furan-3-ylcarbamoyl)-methyl]-2-oxo-2,3,4,7,-tetrahydro-1H-azepin-3-yl}-amide;

Isoquinoline-1-carboxylic acid {6-(benzoylamino-methyl)-1-[(2-ethoxy-5-oxo-tetrahydro-furan-3-ylcarbamoyl)-methyl]-2-oxo-2,3,4,7,-tetrahydro-1H-azepin-3-yl}-amide;

Isoquinoline-1-carboxylic acid [(2-hydroxy-5-oxo-tetrahydro-furan-3-ylcarbamoyl)-methyl]-6-(methanesulfonylamino-methyl)-2-oxo-2,3,4,7-tetrahydro-1H-azepin-3-yl]-amide;

Isoquinoline-1-carboxylic acid {6-(benzenesulfonylamino-methyl)-1-[(2-hydroxy-5-oxo-tretrahydro-furan-3-ylcarbamoyl)-methyl]-2-oxo-2,3,4,7-tetrahydro-1H-azepin-3-yl}-amide;

Naphthalene-2-carboxylic acid {1-[(2-hydroxy-5-oxo-tetrahydro-furan-3-ylcarbamoyl)-methyl]-6-[(3-methoxy-benzylamino)-methyl]-2-oxo-2,3,4,7-tetrahydro-1H-azepin-3-yl}-amide;

Naphthalene-2-carboxylic acid {1-[(2-hydroxy-5-oxo-tetrahydro-furan-3-ylcarbamoyl)-methyl]-6-[(2-methoxy-benzylamino)-methyl]-2-oxo-2,3,4,7-tetrahydro-1H-azepin-3-yl}-amide;

Naphthalene-2-carboxylic acid {1-[(2-hydroxy-5-oxo-tetrahydro-furan-3-ylcarbamoyl)-methyl]-6-[(4-methoxy-benzylamino)-methyl]-2-oxo-2,3,4,7-tetrahydro-1H-azepin-3-yl}-amide;

Naphthalene-2-carboxylic acid {6-[(4-tert-butyl-benzylamino)-methyl]-1-[(2-hydroxy-5-oxo-tetrahydro-furan-3-ylcarbamoyl)-methyl]-2-oxo-2,3,4,7-tetrahdyro-1H-azepin-3-yl}-amide;

Naphthalene-2-carboxylic acid {1-[(2-hydroxy-5-oxo-tetrahydro-furan-3-ylcarbamoyl)-methyl]-6-[(2-methyl-benzylamino)-methyl]-2-oxo-2,3,4,7-tetrahydro-1H-azepin-3-yl}-amide;

Naphthalene-2-carboxylic acid {1-[(2-hydroxy-5-oxo-tetrahydro-furan-3-ylcarbamoyl)-methyl]-6-[(3-methyl-benzylamino)-methyl]-2-oxo-2,3,4,7-tetrahydro-1H-azepin-3-yl}-amide;

Naphthalene-2-carboxylic acid {1-[(2-hydroxy-5-oxo-tetrahydro-furan-3-ylcarbamoyl)-methyl]-6-[(4-methyl-benzylamino)-methyl]-2-oxo-2,3,4,7-tetrahydro-1H-azepin-3-yl}-amide;

Naphthalene-2-carboxylic acid {1-[(2-hydroxy-5-oxo-tetrahydro-furan-3-ylcarbamoyl)-methyl]-6-[(4-methanesulfonyl-benzylamino)-methyl]-2-oxo-2,3,4,7-tetrahydro-1H-azepin-3-yl}-amide;

Naphthalene-2-carboxylic acid {1-[(2-hydroxy-5-oxo-tetrahydro-furan-3-ylcarbamoyl)-methyl]-2-oxo-6-[(4-[1,2,3]thiadiazol-4-yl-benzylamino)-methyl]-2,3,4,7-tetrahydro-1H-azepin-3-yl}-amide;

Naphthalene-2-carboxylic acid {1-[(2-hydroxy-5-oxo-tetrahydro-furan-3-ylcarbamoyl)-methyl]-6-[(4-isopropyl-benzylamino)-methyl]-2-oxo-2,3,4,7-tetrahydro-1H-azepin-3-yl}-amide;

Naphthalene-2-carboxylic acid {1-[(2-hydroxy-5-oxo-tetrahydro-furan-3-ylcarbamoyl)-methyl]-2-oxo-6-[(4-pentyl-benzylamino)-methyl]-2,3,4,7-tetrahydro-1H-azepin-3-yl}-amide;

Naphthalene-2-carboxylic acid {6-(benzoylamino-methyl)-1-[(2-hydroxy-5-oxo-tetrahydro-furan-3-ylcarbamoyl)-methyl]-2-oxo-2,3,4,7-tetrahydro-1H-azepin-3-yl}-amide;

Naphthalene-2-carboxylic acid {6-(benzenesulfonylamino-methyl)-1-[(2-hydroxy-5-oxo-tetrahydro-furan-3-ylcarbamoyl)-methyl]-2-oxo-2,3,4,7-tetrahydro-1H-azepin-3-yl}-amide;

Naphthalene-2-carboxylic acid {6-[(2-fluoro-benzoylamino)-methyl]-1-[3-(2-hydroxy-5-oxo-tetrahydro-furan-3-yl)-2-oxo-propyl]-2-oxo-2,3,4,7-tetrahydro-1H-azepin-3-yl}-amide;

Naphthalene-2-carboxylic acid {6-[(3-fluoro-benzoylamino)-methyl]-1-[3-(2-hydroxy-5-oxo-tetrahydro-furan-3-yl)-2-oxo-propyl]-2-oxo-2,3,4,7-tetrahydro-1H-azepin-3-yl}-amide;

Naphthalene-2-carboxylic acid {6-[(4-fluoro-benzoylamino)-methyl]-1-[3-(2-hydroxy-5-oxo-tetrahydro-furan-3-yl)-2-oxo-propyl]-2-oxo-2,3,4,7-tetrahydro-1H-azepin-3-yl}-amide;

Naphthalene-2-carboxylic acid {1-[(2-hydroxy-5-oxo-tetrahydro-furan-3-ylcarbamoyl)-methyl]-6-[(2-methoxy-benzoylamino)-methyl]-2-oxo-2,3,4,7-tetrahydro-1H-azepin-3-yl}-amide;

Naphthalene-2-carboxylic acid {1-[(2-hydroxy-5-oxo-tetrahydro-furan-3-ylcarbamoyl)-methyl]-6-[(3-methoxy-benzoylamino)-methyl]-2-oxo-2,3,4,7-tetrahydro-1H-azepin-3-yl}-amide;

Naphthalene-2-carboxylic acid {1-[(2-hydroxy-5-oxo-tetrahydro-furan-3-ylcarbamoyl)-methyl]-6-[(4-methoxy-benzoylamino)-methyl]-2-oxo-2,3,4,7-tetrahydro-1H-azepin-3-yl}-amide;

Naphthalene-2-carboxylic acid {1-[(2-hydroxy-5-oxo-tetrahydro-furan-3-ylcarbamoyl)-methyl]-6-[(4-methyoxy-benzenesulfonylamino)-methyl}-2-oxo-2,3,4,7-tetrahydro-1H-azepin-3-yl}-amide;

Naphthalene-2-carboxylic acid {1-[(2-hydroxy-5-oxo-tetrahydro-furan-3-ylcarbamoyl)-methyl]-2-oxo-6-[(toluene-3-sulfonylamino)-methyl]-2,3,4,7-tetrahydro-1H-azepin-3-yl}-amide;

Naphthalene-2-carboxylic acid {1-[(2-hydroxy-5-oxo-tetrahydro-furan-3-ylcarbamoyl)-methyl]-2-oxo-6-[(toluene-2-sulfonylamino)-methyl]-2,3,4,7-tetrahydro-1H-azepin-3-yl}-amide;

Naphthalene-2-carboxylic acid {1-[(2-hydroxy-5-oxo-tetrahydro-furan-3-ylcarbamoyl)-methyl]-2-oxo-6-[(toluene-4-sulfonylamino)-methyl]-2,3,4,7-tetrahydro-1H-azepin-3-yl}-amide;

Naphthalene-2-carboxylic acid {1-[(2-hydroxy-5-oxo-tetrahydro-furan-3-ylcarbamoyl)-methyl]-6-[(3-methyoxy-benzenesulfonylamino)-methyl}-2-oxo-2,3,4,7-tetrahydro-1H-azepin-3-yl}-amide;

Naphthalene-2-carboxylic acid {6-benzylsulfanylmethyl-1-[(2-hydroxy-5-oxo-tetrahydro-furan-3-ylcarbamoyl)-methyl]-2-oxo-2,3,4,7-tetrahydro-1H-azepin-3-yl}-amide; and Naphthalene-2-carboxylic acid {1-[(2-hydroxy-5-oxo-tetrahydro-furan-3-ylcarbamoyl)-methyl]-2-oxo-6-phenylsulfanylmethyl-2,3,4,7-tetrahydro-1H-azepin-3-yl}-amide.

39. A pharmaceutical composition comprising:

A) an effective amount of one or more compounds, including all enantiomeric or diasteriomeric forms and pharmaceutically acceptable salts thereof, said compound having the formula:

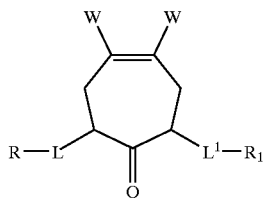

wherein each W is hydrogen of a unit having the formula $-(L^2)_j-R^2$, the index j is 0 or 1;

wherein R is a ring chosen from:
i) substituted or unsubstituted $C_3-C_{10}$ non-aromatic carbocyclic;
ii) substituted or unsubstituted $C_6-C_{10}$ aryl;
iii) substituted or unsubstituted $C_1-C_{10}$ heterocyclic; and
iv) substituted or unsubstituted $C_1-C_{10}$ heteroaryl;

$R^1$ is a cysteine trap;

each $R^2$ is independently selected from the group consisting of:
i) hydrogen;
ii) a hydrocarbyl unit having the formula: $-[C(R^3)_2]_p(CH=CH)_qR^3$;
iii) $-C(=Z)R^3$;
iv) $-C(=Z)AR^3$;
v) $-C(=Z)[C(R^3)_2]_p(CH=CH)_qR^3$;
vi) $-C(=Z)N(R^3)_2$;
vii) $-C(=Z)NR^3N(R^3)_2$;
viii) $-CN$;
xix) $-CF_3$;
x) $-N(R^3)_2$;
xi) $-NR^3CN$;
xii) $-NR^3C(=Z)R^3$;
xiii) $-NR^3C(=Z)N(R^3)_2$;
xiv) $-NHN(R^3)_2$;
xv) $-NHOR^3$;
xvi) $-NO_2$;
xvii) $-OR^3$;
xviii) $-OCF_3$;
xix) $-F, -Cl, -Br,$ or $-I$;
xx) $-SO_3M$;
xxi) $-OSO_3M$;
xxii) $-SO_2N(R3)_2$;
xxiii) $-SO_2R^3$;
xxiv) $-P(O)(OR^3)R^3$;
xxv) $-P(O)(OR^3)_2$;
xxvi) and mixtures thereof;

each $R^3$ is independently hydrogen, substituted or unsubstituted $C^1-C_{20}$, linear, branched, or cyclic alkyl, substituted or unsubstituted $C_4-C_{20}$ aryl, $C_1-C_{20}$ substituted or unsubstituted heterocyclic, $C_1-C_{20}$ substituted or unsubstituted heteroaryl; Z is O, S, or $NR^{3;}$ M is hydrogen, or a salt forming cation; the index p is from 0 to 12; the index q is from 0 to 12;

L, $L^1$, and $L^2$ are each independently a linking group having the formula:

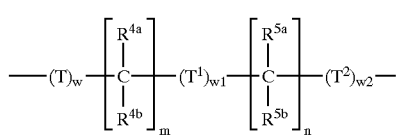

T, $T^1$, and $T^2$ are each independently selected from the group consisting or
i) $-NR^6-$;
ii) $-O-$;
iii) $-S(O)_2$;
iv) $-NR^6S(O)_2-$; and
v) $-S(O)_2NR^6-$;

$R^6$ is hydrogen, substituted or unsubstituted $C_1-C_{10}$ linear, branched, or cyclic alkyl, $C_6-C_{10}$ aryl, and $C_7-C_1$ alkylenearyl; the indices w, $w^1$, and $w^2$ are each independently 0 or 1;

$R^{4a}, R^{4b}, R^{5a}$, and $R^{5b}$ are each independently;
i) hydrogen;
ii) $C_1-C_4$ linear, branched, and cyclic alkyl;
iii) $R^{4a}$ and $R^{4b}$ or $R^{5a}$, and $R^{5b}$ can be taken together to form a carbonyl unit; and
iv) two $R^{3a}$ or two $R^{3b}$ units from adjacent carbon atoms or two $R^{4a}$ or two $R^{4b}$ units from adjacent carbon atoms can be taken together to form a double bond;

the index m is from 0 to 5; the index n is from 0 to 5; and

B) the balance one or more pharmaceutically acceptable excipients.

40. A method for treating one or more interleukin-1β converting enzyme inhibitor mediated or interleukin-1β converting enzyme inhibitor modulated mammalian diseases or conditions, selected from the group consisting of osteoarthritis, rheumatoid arthritis, Huntington's disease, Parkinson's disease, Alzheimer's, diabetes, and human Immunodeficiency virus (HIV), said method comprising the step of administering to a human or higher mammal and effective amount of a composition comprising one or more compounds according to claim 1.

41. A method for treating osteoarthritis in humans or higher mammals, said method comprising the step of administering to a human or higher mammal and effective amount of a composition comprising one or more compounds according to claim 1.

* * * * *